(12) United States Patent
Thaler et al.

(10) Patent No.: US 7,855,227 B2
(45) Date of Patent: Dec. 21, 2010

(54) 2-PHENYLETHYLAMINO DERIVATIVES AS CALCIUM AND/OR SODIUM CHANNEL MODULATORS

(75) Inventors: Florian Thaler, Gerenzano (IT); Mauro Napoletano, Milan (IT); Cibele Sabido-David, Milan (IT); Ermanno Moriggi, Gallarate (IT); Carla Caccia, Cardano Al Campo (IT); Laura Faravelli, Garbagnate Milanese (IT); Alessandra Restivo, Milan (IT); Patricia Salvati, Arese (IT)

(73) Assignee: Newron Pharmaceuticals S.p.A., (MI) (IT)

( * ) Notice: Subject to any disclaimer, the term of this patent is extended or adjusted under 35 U.S.C. 154(b) by 112 days.

(21) Appl. No.: 12/158,491

(22) PCT Filed: Nov. 29, 2006

(86) PCT No.: PCT/EP2006/011443

§ 371 (c)(1),
(2), (4) Date: Jun. 20, 2008

(87) PCT Pub. No.: WO2007/071311

PCT Pub. Date: Jun. 28, 2007

(65) Prior Publication Data

US 2008/0319057 A1 Dec. 25, 2008

(30) Foreign Application Priority Data

Dec. 22, 2005 (EP) .................................. 05028147

(51) Int. Cl.
*A61K 31/34* (2006.01)
*C07D 209/14* (2006.01)

(52) U.S. Cl. ...................................... 514/461; 548/505
(58) Field of Classification Search .................. 514/461; 549/505
See application file for complete search history.

(56) References Cited

U.S. PATENT DOCUMENTS

| | | | |
|---|---|---|---|
| 3,759,979 A | 9/1973 | Beregi et al. | |
| 5,051,403 A | 9/1991 | Miljanich et al. | |
| 5,366,982 A | 11/1994 | Dereu et al. | |
| 5,587,454 A | 12/1996 | Justice et al. | |
| 5,863,952 A | 1/1999 | Orlek et al. | |
| 5,945,454 A * | 8/1999 | Pevarello et al. | 514/620 |
| 6,011,035 A | 1/2000 | Snutch et al. | |
| 6,117,841 A | 9/2000 | Hu et al. | |
| 6,180,624 B1 | 1/2001 | Hill | |
| 6,187,338 B1 | 2/2001 | Caruso et al. | |
| 6,207,685 B1 | 3/2001 | Lallement et al. | |
| 6,242,488 B1 | 6/2001 | Bueno et al. | |
| 6,281,211 B1 | 8/2001 | Cai et al. | |
| 6,290,986 B1 | 9/2001 | Murdock et al. | |
| 6,303,819 B1 | 10/2001 | Pevarello et al. | |
| 6,326,374 B1 | 12/2001 | Magnus et al. | |
| 6,326,385 B1 | 12/2001 | Wickenden et al. | |
| 6,362,174 B1 | 3/2002 | Rafferty et al. | |
| 6,372,792 B1 | 4/2002 | Chouinard | |
| 6,380,198 B1 | 4/2002 | Lisi | |
| 6,420,383 B1 | 7/2002 | Henry | |
| 6,455,538 B1 | 9/2002 | Grauert et al. | |
| 6,458,781 B1 | 10/2002 | Connor et al. | |
| 6,472,530 B1 | 10/2002 | Dodd et al. | |
| 6,479,484 B1 | 11/2002 | Lan et al. | |
| 6,500,825 B2 | 12/2002 | Lan et al. | |
| 6,521,647 B2 | 2/2003 | Foster | |
| 7,091,210 B2 | 8/2006 | Lan et al. | |
| RE40,259 E | 4/2008 | Pevarello et al. | |
| 2002/0016464 A1 | 2/2002 | Lan et al. | |
| 2004/0248978 A1 | 12/2004 | Salvati | |
| 2006/0079570 A1 | 4/2006 | Salvati et al. | |
| 2007/0093495 A1 | 4/2007 | Ruggero et al. | |
| 2007/0203182 A1 | 8/2007 | Besana et al. | |
| 2008/0096965 A1 | 4/2008 | Barbanti et al. | |

FOREIGN PATENT DOCUMENTS

| | | |
|---|---|---|
| DE | 20 06 978 A1 | 9/1970 |
| EP | 1588704 A | 10/2005 |
| GB | 586 645 A | 3/1947 |
| WO | WO 90/14334 A1 | 11/1990 |
| WO | WO 92/01675 A2 | 2/1992 |

(Continued)

OTHER PUBLICATIONS

Alzheimer, C., 2002, "Na+ channels and Ca2+ channels of the cell membrane as targets of neuroprotective substances," *Adv. Exp. Med. Biol.* 513, 161-181.

Baumann P., 1996, "Pharmacokinetic-pharmacodynamic relationship of the selective serotonin reuptake inhibitors," *Clin Pharmacokinet* 31, pp. 444-469.

(Continued)

*Primary Examiner*—Susannah Chung
(74) *Attorney, Agent, or Firm*—Dechert LLP

(57) ABSTRACT

2-Phenylethylamino substituted carboxamide derivatives of formula (I); wherein J, W, $R^0$, $R^1$, $R^2$, $R^3$, and $R^4$ have the meanings as defined in the specification and pharmaceutically acceptable salts thereof, pharmaceutical compositions containing them as active ingredient and their use as sodium and/or calcium channel modulators useful in preventing alleviating and curing a wide range of pathologies, including neurological, psychiatric, cardiovascular, inflammatory, ophthalmic, urology, and gastrointestinal diseases where the above mechanisms have been described as playing a pathological role, are described.

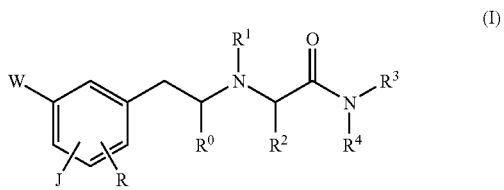

(I)

14 Claims, 1 Drawing Sheet

FOREIGN PATENT DOCUMENTS

| WO | WO 94/08588 | | 4/1994 |
|---|---|---|---|
| WO | WO 97/10210 | A1 | 3/1997 |
| WO | WO 98/35957 | A1 | 8/1998 |
| WO | WO 98/40074 | | 9/1998 |
| WO | WO 99/14199 | | 3/1999 |
| WO | WO 99/26614 | A1 | 6/1999 |
| WO | WO 99/35125 | A | 7/1999 |
| WO | WO 99/55322 | | 11/1999 |
| WO | WO 00/02562 | | 1/2000 |
| WO | WO 00/02592 | | 1/2000 |
| WO | WO 00/53225 | | 9/2000 |
| WO | WO 00/57877 | | 10/2000 |
| WO | WO 00/61188 | | 10/2000 |
| WO | WO 01/07037 | | 2/2001 |
| WO | WO 01/45684 | | 6/2001 |
| WO | WO 01/74779 | A1 | 10/2001 |
| WO | WO 01/98779 | | 12/2001 |
| WO | WO 03/018561 | A1 | 3/2003 |
| WO | WO 03/020273 | | 3/2003 |
| WO | WO 03/037865 | A1 | 5/2003 |
| WO | WO 03/057219 | A1 | 7/2003 |
| WO | WO 03/091219 | | 11/2003 |
| WO | WO 03/091219 | A | 11/2003 |
| WO | WO 2004/062655 | | 7/2004 |
| WO | WO 2004/066987 | | 8/2004 |
| WO | WO 2004/066990 | | 8/2004 |
| WO | WO 2004/087125 | A1 | 10/2004 |
| WO | WO 2004/089353 | A | 10/2004 |
| WO | WO 2005/018627 | A | 3/2005 |
| WO | WO 2005/070405 | | 8/2005 |
| WO | WO 2006/027052 | | 3/2006 |

OTHER PUBLICATIONS

Bowersox S. Scott et al., 1998, "Pharmacotherapeutic potential of omega-conotoxin MVIIA (SNX-111), an N-type neuronal calcium channel blocker found in the venom of *Conus magus*," *Toxicon* 36: 1651-1658.

Catterall, W.A., "Common modes of drug action on Na$^+$ channels: local anesthetics, antiarrhythmics and anticonvulsants," *Trends Pharmacol. Sci.* (1987) 8: 57-65.

Cizkova D. et al., 2002, "Localization of N-type Ca$^{2+}$ channels in the rat spinal cord following chronic constrictive nerve injury," *Exp. Brain Res.* 147: 456-463.

Cooper A. J. et al, 1989, "Tyramine and irreversible monoamine oxidase inhibitors in clinical practice," *J Psych Suppl 38-45*.

Diaz, Alvaro et al., 1997, "Blockade of spinal N- and P-type, but not L-type, calcium channels inhibits the excitability of rat dorsal horn neurones produced by subcutaneous formalin inflammation," *Pain* 69: 93-100.

Hatakeyama, Shinji et al., 2001, Differential nociceptive responses in mice lacking the $\alpha_{1B}$ subunit of N-type Ca$^{2+}$ channels, *Neuroreport* 12 : 2423-2427.

International Search Report for PCT/EP2006/011443 mailed on May 3, 2007.

Kim, Chanki et al., 2001, "Altered Nociceptive Response in Mice Deficient in the $\alpha_{1B}$ Subunit of the Voltage-Dependent Calcium Channel," *Molecular and Cellular Neuroscience* 18: 235-245.

Matthews, Elizabeth A. et al., 2001, "Effects of spinally delivered N- and P-type voltage-dependent calcium channel antagonists on dorsal horn neuronal responses in a rat model of neuropathy," *Pain* 92: 235-246.

Nebe, J. et al., 1998, "Spinal application of ω-contoxin GVIA, an N-type calcium channel antagonist, attenuates enhancement of dorsal spinal neuronal responses caused by intra-articular injection of mustard oil in the rat," *Exp Brain Res* 120:61-69.

Pevarello P. et al., 1998, "Synthesis and anticonvulsant activity of a new class of 2-[(Arylalkyl) amino] alkanamide Derivatives," *J. Med. Chem.* 41: 579-590.

Saegusa, Hironao et al., 2001, Suppression of inflammatory and neuropathic pain symptoms in mice lacking the N-type Ca$^{2+}$ channel, *The EMBO Journal*, 20: 2349-2356.

Vanegas, Horacio et al., 2000, "Effects of antagonists to high-threshold calcium channels upon spinal mechanisms of pain, hyperalgesia and allodynia," *Pain* 85, 9-18.

Volz, Hans-Peter et al., 1998, "Monoamine oxidase inhibitors; A perspective on their use in the elderly," *Drugs & Aging* 13, pp. 341-355.

Yamada et al., 1996, "Pharmacology of antidepressants in the elderly," Ch. 11 in *Handbook of pharmacology of aging*, Roberts et al., editors, Boca Raton: CRC Press.

Int'l. Preliminary Report on Patentability and Written Opinion of the Int'l Searching Authority for Int'l. App. No. PCT/EP2006/011443 dated Jul. 7, 2008.

Arban et al., "Evaluation of the Effects of Lamotrigine, Valproate and Carbamazepine in a Rodent Model of Mania," *Behavioural Brain Research* 158, No. 1:123-132 (Mar. 7, 2005).

Bennett et al., "A Peripheral Mononeuropathy in Rat that Produces Disorders of Pain Sensation Like Those Seen in Man," *Pain* 33, No. 1:87-107 (Apr. 1988).

Chaplan et al., "Quantitative Assessment of Tactile Allodynia in the Rat Paw," *Journal of Neuroscience Methods* 53, No. 1:55-63 (Jul. 1994).

Hamill et al., "Improved Patch-Clamp Techniques for High-Resolution Current Recording from Cells and Cell-Free Membrane Patches," *Pflügers Archiv: European Journal of Physiology* 391, No. 2:85-100 (Aug. 1981).

Pevarello et al., "Synthesis and Anticonvulsant Activity of a New Class of 2-[(arylalky)amino]Alkanamide Derivatives," *Journal of Medicinal Chemistry* 41, No. 4:579-590. doi:10.1021/jm970599m (Feb. 12, 1998).

Robinson et al., "The Neural Basis of Drug Craving: An Incentive-Sensitization Theory of Addiction," *Brain Res Rev* 18, 247-91 (1993).

U.S. Appl. No. 60/126,553, filed Mar. 26, 1999, Hogenkamp.

U.S. Appl. No. 10/856,494, filed Jan. 25, 2007, Barbanti.

U.S. Appl. No. 60/126,056, filed Mar. 23, 1999, Prendergast.

Anonymous, "About Post-Herpetic Neuralgia" www.aftershingles.com (2000).

Anonymous, "Cambridge NeuroScience's grant for channel blockers," *SCRIP World Pharmaceutical News* 1870:8 (1993).

Anonymous, "Formula C22 H26 O4; Catalogue ID E0475-000," Steraloids Inc., Wilton, New Hampshire (downloaded Feb. 24, 2009 from http://steraloids.com) (2006-2008).

Anonymous, "Neurogen Licenses National Institutes of Health (NIH) Anticonvulsants," *SCRIP World Pharmaceutical News* 1773:14 (1992).

Anonymous, "Treatment of Trigeminal Neuralgia at Mayo Clinic" www.mayoclinic.org (2006).

Anonymous, "Trigeminal Neuralgia" www.enwikipedia.org (2006).

Attal, "Antiepileptic drugs in the treatment of neuropathic pain," *Exp. Rev. Neurotherapeutics* 1:199-206, Future Drugs Ltd. (2001).

Awouters (ed.), *Proceedings, XIVth International Symposium on Medicinal Chemistry*, Maastricht, The Netherlands, Sep. 8-12, 1996, Elsevier Science B. V., Amsterdam, (Stanford University Libraries date stamp). Copyright 1997, (date stamped Aug. 24, 1998, Swain Library, Stanford University).

Backonja et al., "Gabapentin for the Symptomatic Treatment of Painful Neuropathy in Patients with Diabetes Mellitus. A Randomized Controlled Trial," *JAMA* 20 2 80 (21):1831-1836 (Dec. 1998).

Bennet, "Neuropathic Pain: An Overview," *Molecular Neurobiology of Pain*, David Borsook, Ed., *Progress in Pain Research and Management*, vol. 9, International Association for the Study of Pain Press, Seattle, USA, pp. 109-113 (1997).

Bennett, "Neuropathic Pain: New Insights, New Interventions," *Hospital Practice* JJ:95-98, pp. 101-104,107-110,113-114, The McGraw-Hill Companies, Inc. (1998).

Bensimon et al., "A Controlled Trial of Riluzole in Amyotrophic Lateral Sclerosis," *New Engl. J. Med.* 330:585-591 (1994).

Beydoun, "Postherpetic Neuralgia: Role of Gabapentin and Other Treatment Modalities," *Epilepsia* 40 (Suppl. 6):551-556, Lippincott Williams & Wilkins (Oct. 1999).

Blinder et al., "Advances in Mood Stabilizing Medications," *West. J. Med.* 169:39-40, BMJ Publishing (1998).

Bolay et al., "Intrinsic Brain Activity Triggers Trigeminal Meningeal Afferents in a Migraine Model," *Nature Medicine*, vol. 8, No. 2, pp. 136-142 (2002).

Borowicz et al., "Effect of Gabapentin on the Anticonvulsant Activity of Antiepileptic Drugs against Electroconvulsions in Mice: An Isobolographic Analysis," *Epilepsia* 43:956-963, Blackwell Publishing. Inc. (2002).

Boyce et a l., "Selective NMDA NR2B Antagonists Induce Antinociception Without Motor Dysfunction: Correlation with Restricted Localisation of NR2B Subunit in Dorsal Horn," *Neuropharmacology* 38:611-623, Pergamon and Elsevier Science Ltd. (May 1999).

Brown et al., "Neuroprotective Properties of Lifarizine Compared with Those of Other Agents in a Mouse Model of Focal Cerebral Ischaemia," *British J. Pharmacol.* 115:1425-1432 (1995).

Bryans et al., "3-Substituted GABA Analogs with Central Nervous System Activity: A Review," *Med. Res. Rev.*, 19:149-177, John Wiley & Sons, Inc. (Mar. 1999).

Buchan et al., "AMPA Antagonists: Do They Hold More Promise for Clinical Stroke Trials Than NMDA Antagonists?" *Supplement I, Stroke* 24:1148-1152, American Heart Association (1993).

Butler et al., "A Limited Arthritic Model for Chronic Pain Studies in the Rat," *Pain* 48, No. 1:73-81 (Jan. 1992).

Calzetti et al., "Absence of Co-Morbidity of Parkinson Disease and Restless Legs Syndrome: A Case-Control Study in Patients Attending a Movement Disorders Clinic," *Neurological Sciences* 30(2) (2009).

Canavero et al., "The Riddle of Trigeminal Neuralgia," *Pain* 60, No. 2:229-231 (Feb. 1995).

Carrazana et al., "Alternative Uses of Lamotrigine and Gabapentin in the Treatment of Trigeminal Neuralgia," *Neurology* 50:1192, The American Academy of Neurology (Apr. 1998).

Catterall, "Neurotoxins that Act on Voltage-Sensitive Sodium Channels in Excitable Membranes," *Ann. Rev. Pharmacol. Toxicol.* 20:15-43 (1980).

Catterall, "Structure and Function of Voltage-Sensitive Ion Channels," *Science* 242:50-61 (1988).

Chapman, et al., "Effects of Systemic Carbamazepine and Gabapentin on Spinal Neuronal Responses in Spinal Nerve Ligated Rats," *Pain* 75:261-272, Elsevier Science B.V. (Apr. 1998).

Chong et al, "Anticonvulsants for the Management of Pain," *Pain Reviews* 7, pp. 129-147 (2000).

Complaint, Civil Action No. 1:07-cv-00487 (Mar. 12, 2007).

Creveling et al., "($^3$H)Batrachotoxinin-A 20α-Benzoate Binding in a Vesicular Preparation from Guinea Pig Cerebral Cortex," *Molecular Pharmacalogy* 23:350-358, The American Society for Pharmacology and Experimental Therapeutics (1983).

Czuczwar et al., "Felbamate, Gabapentin and Topiramate as Adjuvant Antiepileptic Drugs in Experimental Models of Epilepsy," *Polish Journal of Pharmacology*, Polish Academy of Sciences, 53, No. 1:65-68 (Feb. 2001).

Czuczwar et al., "The New Generation of GABA Enhancers, Potential in the Treatment of Epilepsy," *CNS Drugs* 15, No. 5:339-350 (2001).

De Sarro et a l., "Gabapentin Potentiates the Antiseizure Activity of Certain Anticonvulsants in DBA/2 Mice," *Eur. J. Pharmacal.*, Elsevier Science , 349:179-185 (1998).

Decision, Preliminary Motions, Bd.R. 125, interference No. 105,394 (2007).

Denicoff et al., "Efficacy of Carbamazepine Compared With Other Agents: A Clinical Practice Survey," *J. Clin. Psychiatry* 55:70-76 (1994).

Dichter et al., "Drug Therapy: New Antiepileptic Drugs," *The New England Journal of Medicine*, pp. 1583-1588 (Jun. 15, 1996).

Dimmock et al., "(Aryloxy)aryl Semicarbazones and Related Compounds: A Novel Class of Anticonvulsant Agents Possessing High Activity in the Maximal Electroshock Screen," *J. Med. Chem.* 39:3984-3997 (1996).

Donnadieu et al., "Pain Relief," *Presse Medicale*, 27/39, 2062-2069 (1998).

Dostert et al., "New Anticonvulsants with Selective MAO-B Inhibitory Activity," *European Neuropsychopharmacology*, 1(3):317-319 (Sep. 1991).

Dunham et al., "A Note on the Simple Apparatus for Detecting Neurological Deficit in Rats and Mice," *J. of the American Pharmaceutical Association*, 46 (3):208-209 (1957).

Elrifi et al., "Request for *Ex Parte* Reexamination of U.S. Patent No. 6,479,484 B1," on behalf of Newron Pharmaceuticals, SpA filed Jul. 2, 2003.

Faravelli L et al., "NW 1029 is a Novel Na+ Channel Blocker, with Analgesic Activity in Animal Models," *Abstract, Annual Meeting, Society for Neuroscience*, 26 (1):1218 (2000).

Fariello et al., "Preclinical Evaluation of PNU-151774E as a Novel Anticonvulsant," *J. Pharmacol. Exp. Ther.* 285(2):397-403 (May 1998).

Field et al., "Evaluation of Gabapentin and S-(+)-3-isobutylgaba in a Rat Model of Postoperative Pain," *The Journal of Pharmacology and Experimental Therapeutics* 282, No. 3:1242-1246 (Sep. 1997).

Field et al., "Gabapentin and Pregabalin, But Not Morphine and Amitriptyline, Block Both Static and Dynamic Components of Mechanical Allodynia Induced by Streptozocin in the Rat," *Pain* 80, No. 1-2:391-398 (Mar. 1999).

Fields, "Peripheral Neuropathic Pain: An Approach to Management," PD Wall and R Melack (eds.), *Textbook of Pain*, 3$^{rd}$ Ed., Churchill Livingstone, pp. 991-996.

First Declaration of Robert A. McArthur, Pevarello Exhibit 2036, interference 105,394 (2006).

First Declaration of Stephen G. Waxman, M.D., Ph.D., PX 2003, interference No. 105,394 (2006).

Galer, "Neuropathic Pain of Peripheral Origin: Advances in Pharmacologic Treatment," *Neurol.* 45:S17-S25 (1995).

Gallagher et al., "Migraine: Diagnosis, Management, and New Treatment Options," *American Journal of Managed Care* 8: S58-S73 (2002).

Goadsby et al., "The Trigeminovascular System and Migraine: Studies Characterizing Cerebrovascular and Neuropeptide Changes Seen in Humans and Cats," *Ann Neurol.*, 33(1), pp. 48-56 (1993).

Goldberg et al., "Focus on Gabapentin," *Focus* 8:1-6, Priory Lodge, Education Ltd., http://www.priory.com/focus8.htm (1997).

Graham et al., "A Dose-Response Study of Neuroprotection Using the AMPA Antagonist NBQx in Rat Focal Cerebral Ischemia," *J. Pharmacal. Exp. Therap.* 276:1-4, Williams & Wilkins (1996).

Graham et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269:854-859 (1994).

Guieu et al., "Central Analgesic Effect of Valproate in Patients with Epilepsy," *Seizure* 2:147-150 (1993).

Gurney et al., "Benefit of Vitamin E, Riluzole, and Gabapentin in a Transgenic Model of Familial Amyotrophic Lateral Sclerosis," *Am. Neural.* 39:147-157, The American Neurological Association (1996).

Hammer et al., "Effect of Riluzole on Acute Pain and Hyperalgesia in Humans," *Brit. J. Anaesthesia*, 82(5):718-22 (1999).

Hoekstra et al., "Chemical Development of C1-1008, an Enantiomerically Pure Anticonvulsant," *Org. Process Res. Dev.* 1:26-38, American Chemical Society and Royal Society of Chemistry (1997).

Hunskaar et al., "Formalin Test in Mice, A Useful Technique for Evaluating Mild Analgesics," *J. Neurosci. Methods* 14:69-76, Elsevier Science Publishers B.V. (1985).

Iwasaki et al., "CNQX Prevents Spinal Motor Neuron Death Following Sciatic Nerve Transection in Newborn Rats," *J. Neuro Sci.* 134:21-25, Elsevier Science B. V. (1995).

Judgment, Preliminary Motions, Bd.R. 127, interference No. 105,394 (2007).

Kim et al., "An Experimental Model for Peripheral Neuropathy Produced by Segmental Spinal Nerve Ligation in the Rat," *Pain* 50:355-363, Elsevier Science Publishers B. V. (1992).

Kingery, "A Critical Review of Controlled Clinical Trials for Peripheral Neuropathic Pain and Complex Regional Pain Syndromes," *Pain* 73:123-139 (1997).

Koob et al., "Neuroscience of Addiction," *Neuron* 21, No. 3:467-476 (Sep. 1998).

Kudoh et al., "Effect of Carbamazepine on Pain Scores of Unipolar Depressed Patients with Chronic Pain: A Trial of Off-On-Off-On Design," *Clin. J. Pain* 14:61-65, Lippincott-Raven Publishers (1998).
Low et al., "Symptomatic Treatment of Painful Neuropathy," *JAMA* 280:1863-1864, The American Medical Association (Dec. 1981).
Lunardi et al., "Clinical Effectiveness of Lamotrigine and Plasma Levels in Essential and Symptomatic Trigeminal Neuralgia," *Neurology* 48(6):1714-1717 (1997).
Magnus, "Nonepileptic Uses of Gabapentin Experience," *Epilepsia*, Suppl. 6, 40:S66-72, Discussion 873-874 (1999).
Mathew, "Pathophysiology, Epidemiology and Impact of Migraine," *Clinical Cornerstone*, vol. 4, No. 3, pp. 1-17 (2001).
May et al., "The Trigeminovascular System in Humans: Pathophysiologic Implications for Primary Headache Syndromes of the Neural Influences on the Cerebral Circulation," *J. Cereb. Blood flow Metab.*, vol. 9, pp. 115-127 (1999).
McQuay et al., "Anticonvulsant Drugs for Management of Pain: A Systematic Review," *BMJ* 311:1047-1052 (Oct. 21, 1995).
Memorandum Opinion and Order, interference No. 105,394 (2007).
Miller, "Novascreen Data—Project Summary for Hunter-Fleming," Dechert LLP (Jan. 14, 2010).
Mounsey et al., "Herpes Zoster and Postherpetic Neuralgia," *American Family Physician*, vol. 72, No. 6, pp. 1075-1080 (2005).
Nakamura-Craig et al., "Effect of Lamotrigine in the Acute and Chronic Hyperalgesia Induced by $PGE_2$ and in the Chronic Hyperalgesia in Rats with Streptozocin-Induced Diabetes," *Pain* 63:33-37 (1995).
Newron Pharmaceuticals Press Release, "Anounces Data of Phase I Clinical Trials," (downloaded from http://www.newron.com/uploads/AnnouncesdataofphaseIclinicaltrials.pdf) dated Feb. 18, 2009.
Newron Pharmaceuticals Press Release, "Safinamide Phase II Data," (downloaded from http://www.newron.com/uploads/SafinamidePhaseIIdataFinal090103.pdf) dated Feb. 18, 2009.
Nicholson, "Gabapentin Use in Neuropathic Pain Syndromes," *Dolor* 14:243-250, Publicaciones Permanyer (1999).
Nicolaus, "Symbiotic Approach to Drug Design," *Decision Making in Drug Research, Raven Press*, pp. 173-186 (1983).
Notice of Dismissal with Prejudice, Civil Action No. 1:07-cv-00487 (Jul. 25, 2007).
Ohizumi et al., "Specific Inhibitors of [3H1 Saxitoxin Binding to Skeletal Muscle Sodium Channels by Geographutoxin II, a Polypeptide Channel Blocker," *J. Biol. Chem.*, The American Society of Biological Chemists. Inc., 261:6149-6152 (1986).
Olanow et al., "Modeling Parkinson's Disease," *Annals of Neurology*, vol. 66, No. 4, pp. 432-436 (2009).
Olanow et al., "The Scientific and Clinical Basis for the Treatment of Parkinson Disease," *Neurology*, vol. 72, Suppl. 4, pp. S1-S136 (2009).
Olanow et al., "Clinical Pattern and Risk Factors for Dyskinesias Following Fetal Nigral Transplantation in Parkinson's Disease: a Double-Blind Video-Based Analysis," *Movement Disorders* 24:336-343 (2009).
Pan et al., "Gabapentin Suppresses Ectopic Nerve Discharges and Reverses Allodynia in Neuropathic Rats," *J.Pharmacol. Exp. Ther.* 288(3):1026-1030 (1999).
Peitl et al., "Capsaicin-Insensitive Sensory-Efferent Meningeal Vasodilatation Evoked by Electrical Stimulation of Trigeminal Nerve Fibres in the Rat," *British Journal of Pharmacology* 127:457-467 (1999).
Pevarello et al., "Reductive Alkylation of α-Aminoamides," *Organic Preparations and Procedures Int.* 28(2):179-183 (1996).
Pevarello et al., "Stereoselectivity, Sigma Binding and Sodium Channel Blocking Activity of 2-Aminopropanamide Anticonvulsants," *Abstracts, XIVth International Symposium on Medicinal Chemistry*, Maastricht, the Netherlands, Sep. 8-12, 1996 (no date ascribed).
Pietrobon et al., "Neurobiology of Migraine," *Nature Reviews Neuroscience*, vol. 4, 386-398 (2003).
Przesmycki et al., "Isobolographic Analysis of Interaction Between Intrathecal Morphine and Clonidine in the Formalin Test in Rats," *Eur. J. of Pharmacology*, 337: 11-17 (1997).
Puig et al., "Formalin-Evoked Activity in Identified Primary Afferent Fibers: Systemic Lidocaine Suppresses Phase-2 Activity," *Pain* 64:345-355 (1995).

Reuter et al., "Experimental Models of Migraine," *Functional Neurology*, 15: Suppl. 3, (2000).
Rosenberg et al., "The Effect of Gabapentin on Neuropathic Pain," *Clin. J. Pain* 13:251-255, Lippincott-Raven Publishers (1997).
Rosland et al., "The Formalin Test in Mice: Effect of Formalin Concentration," *Pain* 42, No. 2: 235-242 (Aug. 1990).
Rosner et al., "Gabapentin Adjunctive Therapy in Neuropathic Pain States," *The Clinical Journal of Pain* 12, No. 1: 56-58 (Mar. 1996).
Rowbotham et al., "Gabapentin for the Treatment of Postherpetic Neuralgia. A Randomized Controlled Trial," *JAMA, The Great American Medical Association* 280: 1837-1842 (Dec. 2, 1998).
Ryan et al., "Restless Leg Syndrome," *Journal of Pharmacy Practice*, 20: 430-448 (2007).
Sabido-David et al., "The Therapeutic Potential of Na+ and Ca2+ Channel Blockers in Pain Management," *Expert Opinion on Investigational Drugs* 13, No. 10: 1249-1261, doi:10.1517/13543784.13.10.1249 (Oct. 2004).
Salvati et al., "Anticonvulsant Profile of FCE26743A (PNU-151774), A Novel 2-Aminopropionamide Derivative," Society for Neuroscience, Washington, Nov. 15-21, 1996.
Satija et al., "Restless Legs Syndrome: Pathophysiology, Diagnosis and Treatment," *CNS Drugs*, 22, 497518 (2008).
Saxena et al., "Pharmacology of Antimigraine Drugs," *Journal of Neurology*, pp. S28-S35 (1991).
Sheardown et al., "AMPA, But Not NMDA, Receptor Antagonism is Neuroprotective in Gerbil Global Ischaemia, Even When Delayed 24h," *European Journal of Pharmacology* 236:347-353 (1993).
Shibata et al., "Modified Formalin Test: Characteristic Biphasic Pain Response," *Pain* 38:347-352 (1989).
Sist et al., "Experience With Gabapentin for Neuropathic Pain in the Head and Neck: Report of Ten Cases," *Reg. Anesth*. 22:473-478, The American Society of Regional Anesthesia (1997).
Solaro et al., "A Patient with Multiple Sclerosis and Down's Syndrome with A Rare Paroxysmal Symptom at Onset," *Eur. J. Neurol*. 6:505-507, Lippincott Williams & Wilkins (Jul. 1999).
Steiner et al., "Lamotrigine Versus Placebo in the Prophylaxis of Migraine With and Without Aura," *Cephalgia*, vol. 17, pp. 109-112 (1997).
Strittmatter et al., "Cerebrospinal Fluid Neuropeptides and Monoaminergic Transmitters in Patients With Trigeminal Neuralgia," *Headache*, vol. 37, pp. 211-216 (1997).
Stys et al., "Ionic Mechanism of Anoxic Injury in Mammalian CNS White Matter: Role of $Na_+$ Channels and $Na^+$-$Ca^{2+}$ Exchanger," *J. Neurosci*. 12:430-439 (1992).
Tallarida et al., "Efficient Designs for Studying Synergistic Drug Combinations," *Life Sciences*, vol. 61, No. 26, 417-425 (1997).
Tallarida, "Statistical Analysis of Drug Combinations for Synergism," *Pain*, 49: 93-97 (1992).
Tanelian et al., "Neuropathic pain can be relieved by drugs that are use-dependent sodium channel blockers: lidocaine, carbamazepine, and mexiletine," *Anesthesiol*. 74(5):949-951 (1991).
Tanelian et al., "Sodium Channel-Blocking Agents: Their Use in Neuropathic Pain Conditions," *Pain Forum* 4(2):75-80 (1995).
Taylor et al., "$Na^+$ Channels as Targets for Neuroprotective Drugs," *Trends Pharmacol. Sci*. 16:309-316 (1995).
Tjølsen et al., "The Formalin Test: An Evaluation of the Method," *Pain* 51, No. 1, pp. 5-17 (Oct. 1992).
Tremont-Lukats et al., "Anticonvulsants for Neuropathic 30 Pain Syndromes: Mechanisms of Action and Place in Therapy," *Drugs*, 60(5):1029-52 (2000).
Vaghi et al., "Neuroprotective Effect of PNU-151774E, A New Anticonvulsant Compound, in the Model of Global Ischaemia in Gerbils," from *Abstracts, Society for Neuroscience, 27th Annual Meeting*, New Orleans, LA (Oct. 25-30, 1997).
Varasi et al., "Synthesis and Anticonvulsant Activity of New Benzyloxybenzylacetamide Derivatives," from *Abstracts, XIIth International Symposium on Medicinal Chemistry*, Basel, Switzerland (Sep. 13-17, 1992).
Veneroni et al., "NW-1029: A Potent NA Channel Blocker with Anti Hyperalgesic Effect in Animal Models of Inflammatory and Neuropathic Pain," *Society for Neuroscience Abstract Viewer and Itinerary Planner*, SFN 32nd Annual Meeting, Orlando, FL, Abstract No. 454.3 (Nov. 2-7, 2002).

Verdoorn et al., "Functional Properties of Recombinant Rat $GABA_A$ Receptors Depend upon Subunit Composition," *Neuron* 4:919-928, Cell Press (Jun. 1990).

Victor et al., "Chapter 352: Diseases of the Cranial Nerves," in *Harrison's Principles of Internal Medicine*, 11th Edition, pp. 2035-2040, Braunwald et al., eds., McGraw-Hill Inc (1987).

Vieth et al., "Characteristic Physical Properties and Structural Fragments of Marketed Oral Drugs," *J. Med. Chem.*, Supplemental data, 47:224-232 (2004) (downloaded Aug. 20, 2007 from http://pubs.acs.org) (excerpted fields).

Vilarino-Guell et al., "Susceptibility Genes for RLS are Not Associated with PD," *Neurology*, 71:222-223 (Jul. 15, 2008).

Wamil et al., "Limitation by Gabapentin of High Frequency Action Potential Firing by Mouse Central Neurons in Cell Culture," *Epilepsy Res.* 17:1-11, Elsevier Science B. V. (1994).

Wang et al., "Neurosteroid Analogues Part 13: Synthetic Methods for the Preparation of 2β-Hydroxygonane Derivatives as Structural Mimics of ent-3α-Hydroxysteroid Modulators of $GABA_A$ Receptors," *Tetrahedron* 63:7977-7984 (2007).

Webber, "Observations Under Article 115 EPC," in EP 98958114.5 (EP 1032377) on behalf of Newron Pharmaceuticals, SpA, filed Nov. 19, 2002.

Wenzel et al., "Migraine Headache Misconceptions: Barriers to Effective Care," *Pharmacotherapy*, vol. 24, No. 5, pp. 638-648 (2004).

Wilton, "Tegretol in the Treatment of Diabetic Neuropathy," *S. A. Medical Journal* 48(20):869-872 (Apr. 27, 1974).

Woolf et al., "The Systemic Administration of Local Anaesthetics Produces a Selective Depression of C-Afferent Fibre Evoked Activity in the Spinal Cord," *Pain* 23(4):361-374 (1985).

Wrathall et al., "Amelioration of Functional Deficits from Spinal Cord Trauma witb Systemically Administered NBQX, an Antagonist of Non-N-met hyl-D-aspartate receptors," *Experimental Neurology* 137:119-126 (1996).

Yoon et al., "Evaluation of Interaction between Gabapentin and Ibuprofen on the Formalin Test in Rats," *Anesthesiology* 91:1006-1013 (Oct. 1999).

Zagaria, "Posthepetic Neuralgia: A High-Risk Complication in Seniors with Herpes Zoster," *US. Pharmacist*, vol. 27, No. 10 (Oct. 15, 2002).

Official Action, counterpart Brazilian App. (to RE40,259) No. PI9814548-7, English Translation dated Aug. 14, 2007.

Int'l. Preliminary Examination Report for Int'l. App. No. PCT/GB01/00627 dated Aug. 9, 2002.

Int'l. Search Report for Int'l. App. No. PCT/GB01/00627 dated Aug. 23, 2001.

Written Opinion for Int'l. App. No. PCT/EP98/08157 dated Sep. 21, 1999.

Int'l. Preliminary Examination Report for Int'l. App. No. PCT/EP02/08910 dated Jan. 9, 2004.

Int'l. Search Report for Int'l. App. No. PCT/EP02/08910 dated May 7, 2003.

Int'l. Preliminary Examination Report for Int'l. App. No. PCT/EP03/12889 dated Oct. 8, 2004.

Int'l. Search Report for Int'l. App. No. PCT/EP03/12889 dated Feb. 13, 2004.

Int'l. Preliminary Report on Patentability for Int'l. App. No. PCT/EP05/08200 dated Jan. 15, 2007.

Int'l. Search Report for Int'l. App. No. PCT/EP05/08200 dated Mar. 31, 2006.

Written Opinion of the Int'l. Searching Authority for Int'l. App. No. PCT/EP05/08200 dated Mar. 30, 2006.

Int'l. Preliminary Report on Patentability and Written Opinion of the Int'l. Searching Authority for Int'l. App. No. PCT/EP2007/005105 dated Jan. 22, 2009.

Int'l. Search Report for Int'l. App. No. PCT/EP2007/005105 dated Aug. 23, 2007.

Int'l. Preliminary Report on Patentability and Written Opinion of the Int'l. Searching Authority for Int'l. App. No. PCT/EP2007/005197 dated Dec. 16, 2008.

Int'l. Search Report for Int'l. App. No. PCT/EP2007/005197 dated Jan. 21, 2008.

Int'l. Preliminary Report on Patentability and Written Opinion of the Int'l. Searching Authority for Int'l. App. No. PCT/IB2004/001408 dated Oct. 14, 2005.

Int'l. Search Report for Int'l. App. No. PCT/IB2004/001408 dated Oct. 19, 2004.

Int'l Preliminary Report on Patentability for Int'l App. No. PCT/IB2004/001574 dated Dec. 19, 2005.

Written Opinion of the Int'l. Searching Authority for Int'l. App. No. PCT/IB2004/001574 dated Nov. 1, 2004.

Int'l. Preliminary Report on Patentability for Int'l. App. No. PCT/EP2005/004166 dated Jul. 25, 2006.

Int'l. Search Report for Int'l. App. No. PCT/EP2005/004166 dated Aug. 8, 2005.

Written Opinion of the Int'l. Searching Authority for Int'l. App. No. PCT/EP2005/004166 dated Aug. 4, 2005.

Int'l. Preliminary Report on Patentability and Written Opinion of the Int'l Searching Authority for Int'l. App. No. PCT/EP2008/003848 dated Dec. 17, 2009.

Int'l. Preliminary Examination Report for Int'l. App. No. PCT/GB01/02929 dated May 13, 2002.

Int'l. Search Report for Int'l. App. No. PCT/GB01/02929 dated Nov. 14, 2001.

Int'l. Preliminary Examination Report for Int'l. App. No. PCT/GB01/02937 dated May 13, 2002.

Int'l. Search Report for Int'l. App. No. PCT/GB01/02937 dated Nov. 29, 2001.

Non-Final Office Action for U.S. Appl. No. 10/203,880 dated Feb. 10, 2004.

Final Office Action for U.S. Appl. No. 10/203,880 dated Sep. 3, 2004.

Notice of Allowance for U.S. Appl. No. 11/359,982 dated Nov. 30, 2007.

Request for Continued Examination (RCE) for U.S. Appl. No. 11/359,982 dated Oct. 15, 2007.

Final Office Action for U.S. Appl. No. 11/359,982 dated Jun. 25, 2007.

Response for U.S. Appl. No. 11/359,982 dated May 7, 2007.

Non-Final Office Action for U.S. Appl. No. 11/359,982 dated Nov. 6, 2006.

Non-Final Office Action for U.S. Appl. No. 10/487,931 dated Dec. 2, 2009.

Request for Continued Examination (RCE) for U.S. Appl. No. 10/487,931 dated Sep. 18, 2009.

Request for Pre-Appeal Conference for U.S. Appl. No. 10/487,931 dated Jun. 12, 2009.

Non-Final Office Action for U.S. Appl. No. 10/487,931 dated Jan. 14, 2009.

Request for Continued Examination (RCE) for U.S. Appl. No. 10/487,931 dated Oct. 8, 2008.

Final Office Action for U.S. Appl. No. 10/487,931 dated Jun. 11, 2008.

Response for U.S. Appl. No. 10/487,931 dated Apr. 29, 2008.

Non-Final Office Action for U.S. Appl. No. 10/487,931 dated Oct. 29, 2007.

Notice of Allowance for U.S. Appl. No. 10/541,195 dated Nov. 2, 2009.

Request for Continued Examination (RCE) for U.S. Appl. No. 10/541,195 dated Sep. 11, 2009.

Final Office Action for U.S. Appl. No. 10/541,195 dated Mar. 12, 2009.

Response for U.S. Appl. No. 10/541,195 dated Dec. 9, 2008.

Non-Final Office Action for U.S. Appl. No. 10/541,195 dated Sep. 18, 2008.

Response for U.S. Appl. No. 10/541,195 dated May 21, 2008.

Non-Final Office Action for U.S. Appl. No. 10/541,195 dated Dec. 14, 2007.

Non-Final Office Action for U.S. Appl. No. 11/574,751 dated Feb. 19, 2010.

Request for Pre-Appeal Conference for U.S. Appl. No. 11/574,751 dated Oct. 2, 2009.

Advisory Action for U.S. Appl. No. 11/574,751 dated Sep. 14, 2009.

Final Office Action for U.S. Appl. No. 11/574,751 dated Jul. 22, 2009.

Response for U.S. Appl. No. 11/574,751 dated Apr. 6, 2009.

Non-Final Office Action for U.S. Appl. No. 11/574,751 dated Jan. 5, 2009.
Final Office Action for U.S. Appl. No. 10/312,523 dated Jun. 19, 2009.
Affidavit Rule 131 or 132 for U.S. Appl. No. 10/312,523 dated Jul. 14, 2008.
Response for U.S. Appl. No. 10/312,523 dated Jul. 14, 2008.
Non-Final Office Action for U.S. Appl. No. 10/312,523 dated Jan. 14, 2008.
Response for U.S. Appl. No. 10/312,523 dated Jul. 25, 2007.
Non-Final Office Action for U.S. Appl. No. 10/312,523 dated Mar. 26, 2007.
Affidavit Rule 131 or 132 for U.S. Appl. No. 10/312,523 dated Nov. 28, 2006.
Supplemental Response for U.S. Appl. No. 10/312,523 dated Nov. 28, 2006.
Affidavits Rule 131 or 132 for U.S. Appl. No. 10/312,523 dated Oct. 5, 2006.
Response for U.S. Appl. No. 10/312,523 dated Oct. 5, 2006.
Response for U.S. Appl. No. 10/312,523 dated Jun. 20, 2006.
Affidavit Rule 131 or 132 for U.S. Appl. No. 10/312,523 dated Jun. 20, 2006.
Non-Final Office Action for U.S. Appl. No. 10/312,523 dated Dec. 21, 2005.
Response for U.S. Appl. No. 10/312,523 dated Jul. 28, 2005.
Non-Final Office Action for U.S. Appl. No. 10/312,523 dated Feb. 28, 2005.
Response for U.S. Appl. No. 10/312,523 dated Oct. 1, 2004.
Non-Final Office Action for U.S. Appl. No. 10/312,523 dated Jul. 1, 2004.
Notice of Allowance for U.S. Appl. No. 10/312,533 dated Nov. 9, 2009.
Response for U.S. Appl. No. 10/312,533 dated Aug. 28, 2009.
Non-Final Office Action for U.S. Appl. No. 10/312,533 dated May 11, 2009.
Affidavit Rule 131 or 132 for U.S. Appl. No. 10/312,533 dated Feb. 25, 2009.
Request for Continued Examination (RCE) for U.S. Appl. No. 10/312,533 dated Feb. 25, 2009.
Final Office Action for U.S. Appl. No. 10/312,533 dated Sep. 2, 2008.
Affidavits Rule 131 or 132 for U.S. Appl. No. 10/312,533 dated May 30, 2008.
Response for U.S. Appl. No. 10/312,533 dated May 30, 2008.
Non-Final Office Action for U.S. Appl. No. 10/312,533 dated Nov. 30, 2007.
Request for Continued Examination (RCE) for U.S. Appl. No. 10/312,533 dated Sep. 26, 2007.
Final Office Action for U.S. Appl. No. 10/312,533 dated Mar. 27, 2007.
Response for U.S. Appl. No. 10/312,533 dated Jan. 12, 2007.
Non-Final Office Action for U.S. Appl. No. 10/312,533 dated Jul. 12, 2006.
Non-Final Office Action for U.S. Appl. No. 10/559,982 dated Mar. 16, 2010.
Affidavits Rule 131 or 132 for U.S. Appl. No. 10/559,982 dated Nov. 13, 2009.
Request for Continued Examination (RCE) for U.S. Appl. No. 10/559,982 dated Nov. 13, 2009.
Final Office Action for U.S. Appl. No. 10/559,982 dated Sep. 17, 2009.
Response for U.S. Appl. No. 10/559,982 dated Jun. 24, 2009.
Non-Final Office Action for U.S. Appl. No. 10/559,982 dated Dec. 24, 2008.
Final Office Action for U.S. Appl. No. 10/569,403 dated Feb. 23, 2009.
Response for U.S. Appl. No. 10/569,403 dated Dec. 3, 2008.
Non-Final Office Action for U.S. Appl. No. 10/569,403 dated Jul. 3, 2008.
Response for U.S. Appl. No. 11/578,988 dated Oct. 13, 2009.
Non-Final Office Action for U.S. Appl. No. 11/578,988 dated Aug. 17, 2009.
Affidavit Rule 131 or 132 for U.S. Appl. No. 11/578,988 dated Jun. 5, 2009.
Request for Continued Examination (RCE) for U.S. Appl. No. 11/578,988 dated Jun. 5, 2009.
Final Office Action for U.S. Appl. No. 11/578,988 dated Dec. 11, 2008.
Response for U.S. Appl. No. 11/578,988 dated Aug. 11, 2008.
Non-Final Office Action for U.S. Appl. No. 11/578,988 dated Mar. 10, 2008.

* cited by examiner

2-PHENYLETHYLAMINO DERIVATIVES AS CALCIUM AND/OR SODIUM CHANNEL MODULATORS

CROSS-REFERENCE TO RELATED APPLICATIONS

This application is a §371 national phase of PCT/EP2006/011443, filed 29 Nov. 2006, which claims priority benefit to European application no. EP 05028147.6, filed 22 Dec. 2005, the disclosures of which are incorporated herein by reference in their entireties.

The present invention relates to phenylethylamino derivatives, pharmaceutically acceptable salts thereof, pharmaceutical compositions containing them and their use as sodium and/or calcium channel modulators.

The phenylethylamino derivatives, object of the invention, are active as calcium and/or sodium channel modulators and therefore useful in preventing alleviating and curing a wide range of pathologies, including but not limited to neurogical, psychiatric, cardiovascular, inflammatory, ophthalmic, urogenital, and gastrointestinal diseases where the above mechanisms have been described as playing a pathological role.

The compounds of this invention are substantially free from any MAO inhibitory effect or exhibit a significantly reduced MAO inhibitory effect at dosage that are therapeutically effective in preventing, alleviating and/or curing the above said affections.

BACKGROUND OF THE INVENTION

Chemical Background

The patent application WO 90/14334 describes mono-substituted N-phenylalkyl alpha-amino carboxamide derivatives of the following general formula

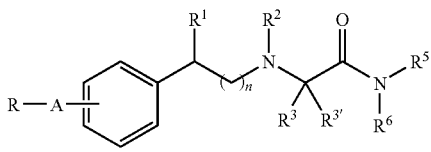

wherein

R is a $(C_1-C_8)$alkyl, $(C_3-C_8)$cycloalkyl, furyl, thienyl, pyridyl or a phenyl ring optionally substituted by 1 to 4 substituents independently selected from halo, $(C_1-C_6)$alkyl, $(C_1-C_6)$alkoxy and trifluoromethyl; A is a —$(CH_2)_m$—, —$(CH_2)_p$—X—$(CH_2)_q$— group wherein m is an integer of 1 to 4, one of p and q is zero and the other is zero or an integer of 1 to 4, X is —O—, —S— or —NR$^4$— in which R$^4$ is hydrogen or $(C_1-C_4)$alkyl; n is 0 or 1; each of R$^1$ and R$^2$ independently is hydrogen or $(C_1-C_4)$alkyl; R$^3$ is hydrogen, $(C_1-C_4)$alkyl optionally substituted by hydroxy or phenyl optionally substituted as above; R$^{3'}$ is hydrogen or R$^3$ and R$^{3'}$ taken together form a $(C_3-C_6)$cycloalkyl ring; each of R$^5$ and R$^6$ independently is hydrogen or $(C_1-C_6)$ alkyl; and their use as antiepileptic, anti-Parkinson, neuroprotective, anti-depressant, anti-spastic and/or hypnotic agents.

The compound 2-[2-[4-(3-chlorobenzyloxy)-phenyl]-ethylamino]-acetamide and its hydrochloride salt and the preparation thereof are specifically described in the above patent application. (See also P. Pevarello and al. in J. Med. Chem. 1998, 41, 579-590.)

The compounds (S)-2-[2-[4-benzyloxy-phenyl]-ethylamino]-acetamide, (S)-2-[2-[4-(2-cholorobenzyloxy)-phenyl]-ethylamino]-acetamide, 2-[2-(4-benzyl-phenyl)-ethylamino]-acetamide and 2-[2-(4-benzylamino-phenyl)-ethylamino]-acetamide are mentioned, but not characterized, in WO 90/14334.

The patent application WO 04/089353 describes a method and a combination therapy for the treatment of Parkinson' disease by using safinamide ((S)-(+)-2-[4-(3-fluoro-benzyloxy)benzylamino]-propanamide), a safinamide derivative or a MAO-B inhibitor together with anti-Parkinsonian agents. The compound 2-[2-[4-(3-chloro-benzyloxy)-phenyl]-ethylamino]-acetamide is exemplified in the invention.

The above compound is also prepared and described as anticonvulsivant (Pevarello P., Bonsignori A., Dostert P., Heidempergher F., Pinciroli V., Colombo M., McArthur R. A., Salvati P., Post C., Fariello R. G., Varasi M. J. Med. Chem. (1998) 41: 579-590).

The patent application WO 99/35125 describes alpha-aminoamide derivatives of the general formula

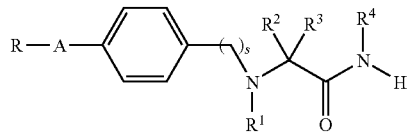

wherein

R is a furyl, thienyl, pyridyl or a phenyl ring; A is a —$(CH_2)_m$—, —$(CH_2)_n$—X— or —$(CH_2)_n$—O— group wherein m is an integer of 1 to 4, n is zero or an integer of 1 to 4, X is —S— or —NH— and v is zero or an integer of 1 to 5; s is 1 or 2; R$^1$ is hydrogen or $(C_1-C_4)$alkyl; one of R$^2$ and R$^3$ is hydrogen and the other is hydrogen or $(C_1-C_4)$alkyl optionally substituted by hydroxy or phenyl; or R$^2$ and R$^3$ taken together form a $(C_3-C_6)$cycloalkyl ring; or R$^2$ and R$^3$ are both methyl; R$^4$ is hydrogen or $C_1-C_4$ alkyl; and their use as analgesic agents.

The compound 2-[2-[4-(3-chloro-benzyloxy)-phenyl]-ethylamino]-propanamide in the above patent application is mentioned.

The patent application WO 03/091219 describes 5-(benzyloxy)-2-(iodophenyl)-ethylamino derivatives (see formula XII), which are employed as intermediates in the preparation of isoquinolines as monoamine oxidase B inhibitors useful against Alzheimer's disease and senile dementia:

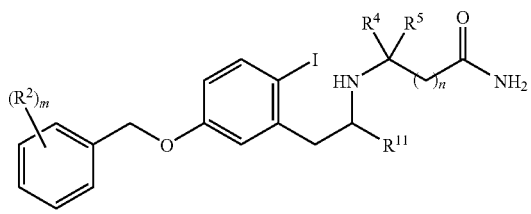

wherein, inter alia, m is 1, 2, or 3; R$^2$ is selected from halogen, halogen —$(C_1-C_6)$alkyl, cyano, $(C_1-C_6)$alkoxy or halogen —$C_1-C_6)$alkoxy; R$^{11}$ is hydrogen; n is 0, 1 or 2; R$^4$ and R$^5$ are independently selected from hydrogen, $(C_1-C_6)$alkyl, —$(CH_2)_p$—OR$^8$, —$(CH_2)_p$—SR$^8$ or benzyl, wherein p is 1 or 2 and R$^8$ is hydrogen or $(C_1-C_6)$alkyl.

WO 99/26614 discloses substituted 2-(benzylamino)acetamides and their use for treating disorders responsive to the blockade of sodium ion channels, including preventing or ameliorating neuropathic pain.

WO 03/037865 relates to compounds useful in the treatment of cancer of general formula

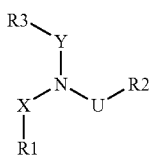

wherein the symbols $R^1$, $R^2$, $R^3$ X, U and Y may assume a wide series of meanings. Although some combinations of said broad generic meanings might include phenethylamino derivatives, none of the compounds described in this application is actually disclosed in WO 03/037865.

U.S. Pat. No. 5,366,982 (WO 92/01675) relates to compounds having selective leucotriene $B_4$ ($LTB_4$) antagonist properties, encompassed by the general formula

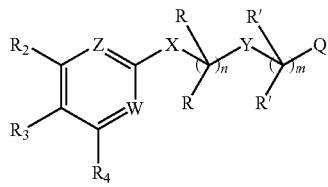

wherein the symbols R, R', $R^2$, $R^3$, $R^4$, X, Y, Z W, n, m and Q may assume a wide series of meanings. Notwithstanding some combinations of said generic meanings might encompass also phenethylamino derivatives, none of the compounds described in this application is actually disclosed in U.S. Pat. No. 5,366,982.

WO 98/35957 discloses acetamide derivatives active as antagonists of neuropeptide Y receptor, particularly useful in the treatment of obesity, of general formula

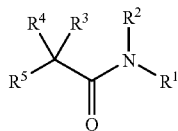

where the symbols $R^1$, $R^2$, $R^3$, $R^4$ and $R^5$ may assume a wide series of meanings. None of the compounds described in this application is actually disclosed in WO 98/35957.

EP 1588704A discloses alfa-aminoamide derivatives, including (S)-(+)-2-[4-(2-fluorobenzyloxy)-benzylamino]-propanamide, i.e. ralfinamide, for use in the treatment of Restless Leg Syndrome.

WO 2005/018627 discloses alfa-aminoamide derivatives, including ralfinamide, for use as therapeutic anti-inflammatory agents Biological Background Calcium channels are membrane-spanning, multi-subunit proteins that allow controlled entry of calcium ions into cells from the extracellular fluid. Commonly, calcium channels are voltage dependent and are referred to as voltage-gated calcium channels (VGCC). VGCCs are found throughout the mammalian nervous system, where they regulate the intracellular calcium ions levels that are important for cell viability and function. Intracellular calcium ion concentrations are implicated in a number of vital processes in animals, such as neurotransmitter release, muscle contraction, pacemaker activity and secretion of hormones. All "excitable" cells in animals, such as neurons of the central nervous system (CNS), peripheral nerve cells, and muscle cells, including those of skeletal muscles, cardiac muscles and venous and arterial smooth muscles, have voltage dependent calcium channels.

Calcium channels are a large family with many genetically, physiologically, and pharmacologically distinct subtypes. Based on the biophysical properties of calcium currents recorded from individual neurons, two super-families have been described: High Voltage Activated (HVA) and Low Voltage Activated (LVA) calcium channels. Calcium currents referred as L-Type, P-Type, Q-Type, N-Type, R-Type are HVA and as T-Type are LVA. In particular, the term "L-type" was originally applied to channels with a large single channel conductance and long open time, and "T-type" was applied to channels with a tiny single channel conductance and a transient open time. Further exploration of functional calcium channel diversity identified the "N-type" channel expressed in neurons and the "P-type" channel, which is the dominant type expressed in cerebellar Purkinje neurons and is pharmacologically resistant to known blockers of L-type and N-type calcium channels. From the molecular identity, ten distinct calcium subtypes have been identified, cloned and expressed and grouped in three families: Cav1 family (Cav 1.1, 1.2, 1.3, 1.4) is functionally related to the L-type Ca current; Cav2 family (Cav 2.1, 2.2, 2.3) is functionally related to the P/Q, N, R-type currents and Cav3 (Cav 3.1, 3.2, 3.3) family is functionally related to the T-type current.

It is believed that calcium channels are relevant in certain disease states. A number of compounds useful in treating various cardiovascular diseases in mammals, including humans, are thought to exert their beneficial effects by modulating functions of voltage dependent calcium channels present in cardiac and/or vascular smooth muscle. Compounds with activity against calcium channels have also been implicated for the treatment of pain. In particular N-type calcium channels (Cav2.2), responsible for the regulation of neurotransmitter release, are thought to play a significant role in nociceptive transmission, both due to their tissue distribution as well as from the results of several pharmacological studies. N-type calcium channels were found up-regulated in the ipsilateral dorsal horn in neuropathic pain models of injury (Cizkova D., Marsala J., Lukacova N., Marsala M., Jergova S., Orendacova J., Yaksh T. L. Exp. Brain Res. (2002) 147: 456-463). Specific N-type calcium channel blockers were shown to be effective in reducing pain responses in neuropathic pain models (Mattews E. A., Dickenson A. H. Pain (2001) 92: 235-246), in the phase II of the formalin test (Diaz A., Dickenson A. H. Pain (1997) 69: 93-100) and the hyperalgesia initiated by knee joint inflammation (Nebe J., Vanegas H., Schaible H. G. Exp. Brain Res. (1998) 120: 61-69). Mutant mice, lacking the N-type calcium channels, were found to have a decreased response to persistent pain as seen by a decrease in pain response during phase II of the formalin test (Kim C., Jun K., Lee T., Kim S. S., Mcenery M. W., Chin H., Kim H. L, Park J. M., Kim D. K., Jung S. J., Kim J., Shin H. S. Mol. Cell. Neurosci. (2001) 18: 235-245; Hatakeyama S., Wakamori M, Ino M., Miyamoto N., Takahashi E., Yoshinaga T., Sawada K., Imoto K., Tanaka I., Yoshizawa T., Nishizawa Y., Mori Y., Nidome T., Shoji S, Neuroreport (2001) 12: 2423-2427) as well as to neuropathic pain, assessed by a decrease in mechanical allodynia and thermal hyperalgesia in the spinal nerve ligation model. Interestingly, these mice also showed lower levels of anxiety when compared to wild type (Saegusa H., Kurihara T., Zong S., Kazuno A., Matsuda Y. Nonaka T., Han W., Toriyama H., Tanabe T., EMBO J. (2001) 20: 2349-2356). The involvement of N-type calcium channels in pain has been further validated in the clinic by ziconotide, a peptide derived from the venom of the marine snail, *Conus Magnus*. A limitation in the therapeutic use of this peptide is that it has to be administered intrathecally in humans (Bowersox S. S, and Luther R. Toxicon, (1998) 36: 1651-1658).

Sodium channels play an important role in the neuronal network by transmitting electrical impulses rapidly throughout cells and cell networks, thereby coordinating higher processes ranging from locomotion to cognition. These channels are large transmembrane proteins, which are able to switch between different states to enable selective permeability for sodium ions. For this process an action potential is needed to depolarize the membrane, and hence these channels are voltage-gated. In the past few years a much better understanding of sodium channels and drugs interacting with them has been developed.

Voltage-gated sodium channels were originally classified based on their sensitivity to tetrodotoxin, from low nanomolar (Tetrodotoxin sensitive, TTXs) to high micromolar (Tetrodotoxin resistant, TTXr). So far, 10 different sodium channel α subunits have been identified and classified as Nav1.1 to Nav1.9. Nav1.1 to Nav1.4, Nav1.6 and Nav1.7 are TTXs, whereas Nav1.5, Nav1.8 and Nav.1.9 are TTXr, with different degrees of sensitivity. Nav1.1 to Nav1.3 and Nav1.6, are primarily expressed in the CNS, whereas Nav1.4 and Nav1.5 are mainly expressed in muscle (skeletal and heart respectively) and Nav1.8 and Nav1.9 are predominantly expressed in small DRGs.

It has become clear that a number of drugs having an unknown mechanism of action actually act by modulating sodium channel conductance, including local anaesthetics, class I antiarrhythmics and anticonvulsants. Neuronal sodium channel blockers have found application with their use in the treatment of epilepsy (phenyloin and carbamazepine), bipolar disorder (lamotrigine), preventing neurodegeneration, and in reducing neuropathic pain. Various anti-epileptic drugs that stabilize neuronal excitability are effective in neuropathic pain (gabapentin, carbamazepine).

In addition, an increase in sodium channel expression or activity has also been observed in several models of inflammatory pain, suggesting a role of sodium channels in inflammatory pain.

All together these findings indicate that compounds with sodium and/or calcium channel blockade have a high therapeutic potential in preventing, alleviating and curing a wide range of pathologies, including neurological, psychiatric, cardiovascular, urogenital and gastrointestinal diseases, where the above mechanisms have been described as playing a pathological role.

There are many papers and patents which describe sodium channel and/or calcium channel modulators or antagonists for the treatment or modulation of a plethora of disorders, such as their use as local anaesthetics, antiarrhythmics, antiemetics, antimanic anti-depressants, agents for the treatment of unipolar depression, cardiovascular diseases, urinary incontinence, diarrhoea, inflammation, epilepsy, neurodegenerative conditions, nerve cell death, neuropathic pain, migraine, acute hyperalgesia and inflammation, renal disease, allergy, asthma, bronchospasm, dysmenorrhea, esophageal spasm, glaucoma, urinary tract disorders, gastrointestinal motility disorders, premature labour, obesity.

A non-exhaustive list of such papers and patents/patent applications describing sodium and/or calcium channels blockers and uses thereof includes the references shown below.

C. Alzheimer describes in Adv. Exp. Med. Biol. 2002, 513, 161-181, sodium and calcium channels as targets of neuroprotective substances.

Vanegas e Schaible (Pain 2000, 85, 9-18) discuss effects of antagonists of calcium channels upon spinal mechanisms of pain, hyperalgesia and allodynia.

U.S. Pat. No. 5,051,403 relates to a method of reducing neuronal damage associated with an ischemic condition, such as stroke, by administration of binding/inhibitory omega-conotoxin peptide wherein the peptide is characterized by specific inhibition of voltage-gated calcium channel currents selectively in neuronal tissues.

U.S. Pat. No. 5,587,454 relates to compositions and methods of producing analgesia particularly in the treatment of pain and neuropathic pain.

U.S. Pat. No. 5,863,952 relates to calcium channel antagonists for the treatment of ischaemic stroke.

U.S. Pat. No. 6,011,035 relates to calcium channel blockers, useful in the treatment of conditions such as stroke and pain.

U.S. Pat. No. 6,117,841 relates to calcium channel blockers and their use in the treatment of stroke, cerebral ischemia, pain, head trauma or epilepsy.

U.S. Pat. No. 6,362,174 relates to N-type calcium channel blockers in the treatment of stroke, cerebral ischemia, pain, epilepsy, and head trauma.

U.S. Pat. No. 6,380,198 concerns the use of the calcium channel blocker flunarizine for the topical treatment of glaucoma.

U.S. Pat. No. 6,420,383 and U.S. Pat. No. 6,472,530 relate to novel calcium channel blockers, useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

U.S. Pat. No. 6,458,781 relates to compounds that act to block calcium channels and their use to treat stroke, cerebral ischemia, pain, head trauma or epilepsy.

U.S. Pat. No. 6,521,647 relates to the use of calcium channel blockers in the treatment of renal disease in animals, especially chronic renal failure.

WO 97/10210 relates to tricyclic heterocyclic derivatives, and their use in therapy, in particular as calcium channel antagonists, e.g. for the treatment of ischaemia, in particular ischaemic stroke.

WO 03/018561 relates to quinoline compounds as N-type calcium channel antagonists and methods of using such compounds for the treatment or prevention of pain or nociception.

WO 03/057219 relates to sodium channel blockers useful as agents for treating or modulating a central nervous system disorder, such as neuropathic pain, inflammatory pain, inflammation-related pain or epilepsy.

WO99/14199 discloses substituted 1,2,3,4,5,6-hexahydro-2,6-methano-3-benzazocines-10-oles as potent sodium channel blockers useful for the treatment of several diseases, such as stroke, neurodegenerative disorders, Alzheimer's Disease, Parkinson's Disease and cardiovascular disorders.

WO01/74779 discloses new aminopyridine sodium channel blockers and their use as anticonvulsants, local anesthetics, as antiarrythmics, for the treatment or prevention of neurodegenerative conditions, such as amyotrophic lateral sclerosis (ALS), for the treatment or prevention of both, acute or chronic pain, and for the treatment or prevention of diabetic neuropathy.

WO04/087125 discloses amino acid derivatives as inhibitors of mammalian sodium channels, useful in the treatment of chronic and acute pain, tinnitus, bowel disorders, bladder dysfunction and demyelinating diseases.

Monoamine oxidase (MAO) is an enzyme present in the outer mitochondrial membrane of neuronal and non-neuronal cells. Two isoforms of MAO exist: MAO-A and MAO-B. MAO enzymes are responsible for the oxidative deamination of endogenous and xenobiotic amines, and have a different substrate preference, inhibitor specificity, and tissue distribution. For MAO-A serotonin, noradrenaline and adrenaline are preferential substrates, and clorgyline is a selective MAO-A inhibitor; whereas MAO-B prefers β-phenylethylamine as a substrate, and is almost selectively inhibited by selegiline. Dopamine, tyramine and tryptamine are oxidized by both MAO-A and MAO-B, in particular in human brain dopamine is deaminated by 80% by MAO-B.

MAO inhibition allows endogenous and exogenous substrates to accumulate and may thereby, when almost fully inhibited (>90%), alter the dynamics of regular monoamine transmitters. MAO regulate the concentrations in the brain of the most important neurotransmitters such as noradrenaline, serotonin and dopamine which are related to emotion, anxiety and movement. Thus, it is thought that MAO be closely linked to various psychiatric and neurological disorders such as depression, anxiety and Parkinson's disease (PD).

MAO-A inhibitors are mainly used in psychiatry for the treatment of major, refractory and atypical depression as a consequence of their ability to increase the reduced serotonin and noradrenalin brain levels. More recently, MAO-A inhibitors have been used to treat patients with anxiety disorders such as social phobia, panic disorders, post-traumatic stress disorders and obsessive compulsive disorders.

MAO-B inhibitors are mainly used in neurology for the treatment of PD.

There is also recent evidence and interest in the role of MAO-B in other pathological conditions such as Alzheimer disease (AD). So far no evidence have been reported on MAO-B involvement in the metabolism of co-transmitters, such as colecystokinin, substance P, somatostatin and neurotensin, which are involved in the modulation of pain sensation. For this reason there is no scientific rationale for the use of MAO-B inhibitors in pain syndromes. Adverse drug reactions during clinical practice with MAO inhibitors have been reported. First generation of non-selective and irreversible MAO inhibitors, such as tranylcypromide and phenelzine, have serious side effects, including hepatotoxicity, orthostatic hypotension and most importantly hypertensive crisis that occurs following the ingestion of foods containing tyramine (Cooper A J.-Tyramine and irreversible monoamine oxidase inhibitors in clinical pratice.—*Br J Psych Suppl* 1989:38-45).

When these non-selective and irreversible MAO inhibitors are used, a strict tyramine-reduced diet must be observed. The pressor sensitivity towards tyramine is normalized 4 weeks after cessation of tranylcypromine therapy and more than 11 weeks after cessation of phenelzine therapy.

Selegiline, a almost selective and irreversible MAO-B inhibitor, especially when used in combination with levodopa, can cause anorexia/nausea, dry mouth, dyskinesia and orthostatic hypotension in patients with PD, the latter being most problematic (Volz H. P. and Gleiter C. H.—Monoamine oxidase inhibitors. A perspective on their use in the elderly.—*Drugs Aging* 13 (1998), pp. 341-355).

In monotherapy, anorexia/nausea, musculoskeletal injuries, and cardiac arrhytmias occurred more often in patients receiving selegiline compared with those receiving placebo. Apart from these adverse effects, increased rates of elevated serum AST and ALT levels were noted.

The most frequently reported adverse effect of moclobemide, a selective and reversible MAO-A inhibitor, are sleep disturbances, increased anxiety, restlessness, and headache.

The combination of selective serotonin reuptake inhibitors (SSRIs) and moclobemide has good efficacy in cases of refractory depression, but has created controversy as to whether toxic side effects, such as serotonergic syndrome, result from this combination (Baumann P.—Pharmacokinetic-pharmacodynamic relationship of the selective serotonin reuptake inhibitors. *Clin Pharmacokinet* 31 (1996), pp 444-469). Because of cardiac arrhythmias and increased liver enzyme levels, electrocardiogram and laboratory values should be checked regularly.

Many types of physiologic changes that occur with aging affect the pharmacodynamics and pharmacokinetics of MAO inhibitors. Indeed, pharmacokinetic variables in the elderly are markedly different form those in younger patients. These variables including absorption, distribution, metabolism and excretion have to be taken into account to avoid or minimize certain adverse effects and drug-drug interactions. Elderly patients are generally more susceptible than younger patients to side effects, including adverse drug reactions. Hypertensive crisis may occur more frequently in elderly than in younger patients, because cardiovascular systems of the elderly are already compromised by age.

The use of sympathomimetic drugs in combination with MAO inhibitors may also elevate blood pressure. In addition, compared with placebo, phenelzine was associated with a significantly higher incidence of drowsiness, tremor, dyskinesia, diarrhea, micturition difficulties, orthostatic effects, and adverse dermatological effects. It is interesting to note that in the elderly, headache is reported with a higher frequency than in younger patients during treatment with moclobemide (Volz H. P. and Gleiter C. H.—Monoamine oxidase inhibitors. A perspective on their use in the elderly. *Drugs Aging* 13 (1998), pp. 341-355).

MAO inhibitors are sometimes prescribed for depression. Because of the potential risk of suicide, adverse drug reactions and toxicity due to overdose are important factors to consider when choosing an antidepressant. In addition, when MAO inhibitors are used in high dosage, adverse cardiovascular effects seem to increase considerably; and because MAO selectivity is lost with such high doses, tyramine can induce potentially dangerous hypertensive reactions. Acute overdose with MAO inhibitors causes agitation, hallucinations, hyperpyrexia, hyperreflexia and convulsions. Abnormal blood pressure is also a toxic sign, so that gastric lavage and maintenance of cardiopulmonary function may be required. Overdose of traditional non-selective and irreversible MAO inhibitors are considerably dangerous and sometimes fatal (Yamada and Richelson, 1996. Pharmacology of antidepressants in the elderly. In: David J R, Snyder L., editors. Handbook of pharmacology of aging. Boca Raton: CRC Press 1996).

In the treatment of the affections wherein sodium and calcium channels mechanism(s) play(s) a pathological role and, in particular, of pain syndromes (either of neuropathic or inflammatory type) inhibition of MAO enzymes is of no benefits. The most clinically active anti-nociceptive drugs are devoid of MAO inhibition. On the contrary, MAO inhibitory side effects may impose at least two types of negative limitations.

1) Dietary: eating food with high tyramine content may cause severe, even life threatening increase of systemic blood pressure (the so called "cheese-effect").

2) Pharmacological: pain is often treated with a combination of drugs such as opioid derivatives and tricyclic antidepressant. With MAO inhibitors such association is dangerous as it may cause the serotoninergic syndrome (agitation, tremors, hallucination, hyperthermia and arrhythmias).

Thus, eliminating or significantly reducing MAO inhibitory activity in medicaments active as sodium and/or calcium channel modulators useful in preventing, alleviating and curing a wide range of pathologies where said mechanism(s) play(s) a pathological role, including neurological, psychiatric, cardiovascular, inflammatory, ophtalmic, urogenital and gastrointestinal diseases, is an unexpected and substantial therapeutic improvement versus compounds of similar efficacy but with the above mentioned side effects. Said improvement is particularly desirable for the medicaments active as sodium and/or calcium channel modulators useful, in particular, for the treatment of the pain syndromes.

Taken into account these findings on MAO inhibitors and, in particular, lacking any evidence on MAO-B role in pathological affections like pain, migraine, cardiovascular, inflammatory, urogenital and gastrointestinal diseases, it might be conceivable that MAO-B inhibition should not be an essential feature for compounds indicated for the above pathologies, avoiding any possible side effects during chronic and/or long-term treatments.

An advantageous solution to the above described problem would consist in providing medicaments which are "selectively active as sodium and/or calcium modulators" or a useful for the "selective treatment" of affections disorders or diseases wherein the sodium and/or calcium channel mechanism(s) play(s) a pathological role. With this expression are intended medicaments which, when administered to a patient in need thereof in amounts that are effective in the treatment of the above said affections wherein the above said mechanism(s) play(s) pathological role, do not exhibit any MAO inhibitory activity or exhibit a significantly reduced MAO inhibitory activity, thus resulting in avoidance of side effects due to accumulation of endogenous and exogenous monoamine transmitters.

It is a primary object of this invention the use of phenylethylamino derivatives for the manufacture of medicaments active as sodium and/or calcium channel modulators for the treatment of pathologies where the above said mechanism(s) play(s) a pathological role, said medicaments being substantially free from any MAO inhibitory activity or having significantly reduced MAO inhibitory activity and, therefore, having a reduced potential for unwanted side effects. Said use provides an improved selective resource for the prevention, alleviation and/or cure of the above said pathological affections.

DESCRIPTION OF THE INVENTION

Figure 1:
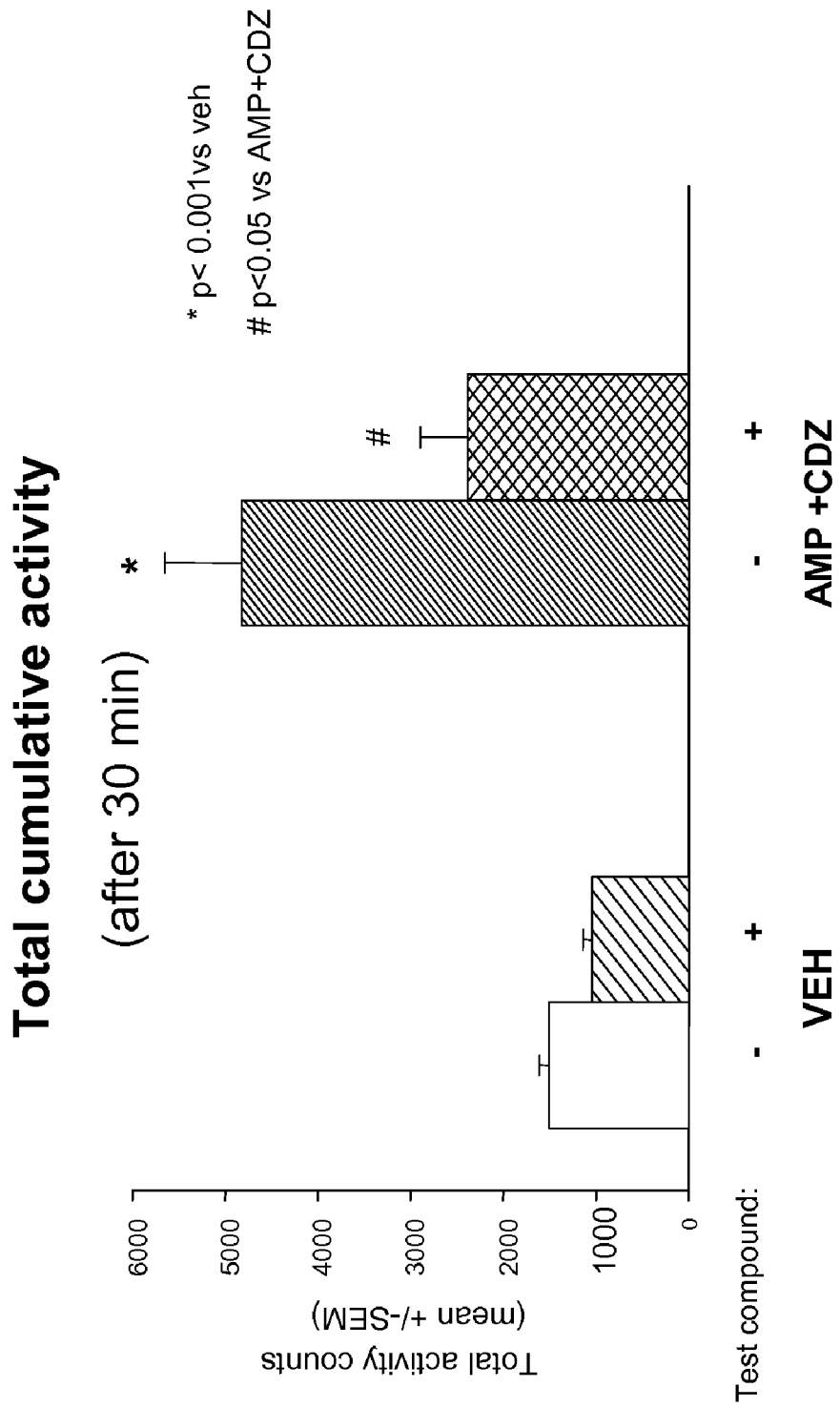
FIG. 1 shows the effect of the compound of 2-[[2-(3-Butoxy-phenyl)-ethyl]-(tetrahydrofuran-3-ylmethyl)amino]-N,N-dimethyl-acetamide hydrochloride in preventing the amphetamine-chlordiazepoxide induced increase in locomotor activity in mice.

We have now found a new class of phenylethylamino derivatives highly potent as sodium and/or calcium channel modulators and substantially free from any MAO inhibitory activity or having significantly reduced MAO inhibitory activity and, thus, having potentially reduced side effects in preventing, alleviating and curing a wide range of pathologies, including but not limited to neurogical, psychiatric, cardiovascular, inflammatory, ophthalmic, urogenital and gastrointestinal diseases where the above mechanisms have been described as playing a pathological role.

In this description and claims, the expression "sodium and/or calcium channel modulator(s)" means compounds able to block sodium and/or calcium currents in a voltage dependent manner.

Therefore, object of the present invention is a compound of general formula I

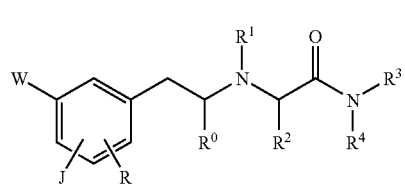

wherein:

(a)

J is a group A-[(CH$_2$)$_n$—O]$_r$— in para position with respect to the ethylamino chain wherein:
n is zero or 1; and
r is 1;
A is trifluomethyl; cyclopentyl; or phenyl optionally substituted with a halo group;
W is (C$_1$-C$_4$)alkoxy;
R is hydrogen;
R$^0$ is hydrogen; or (C$_1$-C$_2$)alkyl;
R$^1$ is hydrogen; (C$_1$-C$_4$)alkyl optionally substituted with a hydroxy group; cyclopropylmethyl; 2-propyn-1-yl; benzyl optionally substituted with one or two (C$_1$-C$_2$)alkoxy groups on the benzene ring; thiazolyl; a 5-6 membered saturated heterocyclyl containing a nitrogen atom, optionally substituted with a (C$_1$-C$_2$)alkyl group; or heterocyclylmethyl wherein the heterocyclyl group is a 5-6 membered heterocylyl containing 1 to 3 hetero atoms selected from nitrogen, oxygen and sulfur, optionally substituted with one or two groups selected from (C$_1$-C$_2$)alkyl, hydroxymethyl and (C$_1$-C$_2$)alkoxy;
R$^2$ is hydrogen; (C$_1$-C$_4$)alkyl; or phenyl;
R$^3$ is hydrogen; or (C$_1$-C$_4$)alkyl; and
R$^4$ is hydrogen; (C$_1$-C$_4$)alkyl optionally substituted with a group selected from amino, (C$_1$-C$_4$)alkylamino, di-(C$_1$-C$_4$)alkylamino, imidazolyl and pyrrolidinyl wherein the imidazolyl and the pyrrolidinyl group is optionally substituted with a (C$_1$-C$_2$)alkyl group; or benzyl; or
R$^3$ and R$^4$, taken together with the adjacent nitrogen atom, form a pyrrolidinyl, morpholinyl or piperazinyl ring optionally substituted with a (C$_1$-C$_2$)alkyl group; or (b)
J is a group A-[(CH$_2$)$_n$—O]$_r$— in para position with respect to the ethylamino chain wherein:
n is 1; and
r is 1;
A is phenyl; or phenyl substituted with a halo group;
W is hydrogen;
R is hydrogen;
R$^0$ is (C$_1$-C$_2$)alkyl;
R$^1$ is hydrogen;

$R^2$ is $(C_1-C_2)$alkyl;
$R^3$ is hydrogen; or $(C_1-C_4)$ alkyl; and
$R^4$ is hydrogen; or $(C_1-C_4)$alkyl; or (c)
J is hydrogen;
W is a group A-[(CH$_2$)$_n$—O]$_r$— wherein:
   n is zero, 1 or 2; and
   r is zero or 1;
   A is $(C_1-C_4)$alkyl, trifluoromethyl; cyclopropyl; cyclopentyl; phenyl optionally substituted with a group selected from halo, methyl, methoxy, trifluoromethyl, acetylamino, and dimethylaminomethyl; thienyl optionally substituted with a chloro group; furanyl; isoxazolyl optionally substituted with one or two methyl groups; piperidinyl; morpholinyl; pyridinyl or pyrimidinyl, the pyridinyl and pyrimidinyl ring being optionally substituted with one or two methoxy groups;
R is hydrogen; or fluoro;
$R^0$ is hydrogen; or $(C_1-C_2)$alkyl;
$R^1$ is isopropyl; cyclopropylmethyl; furanylmethyl; tetrahydrofuranyl; or tetrahydrofuranylmethyl;
$R^2$ is hydrogen; or $(C_1-C_4)$alkyl;
$R^3$ is hydrogen; or $(C_1-C_4)$alkyl; and
$R^4$ is hydrogen; $(C_1-C_4)$alkyl optionally substituted with a group selected from $(C_1-C_2)$alkoxy, amino, $(C_1-C_4)$alkylamino and di-$(C_1-C_4)$alkylamino; or heterocyclyl wherein the heterocyclyl is selected from isoxazolyl, pyrazolyl, imidazolyl, thiazolyl and 1,3,4 thiadiazolyl and may be optionally substituted with a $(C_1-C_2)$alkyl group; or
$R^3$ and $R^4$ taken together with the adjacent nitrogen atom form a pyrrolidine ring;

with the proviso that when A is $(C_1-C_4)$alkyl, trifluoromethyl, cyclopropyl or cyclopentyl, then r is 1; and with the further proviso that when $R^1$ is isopropryl, then A is trifluoromethyl and n is 1;

if the case, either as a single enantiomer or diastereoisomer or mixture thereof and its pharmaceutically acceptable salts.

The term "$(C_1-C_4)$alkyl" or the "$(C_1-C_4)$ alkyl" moiety in the other substitutents (e.g. in the terms alkoxy, mono and di-alkylamino) as used in this description and claims, when no otherwise specified, identifies a straight or branched alkyl radical or moiety; examples of said radicals or moieties include, respectively: methyl, ethyl, propyl, isopropyl, butyl, isobutyl and tert-butyl or methoxy, ethoxy, propoxy, isopropoxy, butoxy isobutoxy and tert-butoxy.

The term "halo", when no otherwise specified herein, means an halogen atom radical such as fluoro, chloro, bromo and iodo.

The term "heterocycle" and "heterocyclyl" when not otherwise specified herein, identifies a wholly unsaturated, a partially unsaturated or a saturated monocyclic 5 or 6 membered heterocyclic containing from 1 to 3 hetero atoms selected from nitrogen, oxygen and sulfur.

Examples of a monocyclic 5 or 6 membered wholly unsaturated heterocycle containing from 1 to 3 heteroatoms selected from nitrogen, oxygen and sulphur comprise, for instance, pyrrole, furan, thiophene, pyrazole, imidazole, isoxazole, oxazole, isothiazole, thiazole, 1,2,3 and 1,3,4 thiadiazole, pyridine, pyran, pyridazine, pyrimidine, pyrazine, and triazine. Examples of a monocyclic 5-6 membered partially unsaturated heterocycle containing 1 to 3 heteroatoms selected from nitrogen, oxygen and sulfur comprise, for instance, pyrroline, pyrazoline, imidazoline, oxazoline, isoxazolidine and thiazoline.

Examples of a monocyclic 5 or 6 membered saturated heterocycle containing from 1 to 3 heteroatoms selected among nitrogen, oxygen and sulphur comprise, for instance, pyrrolidine, pyrazolidine, imidazolidine, oxazolidine, isoxazolidine, piperidine, piperazine, tetrahydrofuran, tetrahydropyran, morpholine and thiomorpholine.

Where the compounds of this invention contain at least one asymmetric carbon atom they can exist as single enantiomers or diastereoisomers or a mixture thereof, the invention includes within its scope all the possible single enantiomers or diastereoisomers of said compounds and the mixtures thereof, e.g., the racemic mixtures.

Examples of pharmaceutically acceptable salts of the compounds of formula I are salts with organic and inorganic acids such as hydrochloric, hydrobromic, hydroiodic, nitric, sulfuric, phosphoric, acetic, propionic, tartaric, fumaric, citric, benzoic, succinic, cinnamic, mandelic, salicylic, glycolic, lactic, oxalic, malic, maleic, malonic, fumaric, tartaric, p-toluenesulfonic, methanesulfonic, glutaric acid and the like.

The compounds of formula I are active as calcium and/or sodium channel modulators and therefore useful in preventing alleviating and curing a wide range of pathologies, including but not limited to neurological, psychiatric, cardiovascular, inflammatory, ophthalmic, urologic and gastrointestinal diseases where the above mechanisms have been described as playing a pathological role.

A preferred group of compounds of formula I of this invention comprises a compound of group (a) defined above wherein:
J is a group A-[(CH$_2$)$_n$—O]$_r$— in para position with respect to the ethylamino chain wherein:
   n is 1; and
   r is 1;
   A is trifluoromethyl; cyclopentyl; phenyl; or phenyl substituted with a fluoro or chloro group;
W is methoxy;
R is hydrogen;
$R^0$ is hydrogen;
$R^1$ is hydrogen; $(C_1-C_4)$alkyl; hydroxyethyl; cyclopropylmethyl; 2-propin-1-yl; benzyl optionally substituted with one or two methoxy groups on the benzene ring; piperidinyl optionally substituted with a methyl group; thiazolyl; or heterocyclylmethyl wherein the heterocyclyl group is selected from isoxazolyl optionally substituted with a methyl or methoxy group, imidazolyl optionally substituted with a methyl group, furanyl optionally substituted with a hydroxymethyl group, tetrahydrofuranyl, 1,2,3-thiadiazolyl, pyrazolyl optionally substituted with one or two methyl groups, pyridinyl optionally substituted with a methoxy group, thienyl and thiazolyl;
$R^2$ is hydrogen; $(C_1-C_4)$alkyl; or phenyl;
$R^3$ is hydrogen; or $(C_1-C_4)$alkyl; and
$R^4$ is hydrogen; $(C_1-C_4)$alkyl optionally substituted with a group selected from amino, dimethylamino, imidazolyl and pyrrolidinyl wherein the pyrrolidinyl is optionally substituted with a methyl group; or benzyl; or
$R^3$ and $R^4$ taken together with the adjacent nitrogen atom form a pyrrolidinyl, piperazinyl or morpholinyl ring optionally substituted with a methyl group;

if the case, either as a single enantiomer or diastereoisomer or mixture thereof and its pharmaceutically acceptable salts.

A further group of preferred compounds of formula I of this invention comprises a compound of group (b) defined above wherein:

J is a group A-[(CH$_2$)$_n$—O]$_r$— in para position with respect to the ethylamino chain wherein:
  n is 1; and
  r is 1;
A is phenyl; or phenyl substituted with a fluoro or chloro group;
W is hydrogen;
R is hydrogen;
R$^0$ is methyl;
R$^1$ is hydrogen;
R$^2$ is methyl;
R$^3$ is hydrogen; or (C$_1$-C$_4$)alkyl; and
R$^4$ is hydrogen; or (C$_1$-C$_4$)alkyl;

if the case, either as a single enantiomer or diastereoisomer or mixture thereof and its pharmaceutically acceptable salts.

A further group of preferred compounds of formula I of this invention comprises those compounds of group (c) defined above wherein:
J is hydrogen;
W is a group A-[(CH$_2$)$_n$—O—]$_r$— wherein:
  n is zero, 1 or 2;
  r is zero or 1;
  A is (C$_1$-C$_4$)alkyl; trifluoromethyl; cyclopropyl; cyclopentyl; phenyl optionally substituted with a group selected from fluoro, chloro, methyl, methoxy, trifluoromethyl, acetylamino and dimethylaminomethyl; thienyl optionally substituted with a chloro group; furanyl; isoxazolyl optionally substituted with one or two methyl groups; piperidinyl; morpholinyl; pyridinyl or pyrimidinyl, the pyridinyl and pyrimidinyl group being optionally substituted with one or two methoxy groups;
R is hydrogen; or fluoro;
R$^0$ is hydrogen;
R$^1$ is cyclopropylmethyl; furanylmethyl; tetrahydrofuranyl; or tetrahydrofuranylmethyl;
R$^2$ is hydrogen; or methyl;
R$^3$ is hydrogen; or (C$_1$-C$_4$)alkyl; and
R$^4$ is hydrogen; (C$_1$-C$_4$)alkyl optionally substituted with a group selected from methoxy, amino, methylamino and dimethylamino; isoxazolyl optionally substituted with a methyl group; pyrazolyl; imidazolyl; thiazolyl; or 1,3,4 thiazolyl; or
R$^3$ and R$^4$ taken together with the adjacent nitrogen atom form a pyrrolidine ring;

with the proviso that when A is (C$_1$-C$_4$)alkyl, trifluoromethyl, cyclopropyl or cyclopentyl, then r is 1;

if the case, either as a single enantiomer or diastereoisomer or mixture thereof and its pharmaceutically acceptable salts.

A more preferred group of compounds of formula I encompassed by group (c) defined above comprises a compound wherein;
J is hydrogen;
W is a group A-[(CH$_2$)]$_n$—O]$_r$— wherein:
  n is 1 or 2;
  r is 1;
  A is (C$_1$-C$_4$)alkyl; trifluoromethyl; cyclopropyl; cyclopentyl; phenyl optionally substituted with a group selected from fluoro, chloro, methyl, methoxy, and trifluoromethyl; thienyl optionally substituted with a chloro group; isoxazolyl optionally substituted with one or two methyl groups; pyridinyl; piperidinyl; or morpholinyl;
R is hydrogen; or fluoro;
R$^0$ is hydrogen;
R$^1$ is cyclopropylmethyl; furanylmethyl; tetrahydrofuranyl; or tetrahydrofuranylmethyl;
R$^2$ is hydrogen;
R$^3$ is hydrogen; or (C$_1$-C$_4$)alkyl; and
R$^4$ is hydrogen; (C$_1$-C$_4$)alkyl optionally substituted with a group selected from methoxy, amino, methylamino and dimethylamino; isoxazolyl optionally substituted with a methyl group; pyrazolyl; imidazolyl; thiazolyl; or 1,3,4 thiazolyl; or
R$^3$ and R$^4$ taken together with the adjacent nitrogen atom form a pyrrolidine ring;

if the case, either as a single enantiomer or diastereoisomer or mixture thereof and its pharmaceutically acceptable salts.

Among this group of more preferred compounds of formula I of the group (c) herein above defined a most preferred group of compounds comprises a compound wherein:
J is hydrogen;
W is a group A-[(CH$_2$)$_n$—O]$_r$— wherein:
  n is 1;
  r is 1;
  A is (C$_1$-C$_4$)alkyl;
R is hydrogen;
R$^0$ is hydrogen;
R$^1$ is furanylmethyl; or tetrahydrofuranylmethyl;
R$^2$ is hydrogen;
R$^3$ is hydrogen; or (C$_1$-C$_4$)alkyl; and
R$^4$ is (C$_1$-C$_4$)alkyl;

either as a single enantiomer or, if the case, diastereoisomer, or mixture thereof and its pharmaceutically acceptable salts.

A further more preferred group of compounds of formula I encompassed by the group (c) defined above comprises a compound wherein:
J is hydrogen;
W is a group A-[(CH$_2$)$_n$—O]$_r$— wherein:
  n is zero;
  r is 1;
  A is cyclopentyl; or phenyl optionally substituted with a fluoro group;
R is hydrogen;
R$^1$ is furanylmethyl;
R$^2$ is hydrogen;
R$^3$ is hydrogen; or (C$_1$-C$_4$)alkyl; and
R$^4$ is hydrogen; or (C$_1$-C$_4$)alkyl;

if the case, either as a single enantiomer or diastereoisomer or mixture thereof and its pharmaceutically acceptable salts.

A further more preferred group of compounds of formula I encompassed by the group (c) defined above comprises a compound wherein:
J is hydrogen;
W is a group A-[(CH$_2$)$_n$—O]$_r$— wherein:
  n is zero;
  r is zero;
  A is phenyl optionally substituted with a group selected from fluoro, methoxy, acetylamino and dimethylaminomethyl; thienyl; furanyl; isoxazolyl optionally substituted with one or two methyl groups; piperidinyl; pyridinyl or pyrimidinyl, the pyridinyl and pyrimidinyl group being optionally substituted with one or two methoxy groups;
R is hydrogen;
R$^0$ is hydrogen;
R$^1$ is furanylmethyl; or tetrahydrofuranylmethyl;
R$^2$ is hydrogen;
R$^3$ is hydrogen; or (C$_1$-C$_4$)alkyl; and
R$^4$ is hydrogen; or (C$_1$-C$_4$)alkyl;

if the case, either as a single enantiomer or diastereoisomer or mixture thereof and its pharmaceutically acceptable salts.

Most preferably, a compound of formula I according to this invention is selected from the group consisting of:

2-[2-[4-(3-Fluoro-benzyloxy)-3-methoxy-phenyl]-ethylamino]-N-methyl-acetamide;
2-[[2-[4-(3-Fluoro-benzyloxy)-3-methoxy-phenyl]-ethyl]-isobutylamino]-N-methyl-acetamide;
2-[[2-[4-(3-Fluoro-benzyloxy)-3-methoxy-phenyl]-ethyl]-(tetrahydrofuran-3-ylmethyl)amino]-N-methyl-acetamide;
2-[2-[4-(3-Fluoro-benzyloxy)-3-methoxy-phenyl]-ethylamino]-N,N-dimethyl-acetamide;
2-[[2-[4-(3-Fluoro-benzyloxy)-3-methoxy-phenyl]-ethyl]-benzylamino]-N,N-dimethyl-acetamide;
2-[2-[4-(3-Fluoro-benzyloxy)-3-methoxy-phenyl]-ethylamino]-N,N-dimethyl-propionamide;
2-[2-[4-(3-Fluoro-benzyloxy)-3-methoxy-phenyl]-ethylamino]-N,N-dimethyl-2-phenyl-acetamide;
2-[2-[4-(3-Fluoro-benzyloxy)-3-methoxy-phenyl]-ethylamino]-1-(morpholin-4-yl)-2-phenyl-ethanone;
2-[[2-[4-(3-Fluoro-benzyloxy)-3-methoxy-phenyl]-ethyl]-benzylamino]-acetamide;
2-[[2-[4-(3-Fluoro-benzyloxy)-3-methoxy-phenyl]-ethyl]-benzylamino]-1-(pyrrolidin-1-yl)ethanone;
2-[[2-[4-(3-Fluoro-benzyloxy)-3-methoxy-phenyl]-ethyl]-benzylamino]-N-(2-amino-2-methylpropyl)-acetamide;
2-[[2-[4-(3-Fluoro-benzyloxy)-3-methoxy-phenyl]-ethyl]-benzylamino]-N-(2-dimethylaminoethyl)-acetamide;
2-[[2-[4-(3-Fluoro-benzyloxy)-3-methoxy-phenyl]-ethyl]-benzylamino]-N-[2-(1-methyl-pyrrolidin-2-yl)-ethyl]-acetamide;
2-[[2-[4-(3-Fluoro-benzyloxy)-3-methoxy-phenyl]-ethyl]-(cyclopropylmethyl)amino]-N-ethylacetamide;
2-[[2-[4-(Benzyloxy)-3-methoxy-phenyl]-ethyl]-(cyclopropylmethyl)amino]-N-methylacetamide;
2-[[2-(3-Benzyloxy-phenyl)-ethyl]-(cyclopropylmethyl)amino]-N-methyl-acetamide;
2-[[2-(3-Benzyloxy-phenyl)-ethyl]-(furan-2-ylmethyl)amino]-N-methyl-acetamide;
2-[[2-[3-(2-Fluoro-benzyloxy)-phenyl]-ethyl]-(furan-2-ylmethyl)amino]-N-methyl-acetamide;
2-[[2-[3-(3-Fluoro-benzyloxy)-phenyl]-ethyl]-(furan-2-ylmethyl)amino]-acetamide;
2-[[2-[3-(3-Fluoro-benzyloxy)-phenyl]-ethyl]-(furan-2-ylmethyl)amino]-N-(2-dimethylaminoethyl)-acetamide;
2-[[2-[3-(3-Fluoro-benzyloxy)-phenyl]-ethyl]-(furan-2-ylmethyl)amino]-N-(2-amino-2-methylpropyl)-acetamide;
2-[[2-[3-(2,2,2-Trifluoro-ethoxy)-phenyl]-ethyl]-isopropylamino]-N,N-dimethyl-acetamide;
2-[[2-(3-Benzyloxy-phenyl)-ethyl]-(cyclopropylmethyl)amino]-N-methyl-propionamide;
2-[[2-[3-Methoxy-4-(2,2,2-trifluoro-ethoxy)-phenyl]-ethyl]-(cyclopropylmethyl)amino]-N-methyl-acetamide;
2-[[2-(3'-Fluoro-biphenyl-3-yl)-ethyl]-(furan-2-ylmethyl)amino]-N-methyl-acetamide;
2-[[2-(3-Benzyloxy-phenyl)-ethyl]-(tetrahydrofuran-3-ylmethyl)amino]-N,N-dimethyl-acetamide;
2-[[2-[(3-Butoxy-phenyl)]-ethyl]-(tetrahydrofuran-3-ylmethyl)amino]-N,N-dimethyl-acetamide;
2-[[2-(3-Butoxy-phenyl)-ethyl]-(furan-2-ylmethyl)amino]-N-methyl-acetamide hydrochloride
2-[[2-[4-Fluoro-3-(2,2,2-trifluoro-ethoxy)-phenyl]-ethyl]-(tetrahydrofuran-3-ylmethyl)amino]-N,N-dimethyl-acetamide;
2-[[2-[3-(2,2,2-Trifluoro-ethoxy)-phenyl]-ethyl]-(tetrahydrofuran-3-yl)amino]-N,N-dimethyl-acetamide;
2-[[2-[3-(3,5-Dimethyl-isoxazol-4-yl)-phenyl]-ethyl]-(tetrahydrofuran-3-yl)amino]-N,N-dimethyl-acetamide;
2-[[2-(3-Piperidin-1-yl-phenyl)-ethyl]-(tetrahydrofuran-3-ylmethyl)amino]-N,N-dimethyl-acetamide;
(2S)-2-[2-[(4-Benzyloxy)-phenyl]-1-methyl-ethylamino]-propionamide;
2-[[2-[4-(3-Fluoro-benzyloxy)-3-methoxy-phenyl]-ethyl]-(cyclopropylmethyl)amino]-N-methyl-acetamide;
(S)-2-[2-[4-(3-Fluoro-benzyloxy)-3-methoxy-phenyl]-ethylamino]-N-methyl-4-methyl-valeramide;
2-[[2-[4-(3-Fluoro-benzyloxy)-3-methoxy-phenyl]-ethyl]-(furan-3-ylmethyl)amino]-N-methylacetamide;
2-[[2-[4-(3-Fluoro-benzyloxy)-3-methoxy-phenyl]-ethyl]-benzylamino]-N-ethyl-acetamide; and
2-[[2-[4-(3-Fluoro-benzyloxy)-3-methoxy-phenyl]-ethyl]-(6-methoxy-pyridin-3-ylmethyl)amino]-N-methyl-acetamide;

if the case, either as a single enantiomer or diastereoisomer or mixture thereof and its pharmaceutically acceptable salts, preferably its salt with hydrochloric acid.

The compounds of formula I, object of the present invention, are prepared according to a synthetic process which comprises:

a) the reaction of a compound of formula II

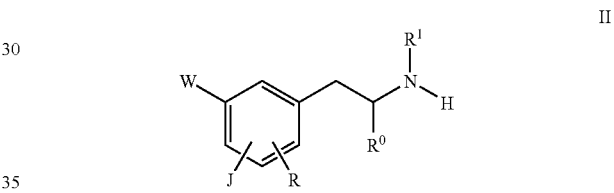

wherein

J, W, R, R⁰, and R¹, have the same meanings defined in formula I above, with a compound of formula III

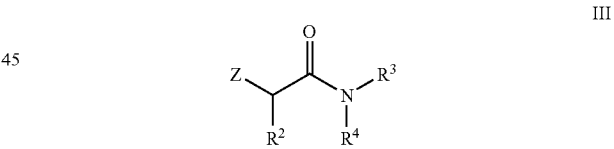

wherein $R^2$, $R^3$ and $R^4$ have the same meanings as defined in formula I above and Z is a halogen atom or a good leaving group such as, for example, methanesulfonyloxy, p-toluenesulfonyloxy or trifluoromethanesulfonate groups; or said reaction is alternatively carried out between a compound of formula II and a compound of formula IV

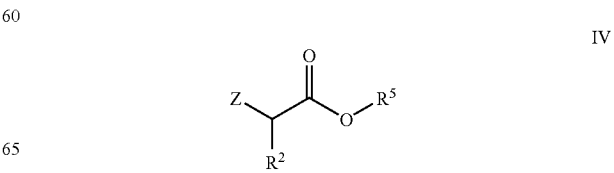

wherein

R² and Z have the meanings defined above and R⁵ is a (C₁-C₄)alkyl group, to give a compound of formula V

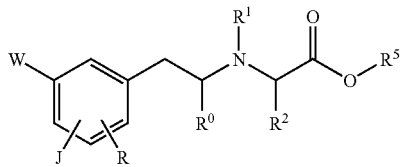

wherein

J, W, R, R⁰, R¹, R², and R⁵, and have the same meanings as defined above; which is further reacted with an amine of formula HNR³R⁴ where R³ and R⁴ are as defined above, to give the compounds of the invention.

The amidation reaction which allows the introduction of the substituent —NR³R⁴ is carried out according to conventional amidation techniques whereby an ester is converted to the corresponding amide by reaction with the selected amine. According to a practical embodiment of the invention the amidation is carried out in the presence of trimethylaluminium.

The compound of formula I wherein J, W, R, R⁰, R², R³, and R⁴ have the same meanings as above and R¹ has the same meanings as above, apart from hydrogen, can be prepared also through the reaction of a compound of formula VI

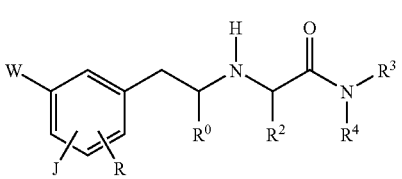

wherein

J, W, R, R⁰, R², R³, and R⁴, have the same meanings as in formula I above, with a compound R¹-Z, wherein R¹ has the meanings reported above apart from hydrogen and Z is a halogen atom or a good leaving group, e.g. methanesulfonyloxy, p-toluenesulfonyloxy or trifluoromethanesulfonyloxy in the presence of a base or with a carbonyl compound of the formula R⁶R⁷CO in the presence of a reducing agent, wherein R⁶ is: hydrogen; a (C₁-C₃)alkyl optionally substituted with a hydroxy group; cyclopropyl; ethynyl; phenyl optionally substituted with one or two (C₁-C₂)alkoxy groups; a 5 or 6 membered heterocyclyl containing from 1 to 3 heteroatoms selected from nitrogen, oxygen and sulphur, where the heterocyclyl is optionally substituted with one or two groups selected from (C₁-C₂)alkyl, hydroxymethyl and (C₁-C₂) alkoxy; R⁷ is hydrogen; or R⁶ and R⁷ taken together with the adjacent carbonyl group represent a (C₃-C₄)aliphatic, ketone or a 5-6 membered saturated heterocyclic ketone containing a nitrogen or a oxygen atom optionally substituted with a (C₁-C₂)alkyl group, e.g. 1-methyl-piperidin-4-one or dihydrofuran-3(2H)-one.

A compound of the invention may be converted into another compound of the invention. For instance, a compound of formula I wherein J represents a benzyloxy radical may be transformed into the corresponding hydroxy-derivative by catalytic hydrogenation and then reacted with an appropriate reagent to replace the original benzyl moiety with a different group, e.g., a trifluoromethylbenzyl, phenylethyl, trifluoroethyl, cyclopentyl, cyclopropylmethyl and heterocyclymethyl group as defined above. If desired, a compound of the invention may be converted into a pharmaceutically acceptable salt and/or, if desired, a salt may be converted into a free compound and/or, if desired, a mixture of enantiomers or diastereoisomers of compounds of the invention may be separated into the corresponding single isomers.

The compounds of formula II, III, IV and VI are commercially available or are prepared from commercially available compounds according to well-known methods.

According to a practical embodiment of the invention the preparation of a compound of formula II is carried out by reacting a compound of formula VII

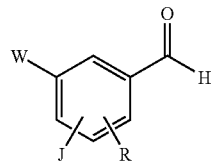

wherein

J, W, and R, have the meanings defined in formula I, with a nitroalkane of the formula R⁰—CH₂—NO₂ wherein R⁰ has the same meanings defined in formula I to give a compound of formula VIII

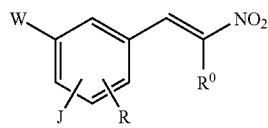

wherein

J, W, R, and R⁰ have the same meanings as in formula I, which is reduced with a reducing agent such as LiAlH₄ or by catalytic reduction using Pt/H₂ or Pd/H₂ to give a compound of formula II wherein R¹ is hydrogen.

When it is desired a compound of formula II wherein R¹ has the same meanings as above apart from hydrogen, the compound of formula II wherein R¹ is hydrogen is reacted with a compound of formula R¹Z wherein R¹ has the same meanings as above apart from hydrogen, in the presence of a base, or with a carbonyl compound of formula R⁶R⁷CO wherein R⁶ and R⁷ have the same meanings as defined above, in the presence of a reducing agent.

The reaction between a compound of formula II and a compound of formula III to give a compound of the invention is carried out according to known methods.

According to a preferred embodiment of the invention said reaction is carried out in the presence of a base and, more preferably, said base is selected from K₂CO₃, triethylamine or diisopropylethylamine.

When a compound of formula I is obtained wherein R¹ is hydrogen (i.e., a compound of formula VI) the introduction of a radical R¹ which is other than hydrogen defined above is carried out according to conventional methods for the preparation of secondary or tertiary amines such as alkylation or reductive amination techniques.

According to a preferred embodiment of the invention said alkylation reaction is carried out in the presence of a base and, more preferably, said base is selected from $K_2CO_3$, triethylamine and diisopropylethylamine.

According to another preferred embodiment of the invention said reductive amination with a compound $R^6R^7CO$, wherein $R^6$ and $R^7$ have the same meanings as defined above is carried out in the presence of a reducing agent selected from $NaBH_4$, $NaBH_3CN$ and (polystyrylmethyl)trimethylammonium cyanoborohydride.

As an alternative method, the compounds of formula I are prepared according to a synthetic process which comprises the reaction of a compound of formula IX

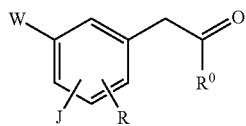

wherein

J, W, R, and $R^0$ have the same meanings as defined in formula I, or a compound of formula X

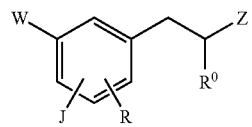

wherein

J, W, R, and $R^0$ have the same meanings as defined in formula I and Z is as defined above; with a compound of formula XI

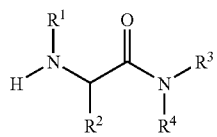

wherein $R^1$, $R^2$, $R^3$ and $R^4$ have the meanings defined in formula I in the presence of a reducing agent in the case of the reaction of IX with XI or a base in the case of the reaction between X and XI.

The reaction between a compound of formula IX and a compound of formula XI to give a compound of the invention is a reductive amination and the reaction of a compound of formula X with a compound of formula XI is an alkylation reaction: these reactions are carried out according to conventional techniques.

Preferred reducing agents used in the reaction between the compound of formula IX and XI are selected from $NaBH_4$, $NaBH_3CN$ and (polystyrylmethyl)-trimethylammonium cyanoborohydride.

According to a preferred embodiment of the invention the reaction between the compound of formula X and XI is carried out in the presence of a base and, more preferably, said base is selected from $K_2CO_3$, triethylamine or diisopropylethylamine.

In the preparation of the compounds of formula I and the starting materials and/or intermediates described herein it may be useful to protect certain groups which are sensitive to the reaction conditions.

The evaluation of the usefullness of the optional protection, as well as the selection of the suitable protecting agent, according to the reaction carried out in the preparation of the compounds of the invention and the functional group to be protected, are within the common knowledge of the skilled person.

The removal of the optional protective groups is carried out according to conventional techniques.

For a general reference to the use of protective groups in organic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods.

For the preparation of a single enantiomers or diastereoisomers, if the case, of a compound of formula I, said compound may be obtained through a sterically controlled synthesis or by using reagents having the appropriate chirality or separating the desired isomer from the enantiomeric or diastereoisomeric mixture thereof according to conventional procedures. For instance, single optically active enantiomers may be obtained from their racemates by chiral chromatography or by converting them into a mixture of diastereoisomeric derivatives, separating the diastereoisomeric derivatives and restoring the respective enantiomers.

Diastereoisomers can be separated from their mixtures by means of conventional techniques based on their different physico-chemical properties, such as chromatography, distillation, or fractional crystallization.

Pharmacology

The compounds of the invention may be used for the manufacture of a medicament active as calcium and/or sodium channel modulator against disorders caused by dysfunctions of voltage gated calcium and/or sodium channels.

The activity of the compounds representative of this invention was compared with that of our internal standard "ralfinamide" (S)-(+)-2-[4-(2-fluoro-benzyloxy)-benzylamino]-propanamide and/or "safinamide" (S)-(+)-2-[4-(3-fluoro-benzyloxy)-benzylamino]-propanamide.

Such compounds are voltage-dependent blockers of the calcium and/or sodium channels with potencies in the low micromolar range as demonstrated by the blockade of the calcium and/or sodium influx (fluorescence assays) and by the voltage-dependent blockade of the currents (patch clamp techniques). The N-type and L-type calcium channel modulating activity of the phenylethylamino derivatives was measured through a fluorescence-based calcium influx assays (Table 1 for N-type and Table 2 for L-type) and through patch clamp techniques in constitutive and/or Cav 2.2 transfected cell lines (Table 4).

The sodium channel modulating activity of the phenylethylamino derivatives was measured through a fluorescence-based sodium influx assay (Table 3), through patch clamp techniques in constitutive and/or Nav 1.3 transfected cell lines (Table 5) and in cortical neurons (Table 6).

The MAO-B activity of the above compounds was measured by using a radioenzymatic assay (Table 7).

The in vivo analgesic activity of the above compounds was assessed in the "rat complete Freund's adjuvant model" and in the "Bennett model of neuropathic pain in rats" (Table 8).

The anticonvulsant activity was measured using the "Maximal electroshock test" in mice (Table 9).

The anti mania activity was measured using the "Amphetamine and chlordiazepoxide-induced hyperlocomotion in mice" model (FIG. 1).

The anti-schizophrenia and anti-addiction activities were assessed using the "test of cognitive impairment in schizophrenia" (Table 10) and the "Cocaine-induced behavioural sensitization test" in rats.

"Acute bladder irritation by acetic acid in rats" and "Intermediate bladder irritation by cyclophosphamide in rats" tests were used as models for urological diseases.

The anti migraine activity was measured using the "migraine test" in rats.

Such substances exhibit also "use and frequency-dependency", i.e. an enhancement of the block during a high frequency stimulation when there is a large accumulation of channels in the inactivated state, such as in neuronal pathological conditions. Functionally, the usedependent block results in depression of neuronal activity at high frequency firing and with lower blocking capacity at normal firing rate suggesting that the compounds of this invention may selectively depress abnormal activity of the calcium and/or sodium channels, leaving unaffected the physiological activity, thus decreasing CNS depressant effects (W. A. Catterall, Trends Pharmacol. Sci. (1987) 8: 57-65).

The compounds of the invention are active in vivo when orally or intraperitoneally administered in the range of 0.1 to 100 mg/kg in different animal models here following described.

In view of the above described mechanisms of action, the compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and pripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain (caused by acute injury, illness, sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

The compounds of the invention are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

The compounds of the invention are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure. The compounds of the invention are also useful for the treatment of neurodegenerative disorders of various origins such as Alzheimer Disease and other dementia conditions such as Lewys body, fronto-temporal dementia and taupathies; amyotrophic lateral sclerosis, Parkinson Disease and other parkinsonian syndromes; other spino cerebellar degeneration and Charcot-Marie-Toot neuropathy.

The compounds of the invention are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

Compounds of the invention are also useful in the treatment of diseases such as vertigo, tinnitus, muscle spasm, muscular sclerosis, and other disorders including and not limited to cardiovascular diseases (such as cardiac arrhythmia, cardiac infarction or angina pectoris, hypertention, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds of the invention are also useful in the selective treatment of liver disease, such as inflammatory liver diseases, for example chronic viral hepatitis B, chronic viral hepatitis C, alcoholic liver injury, primary biliary cirrhosis, autoimmune hepatitis, non-alcoholic steatohepatitis and liver transplant rejection.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gut, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, sclerodoma, myasthenia gravis, multiple sclerosis and other demyelinizating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyresis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartolinities and vaginitis. In particular overactive bladder and urinary incontinence.

The compounds of the invention are also useful in the treatment of ophthalmic diseases such as retinitis, retinopathies, uveitis and acute injury to the eye tissue, macular degeneration or glaucoma, conjunctivitis.

It will be appreciated that the compounds of the invention may advantageously be used in conjunction with one or more other therapeutic agents. Examples of suitable agents for adjunctive therapy include a serotonin receptor modulator including a 5HT1B/1D agonist, such as a triptan (e.g. sumatriptan or naratriptan); an adenosine A1 agonist; an adenosine A2 antagonist; a purinergic P2X antagonist, an EP ligand; an NMDA modulator, such as a glycine antagonist; an AMPA modulator; a substance P antagonist (e.g. an NK1 antagonist); a cannabinoid; a nicotinic receptor agonist; an alpha-1 or 2 adrenergic agonist; acetaminophen or phenacetin; a 5-lipoxygenase inhibitor; a leukotriene receptor antagonist; a DMARD (e.g. methotrexate); gabapentin and related compounds; L-dopa and/or dopamine agonists; a catechol-O-methyltransferase inhibitor; a tricyclic antidepressant (e.g. amitryptiline); a neurone stabilising antiepileptic drugs; a monoaminergic uptake inhibitor (e.g. venlafaxine); a matrix metalloproteinase inhibitor; a nitric oxide synthase (NOS) inhibitor, such as an iNOS or an nNOS inhibitor; a free radical scavenger; an alpha-synuclein aggregation inhibitor; a cholinesterase inhibitor, a cholesterol lowering agent; an alpha-secretase modulator; a betasecretase modulator; a beta-amyloid aggregation inhibitor; an inhibitor of the release, or action, of tumor necrosis factor alpha; an antibody therapy, such as monoclonal antibody therapy; an antiviral agent, such as a nucleoside inhibitor (e.g. lamivudine) or an immune system modulator (e.g. interferon); an opioid analgesic, such as morphine; a vanilloid receptor antagonist; an analgesic, such as a cyclooxygenase-1 and/or cyclooxygenase-2 inhibitor; a local anaesthetic such as lidocaine and derivatives; a stimulant, including caffeine; an H2-antagonist (e.g. ranitidine); a proton pump inhibitor (e.g. omeprazole); an antacid (e.g. aluminium or magnesium hydroxide; an antiflatulent (e.g. semethicone); a decongestant (e.g. phenylephrine, phenylpropanolamine, pseudoephedrine, oxymetazoline, epinephrine, naphazoline, xylometazoline, propylhexedrine, or levo-desoxyephedrine, naphazoline, xylometazoline, propylhexedrine, or levo-desoxyephedrine); antitussive (e.g. codeine, hydrocodone, carmiphen, carbetapentane, or dextramethorphan); a diuretic; or a sedating or non-sedating antihistamine; other calcium or sodium channel blockers. It is to be understood that the present invention covers the use of a compound of formula (I) or a pharmaceutically acceptable salt thereof in combination with one or more therapeutic agents.

The compounds of the present invention are useful in human and veterinary medicaments. It is to be understood that as used herein the terms "treatment" or "treating" whenever not specifically defined otherwise, include prevention, alleviation and cure of pathological affection, in particular, they include both treatment of established symptoms and prophylactic treatment. The compounds of the present invention for their therapeutic or preventive use in the above mentioned pathologies will be preferably used as active ingredients in a pharmaceutical composition.

Therefore, a further object of the present invention are pharmaceutical compositions containing a therapeutically effective amount of a compound of the invention or a salt thereof in admixture with a pharmaceutically acceptable carrier.

Accordingly, the expression "therapeutically effective" when referred to an "amount", a "dose" or "dosage" of the compounds of this invention is intended as an "amount", a "dose" or "dosage" of any said compounds sufficient for use in both treatment of the established symptoms and the prophylactic treatment of the above said pathological affections.

The pharmaceutical compositions object of the present invention may be administered in a variety of immediate and modified release dosage forms, e.g. orally, in the form of tablets, troches, capsules, sugar or film coated tablets, liquid solutions, emulsions or suspensions; rectally, in the form of suppositories; parenterally, e.g. by intramuscular and/or depot formulations; intravenous injection or infusion; locally and transdermally in form of patch and gel and cream.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils, cyclodextrins, polyalkyleneglycols and the like.

The composition comprising the phenylethylamino derivatives of formula I as above defined can be sterilized and may contain further well known components, such as, for example, preservatives, stabilizers, wetting or emulsifying agents, e.g. paraffin oil, mannide monooleate, salts to adjust osmotic pressure, buffers and the like.

For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disgregating agents, e.g. a starch, alginic acid, alginates or sodium starch glycolate;

effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The preparation of the pharmaceutical compositions object of the invention can be carried out according to common techniques.

The oral formulations comprise sustained release formulations that can be prepared in conventional manner, for instance by applying an enteric coating to tablets and granules.

The liquid dispersion for oral administration may be e.g. syrups, emulsions and suspensions.

The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactants or lecithin.

The pharmaceutical compositions comprising the phenylethylamino derivatives of formula I as above defined will contain, per dosage unit, e.g., capsule, tablet, powder injection, teaspoonful, suppository and the like from about 0.1 to about 500 mg of one or more active ingredients most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

It is to be understood that while the invention is described in conjunction of the preferred embodiments thereof, those skilled in the art are aware that other embodiment could be made without departing from the spirit of the invention.

Experimental Part

The $^1$H-NMR spectra have been stored in solution of CDCl$_3$ or DMSO-d$_6$ with a Varian Gemini 200 MHz spectrometer. The chemical shifts are defined as d with CDCl$_3$ or DMSO-d$_6$ and D$_2$O as inner standard.

The HPLC/MS analyses are stored with a Gilson instrument by utilizing a X-Terra RP18 column (5 μm, 4.6×50 mm) coupled to a UV detector (220 nm) and a Finnigan Aqa mass spectrometer (electron spray, positive ionization mode). Conditions utilized for the analyses: flow: 1.2 ml/min; column temperature: 50° C.; A/B elution gradient (eluent A: 0.1% formic acid in water; eluent B: 0.1% formic acid in acetonitrile): 5-95% of B from 0 to 8.0 minutes, 95% of B from 8.0 to 9.5 minutes.

For better illustrating the invention the following examples are now given.

EXAMPLES

Example 1

2-[2-[4-(3-Fluoro-benzyloxy)-3-methoxy-phenyl]-ethylamino]-N-methyl-acetamide hydrochloride The above compound was synthesized according to Scheme 1

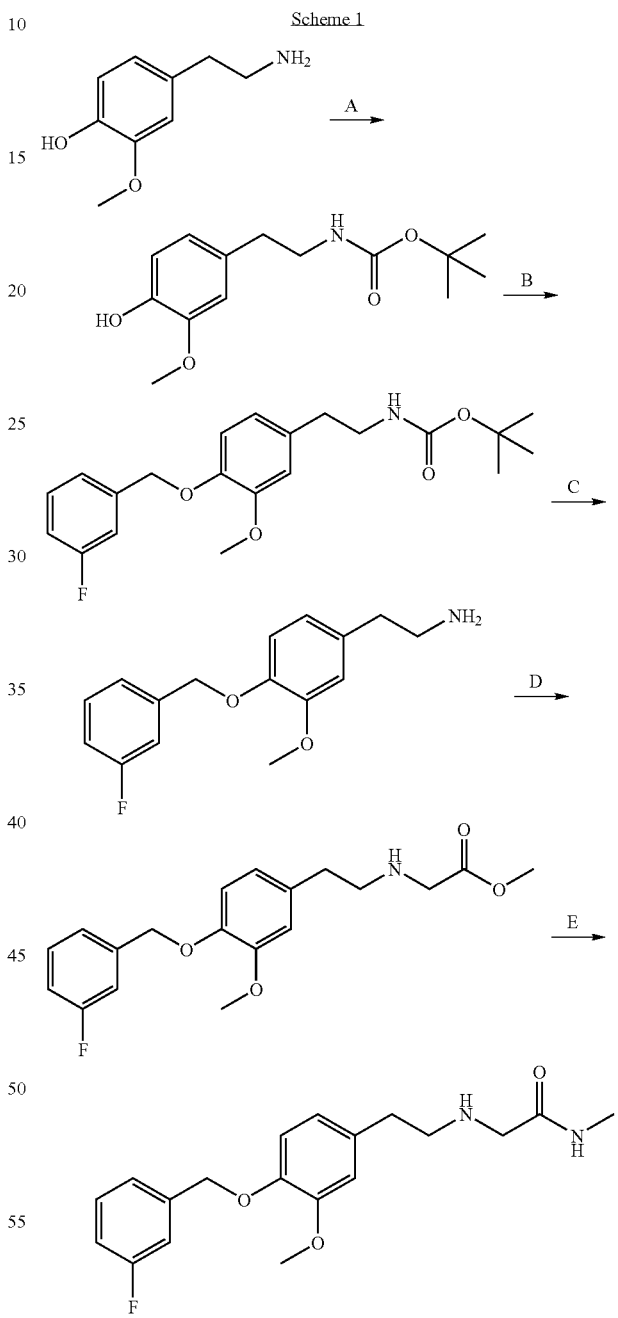

Step A
[2-(4-Hydroxy-3-methoxy-phenyl)-ethyl]-carbamic acid tert-butyl ester 54 g (0.24 mol) of (Boc)$_2$O dissolved in 100 ml of dioxane were added at 0° C. to a solution containing 39 g (0.23 mol) of 2-(4-hydroxy-3-methoxy-phenyl)-ethylamine in 230 ml of 1M sodium hydroxide and 390 ml of dioxane. The reaction was stirred at room temperature overnight. Dioxane was removed and aqueous $KHSO_4$ was added to the residue, until a pH value of 6 was reached. Extraction with ethyl acetate gave an oil that was triturated with hexane. 54.7 g (88% yield) of a white solid were obtained.

$^1$H-NMR $CDCl_3$: 7.26 (s, 1H); 6.88-6.64 (m, 2H); 5.51 (s, 1H); 4.54 (bs, 1H); 3.80 (s, 3H); 3.41-3.27 (m, 2H); 2.72 (t, 2H, J=7.25 Hz); 1.44 (s, 9H).

Step B [2-[4-(3-Fluoro-benzyloxy)-3-methoxy-phenyl]-ethyl]-carbamic acid tert-butyl ester 34.6 g (0.23 mol) of 1-chloromethyl-3-fluoro-benzene in 50 ml of dry dimethylformamide were added to a suspension of 55.9 g (0.209 mol) of [2-(4-hydroxy-3-methoxy-phenyl)-ethyl]-carbamic acid tert-butyl ester, 43 g of $K_2CO_3$ and 3.4 g of potassium iodide in 400 ml of dry dimethylformamide. The reaction was stirred at room temperature overnight. Solvent was removed, water was added to the residue and the product was extracted with ethyl acetate. The crude oil obtained was triturated with diethyl ether. The solid was filtered and 58.2 g (74% yield) of the title product were obtained.

$^1$H-NMR $CDCl_3$: 7.40-6.60 (m, 7H); 5.10 (s, 2H); 4.50-4.60 (bs, 1H); 3.90 (s, 3H); 3.30-3.40 (m, 2H); 3.75 (t, 2H, J=7.2 Hz); 1.44 (s, 9H).

Step C 2-[4-(3-Fluoro-benzyloxy)-3-methoxy-phenyl]-ethylamine hydrochloride 58.2 g (0.155 mol) of 2-[4-(3-fluoro-benzyloxy)-3-methoxy-phenyl]-ethyl]-carbamic acid tert-butyl ester was dissolved in 300 ml of ethyl acetate. 150 ml of anhydrous 2 M hydrochloric acid in ethyl acetate were added and the mixture was stirred at room temperature overnight. The solid was filtered and washed with ethyl acetate and with diethyl ether and 44.2 g (91% yield) of a white solid were obtained.

$^1$H-NMR $D_2O$: 7.31-7.17 (m, 1H); 7.11-6.80 (m, 5H); 6.69-6.61 (m, 1H); 5.02 (s, 2H); 3.69 (s, 3H); 3.05 (t, 2H, J=6.85 Hz); 2.74 (t, 2H, J=6.85 Hz).

Step D [2-[4-(3-Fluoro-benzyloxy)-3-methoxy-phenyl]-ethylamino]-acetic acid methyl ester hydrochloride 1 g (3.2 mmol) of 2-[4-(3-fluoro-benzyloxy)-3-methoxy-phenyl]-ethylamine, 833 mg (6 mmol) of $K_2CO_3$, 50 mg of potassium iodide and 0.27 ml (2.9 mmol) of bromo-acetic acid methyl ester were dissolved in 10 ml of dimethylformamide and the mixture was stirred at room temperature overnight. Solvent was removed, water was added to the residue and the residue was extracted with ethyl acetate. The crude product was purified by flash chromatography (dichloromethane/methanol/$NH_3$ 100:0:0→100:2.5:0.25 gradient v:v:v). The product obtained was dissolved in anhydrous hydrochloric acid in ethyl acetate. The solvent was removed and the residue was triturated with diethyl ether. 482 mg (39% yield) of the title compound were obtained as a brown solid.

$^1$H-NMR $CDCl_3$: 7.39-7.28 (m, 2H); 7.22-6.92 (m, 2H); 7.04-6.92 (m, 1H); 6.86-6.74 (m, 3H); 5.10 (s, 2H); 3.88 (s, 3H); 3.87-3.80 (m, 2H); 3.78 (s, 3H); 3.41-3.19 (m, 4H).

Step E 2-[2-[4-(3-Fluoro-benzyloxy)-3-methoxy-phenyl]-ethylamino]-N-methyl-acetamide hydrochloride 900 mg (2.34 mmol) of [2-[4-(3-fluoro-benzyloxy)-3-methoxy-phenyl]-ethylamino]-acetic acid methyl ester were dissolved in 10 ml of dry toluene and 5 ml (10 mmol) of a 2 M solution of methylamine in tetrahydrofuran were added at 0° C., followed by 5 ml (10 mmol) of a 2 M solution of trimethyl aluminium in heptane. The reaction was stirred at room temperature overnight. The solution was cooled down to 0° C. and poured into methanol. The solvent was removed and the crude product was purified by flash chromatography (dichloromethane/methanol/$NH_3$ 100:0:0→100:4:0.4 gradient v:v:v). The product was dissolved in anhydrous hydrochloric acid in ethyl acetate, and the solid was filtered. 590 mg (66% yield) of the title compound were isolated as a hygroscopic solid.

$^1$H-NMR dimethylsulfoxide-$d_6$: 9.06 (m, 2H); 8.46 (bm, 1H); 7.49-6.67 (m, 7H); 5.07 (s, 2H); 3.76 (s, 3H); 3.73-3.63 (bm, 2H); 3.23-3.04 (m., 2H); 2.94-2.80 (bm, 2H); 2.65 (d, 3H, J=4.36 Hz).

LC-MS: $MH^+$=347.4

Example 2

2-[[2-[4-(3-Fluoro-benzyloxy)-3-methoxy-phenyl]-ethyl]-isobutylamino]-N-methyl-acetamide hydrochloride The above compound was synthesized according to Scheme 2

Scheme 2

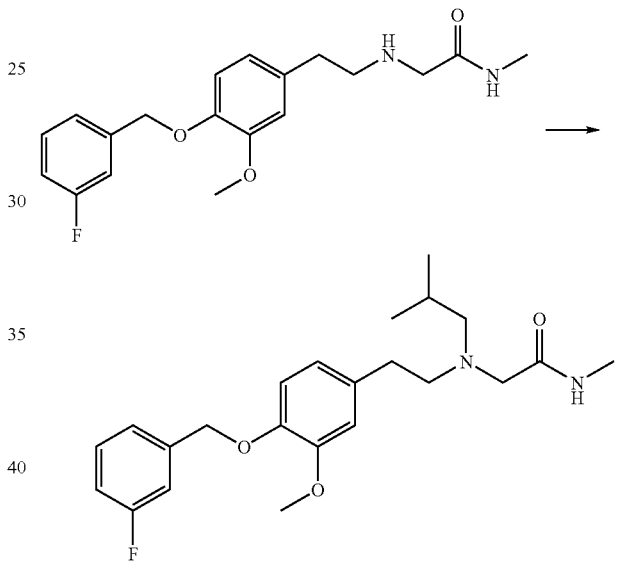

90 mg of 2-[2-[4-(3-Fluoro-benzyloxy)-3-methoxy-phenyl]-ethylamino]-N-methyl-acetamide (0.235 mmol) and 19 mg (0.263 mmol) of 2-methyl-propionaldehyde were dissolved in 6 ml of a dichloromethane/acetic acid (8:2, v:v) mixture and 1.5 ml of methanol. 100 mg (0.425 mmol) of (polystyrylmethyl)trimethylammonium cyanoborohydride (loading: 4.25 mmol/g) were added and the mixture was stirred at room temperature overnight. The resin was filtered and the solvent was removed. The crude product was purified by flash chromatography (dichloromethane/methanol/$NH_3$ 100:0:0→100:2:0.2 gradient v:v:v). The product was dissolved in anhydrous hydrochloric acid in ethyl acetate, the solvent was removed and the residue was triturated with diethyl ether. 80 mg (77% yield) of the title compound were isolated as a hygroscopic solid.

$^1$H-NMR dimethylsulfoxide-$d_6$: 9.42 (bm, 1H); 8.73 (bm, 1H); 7.49-6.72 (m, 7H); 5.07 (s, 2H); 4.14-3.87 (m, 2H); 3.77 (s, 3H); 3.42-3.24 (m, 2H); 3.10-2.86 (m, 4H); 2.69-2.65 (m, 3H); 2.16-1.92 (m, 1H); 0.95 (d, 6H).

LC-MS: $MH^+$=403

Examples 3-13. These compounds were prepared analogously according to the procedure described in Scheme 2.

Example 3

2-[[2-[4-(3-Fluoro-benzyloxy)-3-methoxy-phenyl]-ethyl]-(2-propyn-1-yl)amino]N-methyl-acetamide hydrochloride

LC-MS: $MH^+=385$

Example 4

2-[[2-[4-(3-Fluoro-benzyloxy)-3-methoxy-phenyl]-ethyl]-(3-methyl-isoxazol-5-ylmethyl)amino]-N-methyl-acetamide hydrochloride

LC-MS: $MH^+=442$

Example 5

2-[[2-[4-(3-Fluoro-benzyloxy)-3-methoxy-phenyl]-ethyl]-(3-methoxy-isoxazol-5-ylmethyl)amino]-N-methyl-acetamide hydrochloride

Example 6

2-[[2-[4-(3-Fluoro-benzyloxy)-3-methoxy-phenyl]-ethyl]-(1-methyl-imidazol-5-ylmethyl)amino]-N-methyl-acetamide hydrochloride

LC-MS: $MH^+=441$

Example 7

2-[[2-[4-(3-Fluoro-benzyloxy)-3-methoxy-phenyl]-ethyl]-(tetrahydrofuran-3-ylmethyl)amino]-N-methyl-acetamide hydrochloride

LC-MS: $MH^+=431$

Example 8

2-[[2-[4-(3-Fluoro-benzyloxy)-3-methoxy-phenyl]-ethyl]-(cyclopropylmethyl)amino]-N-methyl-acetamide hydrochloride

LC-MS: $MH^+=401$

Example 9

2-[[2-[4-(3-Fluoro-benzyloxy)-3-methoxy-phenyl]-ethyl]-(furan-2-ylmethyl)amino]-N-methyl-acetamide hydrochloride

LC-MS: $MH^+=427$

Example 10

2-[[2-[4-(3-Fluoro-benzyloxy)-3-methoxy-phenyl]-ethyl]-(furan-3-ylmethyl)amino]-N-methyl-acetamide hydrochloride

LC-MS: $MH^+=427$

Example 11

2-[[2-[4-(3-Fluoro-benzyloxy)-3-methoxy-phenyl]-ethyl]-(5-hydroxymethylfuran-2-ylmethyl)amino]-N-methyl-acetamide hydrochloride

LC-MS: $MH^+=457$

Example 12

2-[[2-[4-(3-Fluoro-benzyloxy)-3-methoxy-phenyl]-ethyl]-[(1,2,3-thiadiazol-4-ylmethyl)amino]-N-methyl-acetamide hydrochloride

LC-MS: $MH^+=445$

Example 13

2-[[2-[4-(3-Fluoro-benzyloxy)-3-methoxy-phenyl]-ethyl]-(1,3-dimethyl-pyrazol-5-ylmethyl)amino]-N-methyl-acetamide hydrochloride

LC-MS: $MH^+=455$

Examples 14-15. These compounds were prepared analogously, according to the procedure described in Scheme 2, but were not salified with hydrochloric acid.

Example 14

2-[[2-[4-(3-Fluoro-benzyloxy)-3-methoxy-phenyl]-ethyl]-(6-methoxy-pyridin-3-ylmethyl)amino]-N-methyl-acetamide

LC-MS: $MH^+=468$

Example 15

2-[[2-[4-(3-Fluoro-benzyloxy)-3-methoxy-phenyl]-ethyl]-(3,5-dimethoxybenzyl)amino]-N-methyl-acetamide

LC-MS: $MH^+=497$

Examples 16-25. These compounds were prepared analogously, according to the procedure described in Scheme 2 of Example 2 starting from 2-[2-[4-(3-fluoro-benzyloxy)-3-methoxy-phenyl]-ethylamino]-N,N-dimethyl-acetamide instead of 2-[2-[4-(3-fluoro-benzyloxy)-3-methoxy-phenyl]-ethylamino]-N-methyl-acetamide.

Example 16

2-[[2-[4-(3-Fluoro-benzyloxy)-3-methoxy-phenyl]-ethyl]-methylamino]-N,N-dimethyl-acetamide hydrochloride

LC-MS: $MH^+=375$

Example 17

2-[[2-[4-(3-Fluoro-benzyloxy)-3-methoxy-phenyl]-ethyl]-(cyclopropylmethyl)amino]-N,N-dimethyl-acetamide hydrochloride

LC-MS: $MH^+=415$

Example 18

2-[[2-[4-(3-Fluoro-benzyloxy)-3-methoxy-phenyl]-ethyl]-isopropylamino]-N,N-dimethyl-acetamide hydrochloride

LC-MS: $MH^+=403$

Example 19

2-[[2-[4-(3-Fluoro-benzyloxy)-3-methoxy-phenyl]-ethyl]-(1-methyl-piperidin-4-yl)amino]-N,N-dimethyl-acetamide hydrochloride

LC-MS: $MH^+=458$

Example 20

2-[[2-[4-(3-Fluoro-benzyloxy)-3-methoxy-phenyl]-ethyl]-benzylamino]-N,N-dimethyl-acetamide hydrochloride

LC-MS: MH+=451

Example 21

2-[[2-[4-(3-Fluoro-benzyloxy)-3-methoxy-phenyl]-ethyl]-ethylamino]-N,N-dimethyl-acetamide hydrochloride

LC-MS: MH+=389

Example 22

2-[[2-[4-(3-Fluoro-benzyloxy)-3-methoxy-phenyl]-ethyl]-(furan-2-ylmethyl)amino]-N,N-dimethyl-acetamide hydrochloride

LC-MS: MH+=441

Example 23

2-[[2-[4-(3-Fluoro-benzyloxy)-3-methoxy-phenyl]-ethyl]-(thien-2-ylmethyl)amino]-N,N-dimethyl-acetamide hydrochloride

LC-MS: MH+=457

Example 24

2-[[2-[4-(3-Fluoro-benzyloxy)-3-methoxy-phenyl]-ethyl]-(thiazol-2-ylmethyl)amino]-N,N-dimethyl-acetamide hydrochloride

LC-MS: MH+=458

Example 25

2-[[2-[4-(3-Fluoro-benzyloxy)-3-methoxy-phenyl]-ethyl]-(pyridin-3-ylmethyl)amino]-N,N-dimethyl-acetamide hydrochloride

LC-MS: MH+=452

Examples 26-27. These compounds were prepared analogously according to the procedure described in Scheme 2, starting from 2-[2-[4-(3-fluoro-benzyloxy)-3-methoxy-phenyl]-ethylamino]-N,N-dimethyl-acetamide instead of 2-[2-[4-(3-fluoro-benzyloxy)-3-methoxy-phenyl]-ethylamino]-N-methyl-acetamide, but were not salified with hydrochloric acid.

Example 26

2-[[2-[4-(3-Fluoro-benzyloxy)-3-methoxy-phenyl]-ethyl]-(2-hydroxyethyl)amino]-N,N-dimethyl-acetamide

LC-MS: MH+=405

Example 27

2-[[2-[4-(3-Fluoro-benzyloxy)-3-methoxy-phenyl]-ethyl]-(thiazol-2-yl)amino]-N,N-dimethyl-acetamide

Example 28

2-[2-[4-(3-Fluoro-benzyloxy)-3-methoxy-phenyl]-ethylamino]-N,N-dimethyl-acetamide hydrochloride The above compound was synthesized according to Scheme 3

Scheme 3

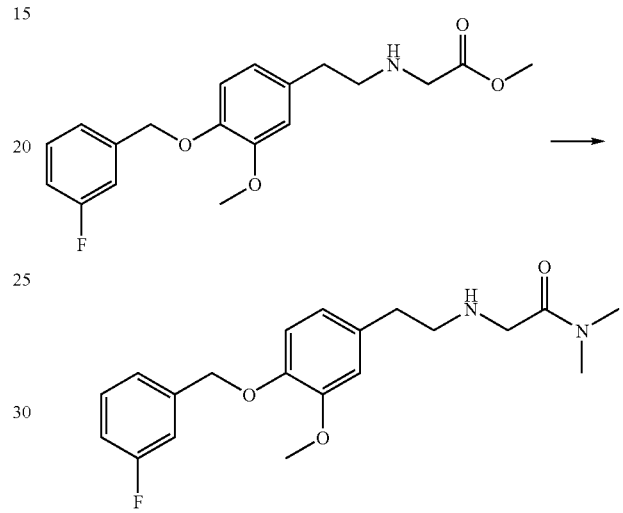

100 mg (0.26 mmol) of 2-[2-[4-(3-fluoro-benzyloxy)-3-methoxy-phenyl]-ethylamino]-acetic acid methyl ester were dissolved in 5 ml of dry toluene. 0.4 ml (0.8 mmol) of a 2 M solution of dimethylamine solution in tetrahydrofuran was added at 0° C., followed by 0.4 ml (0.8 mmol) of a 2 M solution of trimethyl aluminium in heptane. The reaction was stirred for 4 hours at room temperature. The solution was cooled down to 0° C. and poured into methanol. The solvent was removed and the crude residue was purified by flash chromatography (dichloromethane/methanol/NH$_3$ 100:5:0.5 v:v:v). The product was dissolved in ethyl acetate/hydrochloric acid. The solvent was removed and the residue was triturated with diethyl ether. 70 mg (68% yield) of the title compound were isolated as a hygroscopic solid.

$^1$H-NMR CDCl$_3$: 9.56 (bs, 1H); 7.38-7.27 (m, 2H); 7.21-7.10 (m, 2H); 7.04-6.86 (m, 2H); 6.79-6.76 (m, 2H); 5.10 (s, 2H); 3.93 (t broad, 2H); 3.89 (s, 3H); 3.41-3.15 (m, 4H); 2.94 (s, 6H)

LC-MS: MH+=361

Example 29

2-[2-[4-(3-Fluoro-benzyloxy)-3-methoxy-phenyl]-ethylamino]-1-(pyrrolidin-1-yl)-ethanone hydrochloride This compound was prepared as described in Scheme 3 using pyrrolidine in dimethylformamide instead of N,N-dimethylamine, to obtain the desired compound as a white solid (yield 48%).

$^1$H-NMR CDCl$_3$: 9.57 (s broad, 1H); 7.38-7.27 (m, 2H); 7.21-7.10 (m, 2H); 7.04-6.76 (m, 4H); 5.10 (s, 2H); 3.89 (s, 3H); 3.84 (t broad, 2H); 3.50-3.14 (m, 8H); 2.07-1.80 (m, 4H)

LC-MS: MH+=387

Example 30

2-[2-[4-(3-Fluoro-benzyloxy)-3-methoxy-phenyl]-ethylamino]-N,N-dimethyl-propionamide hydrochloride The above compound was synthesized according to Scheme 4

Scheme 4

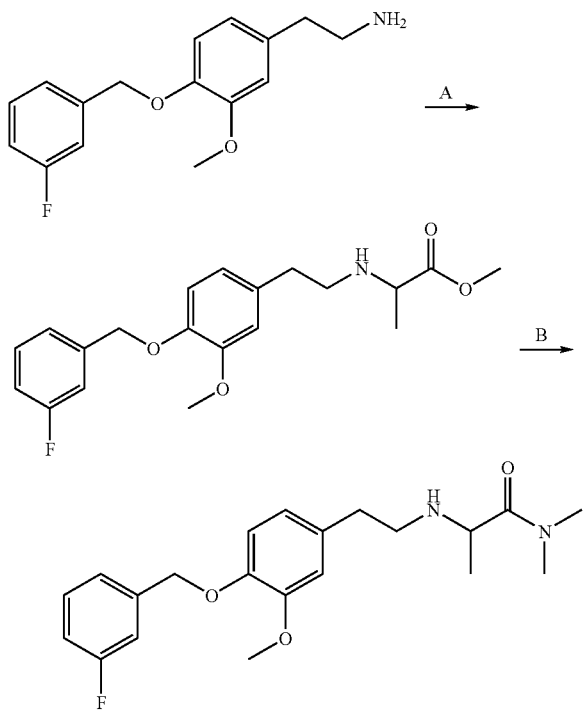

Step A 2-[2-[4-(3-Fluoro-benzyloxy)-3-methoxy-phenyl]-ethylamino]-propionic Acid Methyl Ester hydrochloride A solution of 0.75 g (2.4 mmol) of 2-[4-(3-fluoro-benzyloxy)-3-methoxy-phenyl]-ethylamine, 0.88 ml (5.05 mmol) of di-isopropylethylamine and 0.294 ml (2.64 mmol) of 2-bromo-propionic acid methyl ester in 10 ml of dry tetrahydrofuran was kept at 75° C. for 48 hours. The reaction mixture was poured into water and the product was extracted with ethyl acetate. The solvent was removed and the crude residue was purified by flash chromatography (dichloromethane/methanol/NH$_3$ 100:0:0→100:2:0.2 gradient). The product was dissolved in ethyl acetate/hydrochloric acid. The solvent was removed and the residue was triturated with diethyl ether. 300 mg (31% yield) of a white solid were isolated.

$^1$H-NMR D$_2$O: 7.35-7.18 (m, 1H); 7.16-6.80 (m, 5H); 6.75-6.62 (m, 1H); 5.05 (s, 2H); 4.06-3.88 (m, 1H); 3.77-3.64 (m, 6H); 3.18 (bt, 2H); 2.83 (bt, 2H); 1.43-1.34 (m, 3H)

Step B 2-[2-[4-(3-Fluoro-benzyloxy)-3-methoxy-phenyl]-ethylamino]-N,N-dimethyl-propionamide hydrochloride 125 mg (0.31 mmol) of 2-[2-[4-(3-fluoro-benzyloxy)-3-methoxy-phenyl]-ethylamino]-propionic acid methyl ester were dissolved in 5 ml of dry toluene. 0.785 ml (1.57 mmol) of a 2 M solution of dimethylamine in tetrahydrofuran were added at 0° C., followed by 0.47 ml (0.94 mmol) of a 2 M solution of trimethyl aluminium in heptane. The reaction was stirred for 5 hours at room temperature. The solution was cooled down to 0° C. and poured into methanol. The solvent was removed and the crude product was purified by flash chromatography (dichloromethane/methanol/NH$_3$ 100:5:0.5). The product was dissolved in ethyl acetate/hydrochloric acid. The solvent was removed and the solid was filtered. 94 mg (74% yield) of the title compound were isolated as a hygroscopic solid.

$^1$H-NMR CDCl$_3$: 8.01 (bs, 1H); 7.38-7.09 (m, 3H); 7.03-6.72 (m, 4H); 5.08 (s, 2H); 4.49-4.30 (m, 1H); 3.86 (s, 3H); 3.42-3.07 (m, 4H); 2.98 (d, 6H, J=7.51 Hz); 1.69-1.60 (m, 3H).

Example 31

(S)-2-[2-[4-(3-Fluoro-benzyloxy)-3-methoxy-phenyl]-ethylamino]-N-methyl-4-methyl-valeramide

LC-MS: MH$^+$=403

This compound was prepared analogously, according to the procedure described in Scheme 4

Example 32

2-[2-[4-(3-Fluoro-benzyloxy)-3-methoxy-phenyl]-ethylamino]-2-phenyl-N,N-dimethyl-acetamide hydrochloride The above compound was synthesized according to Scheme 5

Scheme 5

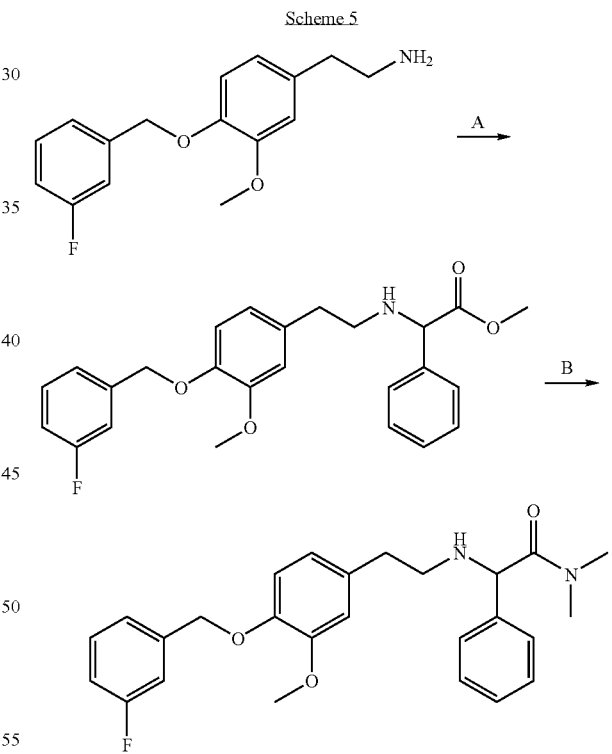

Step A 2-[2-[4-(3-Fluoro-benzyloxy)-3-methoxy-phenyl]-ethylamino]-2-phenyl-acetic Acid Methyl Ester A solution of 0.75 g (2.4 mmol) of 2-[4-(3-fluoro-benzyloxy)-3-methoxy-phenyl]-ethylamine, 0.88 ml (5.05 mmol) of di-isopropylethylamine and 0.416 ml (2.64 mmol) of 2-bromo-2-phenyl-acetic acid methyl ester in 10 ml of dry tetrahydrofuran was kept at 75° C. for 48 hours. The reaction mixture was poured into water and the product was extracted with ethyl acetate. The crude product was purified by flash chromatography (dichloromethane/methanol/NH$_3$ 100:0:0→100:2:0.2 gradient v:v:v). 600 mg (50% yield) of the title compound were obtained as a yellow oil.

$^1$H-NMR D$_2$O: 7.45-7.16 (m, 6H); 7.10-6.84 (m, 3H); 6.81-6.70 (m, 2H); 6.57 (dd, 1H, J=8.37 and 2.16 Hz); 4.99 (s, 2H); 4.93 (s, 1H); 3.63 (d, 6H, J=2.38 Hz); 3.13-2.68 (m, 4H).

Step B 2-[2-[4-(3-Fluoro-benzyloxy)-3-methoxy-phenyl]-ethylamino]-N,N-dimethyl-2-phenyl-acetamide This compound was synthesized according to the procedure described in Scheme 6, step B, using 115 mg of 2-[2-[4-(3-fluoro-benzyloxy)-3-methoxy-phenyl]-ethylamino]-2-phenyl-acetic acid methyl ester (0.27 mmol), 1.06 ml (2.1 mmol) of a 2 M solution of dimethylamine in tetrahydrofuran and 0.53 ml (1.06 mmol) of a 2 M solution of trimethyl aluminium in heptane. 66 mg (52% yield) of the title compound were isolated as a white solid.

$^1$H-NMR CDCl$_3$: 8.52 (bs, 1H); 7.47-7.10 (m, 9H); 7.03-6.92 (m, 2H); 6.81-6.62 (m, 3H); 5.42 (bs, 1H); 5.10 (s, 2H); 3.58 (s, 3H); 3.24-2.99 (m, 4H); 2.91 (d, 6H)

Example 33-35: These compounds were prepared according to the procedure described in Scheme 5 using the relevant amine in step B.

Example 33

2-[2-[4-(3-Fluoro-benzyloxy)-3-methoxy-phenyl]-ethylamino]-1-(morpholin-4-yl)-2-phenyl-ethanone hydrochloride (yield 51%).

$^1$H-NMR CDCl$_3$: 8.59 (bs, 1H); 7.48-7.26 (m, 6H); 7.21-7.10 (m, 2H); 7.04-6.92 (m, 2H); 6.79-6.63 (m, 3H); 5.50 (bs, 1H); 5.09 (s, 2H); 3.85 (s, 3H); 3.76-3.33 (m, 6H); 3.23-2.91 (m, 6H).

Example 34

2-[2-[4-(3-Fluoro-benzyloxy)-3-methoxy-phenyl]-ethylamino]-1-(pyrrolidin-1-yl)-2-phenyl-ethanone hydrochloride

LC-MS: MH$^+$=463

Example 35

2-[2-[4-(3-Fluoro-benzyloxy)-3-methoxy-phenyl]-ethylamino]-1-(4-methylpiperazin-1-yl)-2-phenyl-ethanone hydrochloride

LC-MS: MH$^+$=492

Example 36

2-[[2-[4-(3-Fluoro-benzyloxy)-3-methoxy-phenyl]-ethyl]-benzylamino]-acetamide hydrochloride The above compound was synthesized according to Scheme 6

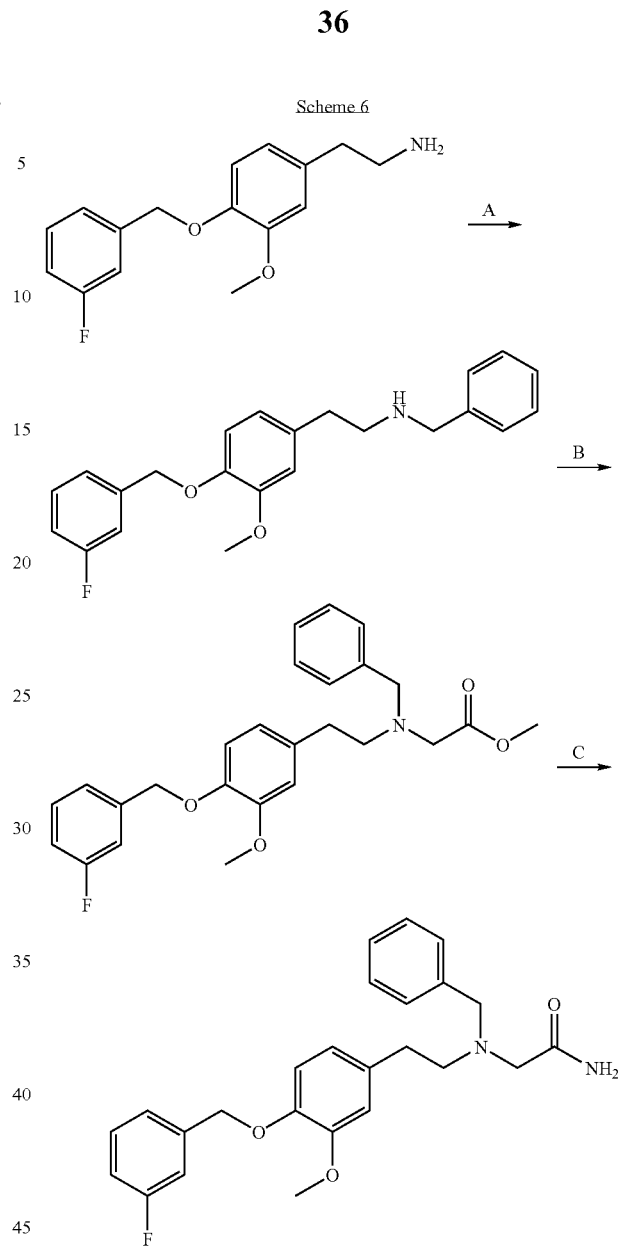

Scheme 6

Step A [2-[4-(3-fluoro-benzyloxy)-3-methoxy-phenyl]-ethyl]-benzylamine

A mixture of 4.4 g (16 mmol) of 2-[4-(3-fluoro-benzyloxy)-3-methoxy-phenyl]-ethylamine, 1.72 g (16 mmol) of benzaldehyde, 100 ml of ethanol and 30 g of 4 Å molecular sieves was refluxed overnight. The reaction mixture was cooled down to room temperature, 50 mg of PtO$_2$ were added and the mixture was hydrogenated at 15 psi for 5 hours. The catalyst was filtered off and the solvent was removed under reduced pressure. The crude reaction product was purified by flash chromatography (dichloromethane/methanol/NH$_3$ 85:15:1.5, v:v:v) and 2.72 g (46% yield) of the title compound were isolated as a yellow oil.

$^1$H-NMR CDCl$_3$: 10.12 (bs, 1H); 7.60-7.26 (m, 8H); 7.19-7.09 (m, 2H); 7.03-6.91 (m, 1H); 6.77-6.59 (m, 3H); 5.08 (s, 2H); 4.01 (t broad, 2H); 3.18-2.88 (m, 4H).

Step B 2-[[2-[4-(3-Fluoro-benzyloxy)-3-methoxy-phenyl]-ethyl]-benzylamino]-acetic Acid Methyl Ester 1.7 g (4.65 mmol) of [2-[4-(3-fluoro-benzyloxy)-3-methoxy-phenyl]-ethyl]-benzylamine, 1.74 ml (10 mmol) of di-isopropylethylamine and 0.5 ml (5.11 mmol) of 2-bromo-acetic acid methyl ester were dissolved in 20 ml of acetonitrile and the reaction was stirred at 70° C. overnight. The solvent was removed under reduced pressure, water was added to the residue and the product was extracted with ethyl acetate. The crude product was purified by flash chromatography (hexane/ethyl acetate 100:0→80:20 gradient v:v) and 1.94 g (95% yield) of the title compound were isolated as a yellow oil.

$^1$H-NMR CDCl$_3$: 7.72-7.65 (m, 2H); 7.47-7.28 (m, 5H); 7.21-7.10 (m, 2H); 7.04-6.93 (m, 1H); 6.85-6.67 (m, 3H); 5.11 (s, 2H); 4.68-4.30 (m, 2H); 3.89 (s, 3H); 3.72 (s, 3H); 3.68-3.15 (m, 6H).

Step C 2-[[2-[4-(3-Fluoro-benzyloxy)-3-methoxy-phenyl]-ethyl]-benzylamino]-acetamide hydrochloride 80 mg (0.18 mmol) of 2-[[2-[4-(3-fluoro-benzyloxy)-3-methoxy-phenyl]-ethyl]-benzylamino]-acetic acid methyl ester were dissolved in 3 ml of dioxane and 2 ml of NH$_3$ 30%. The solution was heated with microwaves at 100° C. for 8 hours. The solvent was removed and the crude reaction residue was purified by flash chromatography (dichloromethane/methanol/NH$_3$ 100:0:0→95:5:0.5 gradient v:v:v). The product was dissolved in anhydrous hydrochloric acid in ethyl acetate. The solvent was removed and the residue was triturated with diethyl ether. 30 mg (36% yield) of the title compound were isolated as a yellow solid.

$^1$H-NMR dimethylsulfoxide-d$_6$: 10.00 (bs, 1H); 7.95, 7.69 (2 bs, 2H); 7.63-6.67 (m, 12H); 5.06 (s, 2H); 4.42 (bs, 2H); 3.86 (bs, 2H); 3.75 (s, 3H); 3.38-3.12 (bs., 2H); 3.10-2.87 (bs., 2H).

LC-MS: MH$^+$=423

Examples 37-45. These compounds were prepared according to the procedure described in Scheme 6 step C, using the relevant amine

Example 37

2-[[2-[4-(3-Fluoro-benzyloxy)-3-methoxy-phenyl]-ethyl]-benzylamino]-N-ethylacetamide hydrochloride

LC-MS: MH$^+$+=451

Example 38

2-[[2-[4-(3-Fluoro-benzyloxy)-3-methoxy-phenyl]-ethyl]-benzylamino]-N-isopropyl-acetamide hydrochloride

LC-MS: MH$^+$=465

Example 39

2-[[2-[4-(3-Fluoro-benzyloxy)-3-methoxy-phenyl]-ethyl]-benzylamino]-N-ethylN-methyl-acetamide hydrochloride

LC-MS: MH$^+$=465

Example 40

2-[[2-[4-(3-Fluoro-benzyloxy)-3-methoxy-phenyl]-ethyl]-benzylamino]-1-(pyrrolidin-1-yl)-ethanone hydrochloride

LC-MS: MH$^+$=477

Example 41

2-[[2-[4-(3-Fluoro-benzyloxy)-3-methoxy-phenyl]-ethyl]-benzylamino]-Nbenzyl-acetamide hydrochloride

LC-MS: MH$^+$=513

Example 42

2-[[2-[4-(3-Fluoro-benzyloxy)-3-methoxy-phenyl]-ethyl]-benzylamino]-N-(2-amino-2-methyl-propyl)-acetamide hydrochloride

LC-MS: MH$^+$=494

Example 43

2-[[2-[4-(3-Fluoro-benzyloxy)-3-methoxy-phenyl]-ethyl]-benzylamino]-N-(2-dimethylamino-ethyl)-acetamide hydrochloride

LC-MS: MH$^+$=494

Example 44

2-[[2-[4-(3-Fluoro-benzyloxy)-3-methoxy-phenyl]-ethyl]-benzylamino]-N-[2-(1-methyl-pyrrolidin-2-yl)-ethyl]-acetamide hydrochloride

LC-MS: MH$^+$=534

Example 45

2-[[2-[4-(3-Fluoro-benzyloxy)-3-methoxy-phenyl]-ethyl]-benzylamino]-N-(3-imidazol-1-yl-propyl)-acetamide hydrochloride

LC-MS: MH$^+$=531

Example 46

2-[[2-[4-(3-Fluoro-benzyloxy)-3-methoxy-phenyl]-ethyl]-benzylamino]-N-methyl-acetamide This compound was prepared analogously, according to the procedure described in Scheme 6 step C, using the relevant amine, but was not salified with hydrochloric acid.
LC-MS: MH$^+$=437.4

Example 47

2-[[2-[4-(3-Fluoro-benzyloxy)-3-methoxy-phenyl]-ethyl]-(cyclopropylmethyl)amino]-N-ethyl-acetamide hydrochloride The above compound was synthesized according to Scheme 7

Scheme 7

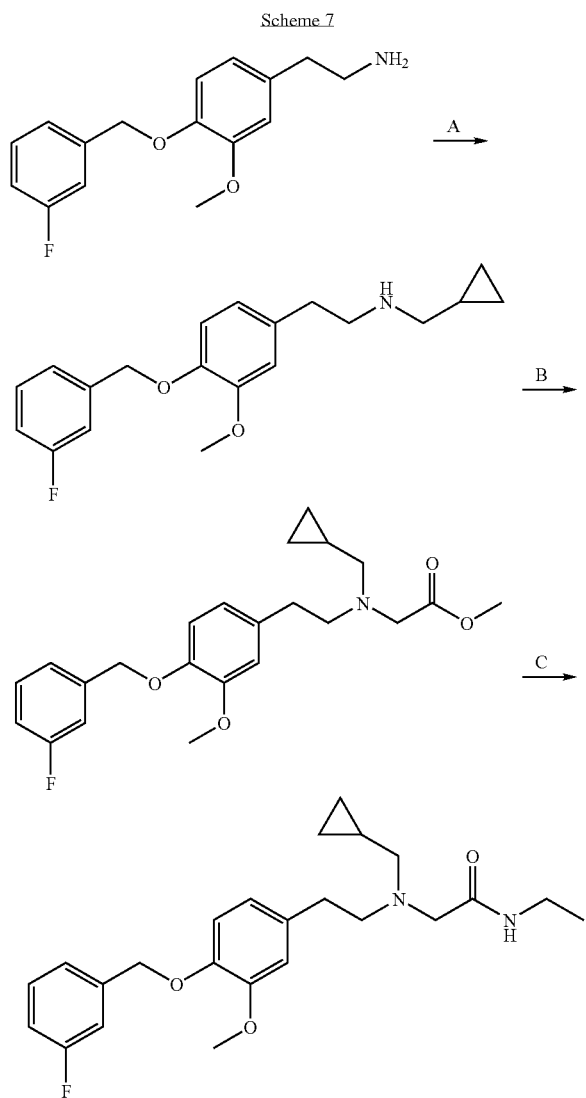

Step A [2-[4-(3-Fluoro-benzyloxy)-3-methoxy-phenyl]-ethyl]-(cyclopropylmethyl)amine A suspension of 0.66 g (2.1 mmol) of 2-[4-(3-fluoro-benzyloxy)-3-methoxy-phenyl]-ethylamine, 0.151 g (2.1 mmol) of cyclopropanecarbaldehyde, 0.3 ml of triethylamine and 3 g of molecular sieves in 6 ml of ethanol was stirred under reflux for 3 hours. The mixture was cooled to 0° C. and 0.2 g (5 mmol) of NaBH$_4$ was added portionwise. The reaction mixture was stirred at room temperature overnight. 3 ml of aqueous ammonium chloride were added, the solvent was removed under reduced pressure and the residue was extracted with ethyl acetate. The crude residue was purified by flash chromatography (dichloromethane/methanol/NH$_3$ 100:0:0→95:5:0.5 gradient v:v:v) to get 0.3 g of the desired compound as an oil (43% yield).

$^1$H-NMR CDCl$_3$: 9.80 (bm, 2H); 7.37-6.67 (m, 7H); 5.09 (s, 2H); 3.86 (s, 3H); 3.22 (bs, 4H); 2.92-2.80 (m, 2H); 0.93-0.78 (m, 1H); 0.75-0.63 (m, 2H); 0.49-0.38 (m, 2H).

Step B 2-[[2-[4-(3-Fluoro-benzyloxy)-3-methoxy-phenyl]-ethyl]-(cyclopropylmethyl)-amino]-acetic acid methyl ester 0.271 g (0.82 mmol) of [2-[4-(3-fluoro-benzyloxy)-3-methoxy-phenyl]-ethyl]-(cyclopropylmethyl)amine, 0.140 ml (1 mmol) of triethylamine and 0.155 g (0.89 mmol) of bromo-acetic acid methyl ester were dissolved in 5 ml of acetonitrile and the reaction was carried out at 70° C. overnight. Solvent was removed under vacuum, water was added to the residue and the product was extracted with ethyl acetate. The crude product was purified by flash chromatography (hexane/ethyl acetate 100:0→80:20 gradient v:v) and 0.32 g (97% yield) of the title compound was isolated as a yellow oil.

$^1$H-NMR CDCl$_3$: 7.38-7.28 (m, 1H); 7.22-7.10 (m, 2H); 7.04-6.91 (m, 1H); 6.80-6.62 (m, 3H); 5.11 (s, 2H); 3.88 (s, 3H); 3.70 (s, 3H); 3.59-3.50 (m, 2H); 3.00-2.53 (m, 6H); 0.96-0.78 (m, 1H); 0.58-0.46 (m, 2H); 0.18-0.07 (q broad, 2H).

Step C 2-[[2-[4-(3-Fluoro-benzyloxy)-3-methoxy-phenyl]-ethyl]-(cyclopropylmethyl)amino]-N-ethyl-acetamide 105 mg (0.26 mmol) of 2-[[2-[4-(3-fluoro-benzyloxy)-3-methoxy-phenyl]-ethyl]-(cyclopropylmethyl)amino]-acetic acid methyl ester were dissolved in 5 ml of dry toluene. 0.5 ml of a 2 M (1 mmol) solution of ethylamine in tetrahydrofuran were added at 0° C., followed by 0.4 ml (0.8 mmol) of a 2 M solution of trimethyl aluminium in heptane. The reaction was stirred for 4 hours at room temperature. The solution was cooled to 0° C. and poured into methanol. The solvent was removed and the crude product was purified by flash chromatography (ethyl acetate/hexane 0:100→85:15 gradient v:v) to obtain 52 mg (48% yield) of the title compound as a hygroscopic solid.

LC-MS: MH$^+$=415

$^1$H-NMR CDCl$_3$: 8.85 (bs, 1H); 7.39-6.64 (m, 7H); 5.09 (s, 2H); 4.19 (m, 2H); 3.86 (s, 3H); 3.61-3.42 (m, 2H); 3.42-3.09 (m, 6H); 1.36-1.17 (m, 1H); 1.22 (t, 3H, J=7.3 Hz); 0.81-0.65 (m, 2H); 0.53-0.41 (m, 2H).

Example 48

2-[[2-[4-(3-Fluoro-benzyloxy)-3-methoxy-phenyl]-ethyl]-(cyclopropylmethyl)amino]-N-isopropyl-acetamide hydrochloride This compound was prepared according to the procedure described here above using isopropyl amine instead of ethyl amine. 63 mg of the desired compound (52% yield) were isolated as a hygroscopic solid.

LC-MS: MH$^+$=429

Example 49

2-[[2-[4-(Benzyloxy)-3-methoxy-phenyl]-ethyl]-(cyclopropylmethyl)amino]-N-methyl-acetamide The above compound was synthesized according to Scheme 8

Scheme 8

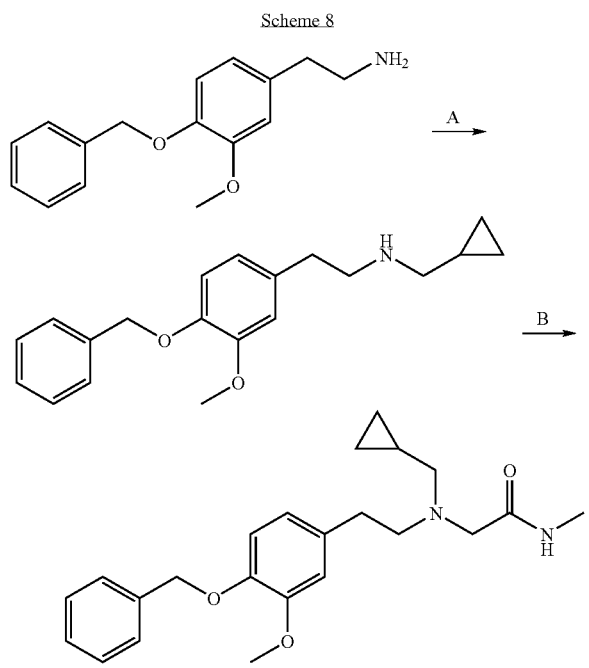

Step A [2-(4-Benzyloxy-3-methoxy-phenyl)-ethyl]-(cyclopropylmethyl)amine

A suspension of 1.5 g (5.1 mmol) of 2-(4-benzyloxy-3-methoxy-phenyl)-ethylamine, 0.365 g (5.1 mmol) of cyclopropanecarboxaldehyde, 0.7 ml of triethylamine and 8 g of molecular sieves in 15 ml of ethanol was stirred under reflux for 3 hours. The mixture was cooled down to 0° C. and 0.19 g (5 mmol) of $NaBH_4$ was added portionwise. The reaction mixture was stirred at room temperature overnight. 3 ml of aqueous ammonium chloride were added, the solvent was removed under vacuum and the residue was extracted with ethyl acetate. The crude product was purified by flash chromatography (dichloromethane/methanol/$NH_3$ 100:0:0→95:5:0.5 gradient v:v:v) to get 0.850 g (53% yield) of the desired compound as an oil.

LC-MS: $MH^+$=312

Step B 2-[[2-[4-(Benzyloxy)-3-methoxy-phenyl]-ethyl]-(cyclopropylmethyl)amino]-N-methyl-acetamide A mixture of 0.5 g (1.6 mmol) of [2-(4-benzyloxy-3-methoxy-phenyl)-ethyl]-(cyclopropylmethyl)amine, 0.27 ml (1.92 mmol) of triethylamine, 0.207 g (1.92 mmol) of 2-chloro-N-methyl-acetamide in 4 ml of dimethylformamide was heated with microwaves to 120° C. for 2 hours. The solvent was removed under vacuum and the crude was purified by flash chromatography (ethyl acetate/hexane 0:10→9:1 gradient). 0.52 g (84% yield) of the title compound was isolated as a yellow solid.

$^1$H-NMR $CDCl_3$: 7.49-6.62 (m, 8H); 5.14 (s, 2H); 3.88 (s, 3H); 3.14 (s, 2H); 2.83-2.58 (m, 4H); 2.52 (d, 3H, J=5.58 Hz); 2.43 (d, 2H, J=6.62 Hz); 0.91-0.69 (m, 1H.); 0.57-0.44 (m, 2H); 0.1-0.05 (m, 2H)

LC-MS: $MH^+$=383

Example 50

2-[[2-(3-Benzyloxy-phenyl)-ethyl]-(cyclopropylmethyl)amino]-N-methyl-acetamide hydrochloride The above compound was synthesized according to Scheme 9

Scheme 9

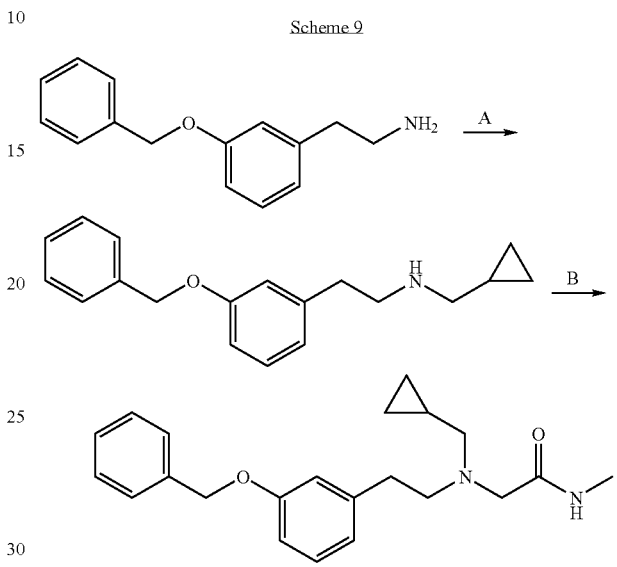

Step A [2-(3-Benzyloxy-phenyl)-ethyl]-(cyclopropylmethyl)amine

A suspension of 0.264 g (1 mmol) of 2-(3-benzyloxy-phenyl)-ethylamine, 70 mg (1 mmol) of cyclopropanecarboxaldehyde, and 5 g of molecular sieves in 4 ml of ethanol was stirred under reflux for 3 hours. The mixture was cooled to 0° C. and 37.8 mg (1 mmol) of $NaBH_4$ were added portionwise. The reaction mixture was stirred at room temperature overnight. 3 ml of aqueous ammonium chloride were added, the solvent was removed under vacuum and the residue was extracted with ethyl acetate. The crude product was purified by flash chromatography (dichloromethane/methanol/$NH_3$ 100:0:0→95:5:0.5 gradient v:v:v) to get 0.24 g (85% yield) of the desired compound as a yellow oil.

$^1$H-NMR $CDCl_3$: 7.48-6.78 (m, 9H); 5.06 (s, 2H); 3.00-2.71 (m, 4H); 2.50 (d, 2H); 1.03-0.81 (m, 1H); 0.55-0.41 (m, 2H); 0.16-0.06 (m, 2H).

Step B 2-[[2-(3-Benzyloxy-phenyl)-ethyl]-(cyclopropylmethyl)amino]-N-methyl-acetamide hydrochloride A mixture of 0.24 g (0.85 mmol) of [2-(3-benzyloxy-phenyl)-ethyl]-(cyclopropylmethyl)amine, 0.14 ml (1.00 mmol) of triethylamine, 0.11 g (1.02 mmol) of 2-chloro-N-methyl-acetamide in 3 ml of dimethylformamide was heated with microwaves to 120° C. for 2 hours. The solvent was removed and the crude residue was purified by flash chromatography (dichloromethane/methanol/$NH_3$ 100:0:0→95:5:0.5 gradient). The product obtained was dissolved in anhydrous hydrochloric acid in ethyl acetate, the solvent was removed under vacuum and the residue was triturated with diethyl ether. 0.24 g (80% yield) of the title compound was isolated as a yellow solid.

$^1$H-NMR CDCl$_3$: 7.47-6.68 (m, 9H); 5.06 (s, 2H); 3.15 (s, 2H); 2.86-2.62 (m, 4H); 2.56 (d, 3H); 2.43 (d, 2H); 0.92-0.67 (m, 1H); 0.59-0.44 (m, 2H); 0.16-0.04 (m, 2H)

LC-MS: MH$^+$=353

Example 51

2-[[2-(3-Benzyloxy-phenyl)-ethyl]-(furan-2-ylmethyl)amino]-N-methyl-acetamide hydrochloride The above compound was synthesized according to Scheme 10

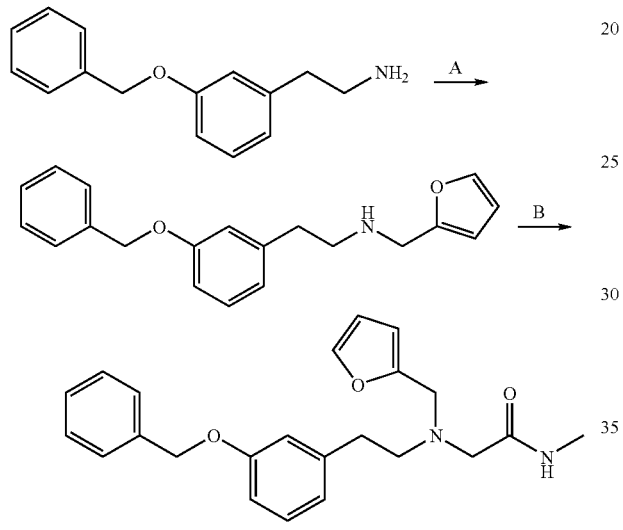

Step A [2-(3-Benzyloxy-phenyl)-ethyl]-(furan-2-ylmethyl)amine

A suspension of 30.2 g (133 mmol) of 2-(3-benzyloxy-phenyl)-ethylamine, 11.0 ml (133 mmol) of furan-2-carboxaldehyde, and 60 g of 4 Å molecular sieves in 300 ml of ethanol was kept under reflux for 3 hours. The mixture was cooled to 0° C. and 10.8 g (286 mmol) of NaBH$_4$ were added portionwise. The reaction mixture was stirred at room temperature overnight. 60 ml of aqueous ammonium chloride were added, the solvent was removed under vacuum and the residue was extracted with ethyl acetate. The crude product was purified by flash chromatography (dichloromethane/methanol/NH$_3$ 100:1:0.1 v:v:v) and 22.4 g (55% yield) of the title compound were isolated as a yellow oil.

$^1$H-NMR CDCl$_3$: 10.1 (b, 1H); 7.4-6.3 (m, 12H); 5 (s, 2H); 4.2 (t, 2H, J=4.9 Hz); 3.2-3.0 (m, 4H).

Step B 2-[[2-(3-Benzyloxy-phenyl)-ethyl]-(furan-2-ylmethy)amino]-N-methyl-acetamide hydrochloride A solution of 3.0 g (9.8 mmol) of [2-(3-benzyloxy-phenyl)-ethyl]-(furan-2-ylmethyl)amine, 15.0 g (10.7 mmol) of 2-chloro-N-methyl-acetamide and 1.87 ml (10.7 mmol) of diisopropylethylamine in 50 ml of acetonitrile was stirred under reflux for 24 hours. The solvent was removed under reduced pressure and the crude reaction mixture was purified by flash chromatography (ethyl acetate/hexane 1:1 v:v). The product isolated was dissolved in anhydrous hydrochloric acid in ethyl acetate. The solvent was removed under vacuum and the residue was triturated with diethyl ether. 2.66 g (65% yield) of the title compound were isolated as a hygroscopic solid.

$^1$H-NMR CDCl$_3$: 8.8 (b, 1H); 7.5-7.2 (m, 7H); 6.9-6.8 (m, 4H); 6.5 (m, 1H); 5.0 (s, 2H); 4.5-4.3 (m, 2H); 4.0-3.8 (m, 2H); 3.2 (m, 4H); 3-2.8 (m, 3H)

LC-MS: MH$^+$=379

Example 52

2-[[2-[3-(2-Fluoro-benzyloxy)-phenyl]-ethyl]-(furan-2-ylmethyl)amino]-N-methyl-acetamide hydrochloride The above compound was synthesized according to Scheme 11

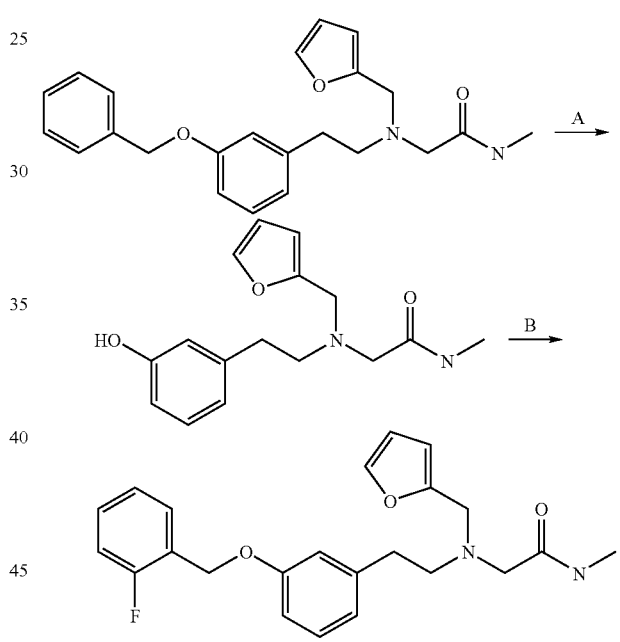

Step A 2-[[2-(3-Hydroxy-phenyl)-ethyl]-(furan-2-ylmethyl)amino]-N-methyl-acetamide 400 mg of Pd/C (10%) were added to a solution of 4.12 g (10.9 mmol) of 2-[[2-(3-benzyloxyphenyl)-ethyl]-(furan-2-ylmethyl)amino]-N-methyl-acetamide hydrochloride in 100 ml of methanol. The hydrogenation was carried out at 30 psi for 90 minutes at room temperature. The catalyst was filtered off, the solvent was removed and the crude product was purified by flash chromatography (ethyl acetate/hexane 1:1+ triethylamine). 2.1 g (67% yield) of the title compound were isolated as a white solid.

$^1$H-NMR CDCl$_3$: 7.37 (d, 1H, J=2.1); 7.20 (t, 1H, J=7.2); 6.75-6.67 (m, 4H); 6.33-6.31 (m, 1H); 6.20 (m, 1H); 5.72 (b, 1H); 3.72 (s, 2H); 3.14 (s, 2H); 2.74 (m, 4H); 2.56 (d, 3H, J=4.1).

LC-MS: MH$^+$=289

Step B 2-[[2-[3-(2-Fluoro-benzyloxy)-phenyl]-ethyl]-(furan-2-ylmethyl)amino]-N-methylacetamide hydrochloride A solution of 60 mg (0.21 mmol) of 2-[[2-(3-hydroxy-phenyl)-ethyl]-(furan-2-ylmethyl)amino]-N-methyl-acetamide, 36 mg (0.25 mmol) of 1-chloromethyl-2-fluoro-benzene, 44 mg of $K_2CO_3$ (0.32 mmol) and 3 mg of potassium iodide in 4 ml of dimethylformamide was refluxed overnight. The solvent was removed under vacuum and the crude product was purified by preparative HPLC. The isolated product was dissolved in ethyl acetate/hydrochloric acid. The solvent was removed under vacuum and the residue was triturated with diethyl ether. 65 mg (72% yield) of the title compound were isolated as a white solid.

$^1$H-NMR $CDCl_3$: 12.67 (b, 1H); 8.79 (m, 1H); 7.55-7.05 (m, 5H); 6.88 (m, 4H); 6.49 (m, 1H); 5.11 (s, 2H); 4.45 (m, 2H); 3.72 (m, 2H); 3.24 (m, 4H); 2.88 (d, 3H, J=4.56 Hz).

LC-MS: $MH^+$=397.3

Examples 53-68. These compounds were prepared according to the procedure described in Scheme 11 using the relevant reagents.

Example 53

2-[[2-[3-(3-Fluoro-benzyloxy)-phenyl]-ethyl]-(furan-2-ylmethyl)amino]-N-methyl-acetamide hydrochloride

Example 54

2-[[2-[3-(2-Chloro-benzyloxy)-phenyl]-ethyl]-(furan-2-ylmethyl)amino]-N-methyl-acetamide hydrochloride

LC-MS: $MH^+$=413

Example 55

2-[[2-[3-(3-Chloro-benzyloxy)-phenyl]-ethyl]-(furan-2-ylmethyl)amino]-N-methyl-acetamide hydrochloride

LC-MS: $MH^+$=413

Example 56

2-[[2-[3-(3-Methyl-benzyloxy)-phenyl]-ethyl]-(furan-2-ylmethyl)amino]-N-methyl-acetamide hydrochloride

LC-MS: $MH^+$=393

Example 57

2-[[2-[3-(4-Methyl-benzyloxy)-phenyl]-ethyl]-(furan-2-ylmethyl)amino]-N-methyl-acetamide hydrochloride

LC-MS: $MH^+$=393

Example 58

2-[[2-[3-(3-Trifluoromethyl-benzyloxy)-phenyl]-ethyl]-(furan-2-ylmethyl)amino]-N-methyl-acetamide hydrochloride

LC-MS: $MH^+$=447

Example 59

2-[[2-[3-(3-Fluoro-phenoxy)-phenyl]-ethyl]-(furan-2-ylmethyl)amino]-N-methylacetamide hydrochloride

LC-MS: $MH^+$=383

Example 60

2-[[2-[3-(2-Phenyl-ethoxy)-phenyl]-ethyl]-(furan-2-ylmethyl)amino]-N-methylacetamide hydrochloride

LC-MS: $MH^+$=393

Example 61

2-[[2-(3-Cyclopropylmethoxy-phenyl)-ethyl]-(furan-2-ylmethyl)amino]-N-methyl-acetamide hydrochloride

LC-MS: $MH^+$=343

Example 62

2-[[2-[3-(2-Piperidin-1-yl-ethoxy)-phenyl]-ethyl]-(furan-2-ylmethyl)amino]-N-methyl-acetamide hydrochloride

LC-MS: $MH^+$=340

Example 63

2-[[2-[3-(2-Morpholin-4-yl)-ethoxy)-phenyl]-(furan-2-ylmethyl)amino]-N-methyl-acetamide hydrochloride

LC-MS: $MH^+$=402

Example 64

2-[[2-[3-(2,2,2-Trifluoro-ethoxy)-phenyl]-(furan-2-ylmethyl)amino]-N-methyl-acetamide hydrochloride

LC-MS: $MH^+$=371

Example 65

2-[[2-[3-(3,5-Dimethyl-isoxazol-4-ylmethoxy)-phenyl]-ethyl]-(furan-2-ylmethyl)amino]-N-methyl-acetamide hydrochloride

LC-MS: $MH^+$=398

Example 66

2-[[2-[3-(5-Chloro-thien-2-ylmethoxy)-phenyl]-ethyl]-(furan-2-ylmethyl)amino]-N-methyl-acetamide hydrochloride

LC-MS: $MH^+$=419

Example 67

2-[[2-[3-(Pyridin-2-ylmethoxy)-phenyl]-ethyl]-(furan-2-ylmethyl)amino]-N-methyl-acetamide hydrochloride

LC-MS: $MH^+$=380

Examples 68-69. These compounds were prepared analogously, according to the procedure described in Scheme 11, using the relevant reagents, but were not salified with hydrochloric acid.

Example 68

2-[[2-[3-(4-Trifluoromethyl-benzyloxy)-phenyl]-ethyl]-(furan-2-ylmethyl)amino]-N-methyl-acetamide

LC-MS: MH$^+$=447

Example 69

2-[[2-(3-Cyclopentyloxy-phenyl)-ethyl]-(furan-2-ylmethyl)amino]-N-methylacetamide

LC-MS: MH$^+$=357

Example 70

2-[[2-[3-(3-Fluoro-benzyloxy)-phenyl]-ethyl]-(furan-2-ylmethyl)amino]-acetamide

The above compound was synthesized according to Scheme 12

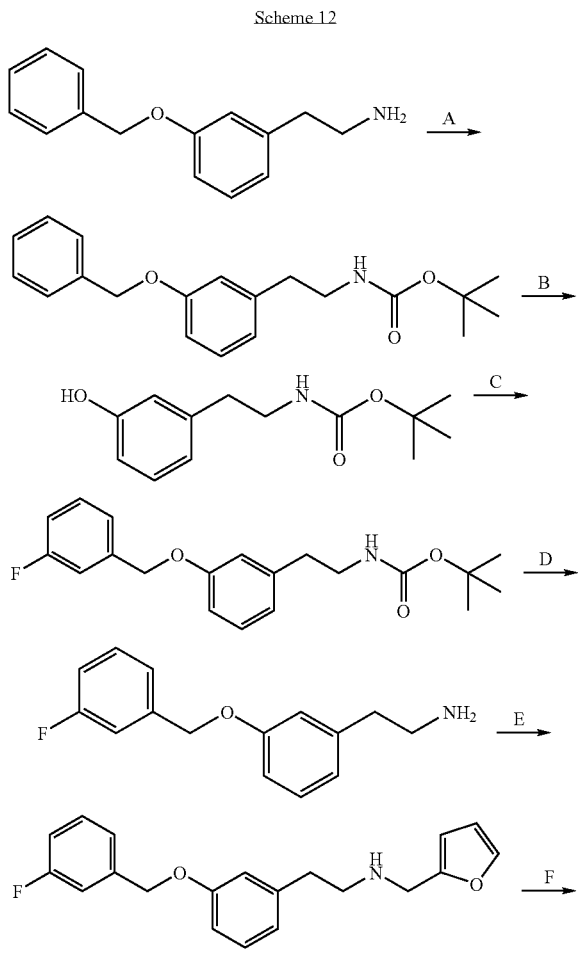

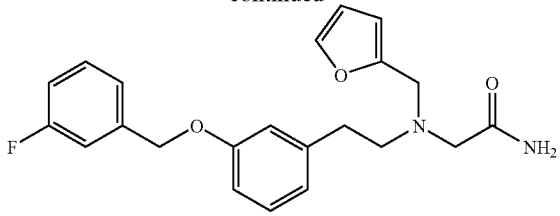

Step A [2-(3-Benzyloxy-phenyl)-ethyl]-carbamic acid tert-butyl ester 4.8 g of (Boc)$_2$O (22 mmol) in 10 ml of dichloromethane were added to a suspension of 5.27 g of 2-(3-benzyloxy-phenyl)-ethylamine-HCl (20 mmol) in 20 ml of dichloromethane and 2.78 ml of triethylamine (20 mmol). The reaction was stirred for 1 hour at room temperature. After evaporation of the solvent, an aqueous solution containing 5% citric acid was added to the residue and the product was extracted with ethyl acetate. The title product was isolated as a colorless oil in quantitative yield.

$^1$H-NMR CDCl$_3$: 7.45-6.78 (m, 9H); 5.05 (s, 2H); 4.54 (bs, 1H); 3.48-3.28 (m, 2H); 2.77 (t, 2H); 1.44 (s, 9H).

Step B [2-(3-Hydroxy-phenyl)-ethyl]-carbamic acid tert-butyl ester 1 g of Pd/C 10% was added to a solution of 13 g (0.039 mol) of [2-(3-benzyloxy-phenyl)ethyl]-carbamic acid tert-butyl ester in 100 ml of ethanol. The mixture was hydrogenated at 40 psi overnight. The catalyst was filtered off and washed with ethanol. The solvent was removed under vacuum and 9.4 g of the title compound were obtained as a colourless oil in quantitative yield.

$^1$H-NMR CDCl$_3$: 7.22-7.12 (m, 1H); 6.78-6.66 (m, 3H); 4.56 (bs, 1H); 3.42-3.30 (m, 2H); 2.74 (t, 2H); 1.44 (s, 9H).

Step C
[2-[3-(3-Fluoro-benzyloxy)-phenyl]-ethyl]-carbamic acid tert-butyl ester 2.87 g (19.8 mmol) of 1-chloromethyl-3-fluoro-benzene in 5 ml of dry dimethylformamide were added to a suspension of 4.66 g (19.6 mmol) of [2-(3-hydroxy-phenyl)-ethyl]-carbamic acid tert-butyl ester, 4 g of K$_2$CO$_3$ and 0.3 g of potassium iodide in 50 ml of dry dimethylformamide. The reaction was first stirred at room temperature overnight, then was heated up to 50° C. for 6 hours. After evaporation of the solvent, water was added to the residue and the product was extracted with ethyl acetate. 7 g of crude oil were obtained. Purification by flash chromatography using a mixture of ethyl acetate/hexane (1:9→2:8 gradient) gave 5.9 g (86% yield) of the title product as a colourless oil.

$^1$H-NMR CDCl$_3$: 7.40-6.68 (m, 8H); 5.05 (s, 2H); 4.53 (bs, 1H); 3.44-3.30 (m, 2H); 2.77 (t, 2H); 1.44 (s, 9H).

Step D
2-[3-(3-Fluoro-benzyloxy)-phenyl]-ethylamine

A solution of 10.36 g (30 mmol) of [2-[3-(3-fluoro-benzyloxy)-phenyl]-ethyl-carbamic acid tert-butyl ester in 100 ml of dichloromethane and 15 ml of trifluoroacetic acid was stirred at room temperature overnight. The solvent was removed, a 5% K$_2$CO$_3$ solution in water was added and the product was extracted with ethyl acetate to obtain the title compound in quantitative yield as a sticky oil.

$^1$H-NMR dimethylsulfoxide-d$_6$: 8.04 (bs, 3H); 7.49-6.72 (m, 8H); 5.09 (s, 2H); 3.08-2.75 (m, 4H).

Step E [2-[3-(3-fluoro-benzyloxy)-phenyl]-ethyl]-(furan-2-ylmethyl)amine 1.44 g (15 mmol) of furan-2-carboxaldehyde and 7.5 g of molecular sieves 3 Å were added to a solution of 2.45 g (10 mmol) of 2-[3-(3-fluoro-benzyloxy)-phenyl]-ethylamine in 50 ml of dry ethanol. The reaction mixture was refluxed for 3 hours. The molecular sieves were filtered off and the solution was cooled to 5° C. 0.57 g (15 mmol) of NaBH$_4$ was added under N$_2$ and the reaction was stirred at room temperature overnight. Solvent was removed, a 5% NaHCO$_3$ aqueous solution was added to the residue and the product was extracted with ethyl acetate. The crude product was purified by flash chromatography (dichloromethane/methanol/NH$_3$ 100:0:0→100:2:0.2, v:v:v). 2.2 g (68% yield) of an oil were obtained.

$^1$H-NMR CDCl$_3$: 7.44-6.12 (m, 11H); 5.04 (s, 2H); 3.79 (s, 2H); 2.96-2.73 (m, 4H).

Step F 2-[[2-[3-(3-Fluoro-benzyloxy)-phenyl]-ethyl]-(furan-2-ylmethyl)amino]-acetamide A solution of 1.8 g (5.53 mmol) of [2-[3-(3-fluoro-benzyloxy)-phenyl]-ethyl]-(furan-2-ylmethyl)amine, 0.57 g (6.08 mmol) of 2-chloro-acetamide and 0.92 ml (6.62 mmol) of triethylamine in 5 ml of dry dimethylformamide was heated at 120° C. for 2 hours with microwaves. Solvent was removed under vacuum, water was added and the product was extracted with ethyl acetate. The crude reaction mixture was purified by flash chromatography (dichloromethane/methanol 95:5 v:v). 2.1 g (99% yield) of a yellow oil were isolated.

$^1$H-NMR DMSO-d$^6$: 7.84-6.48 (m, 11H); 5.08 (s, 2H); 4.48 (s, 2H); 3.87 (s, 2H); 3.33-2.87 (m, 4H).

Example 71

2-[[2-[3-(3-Fluoro-benzyloxy)-phenyl]-ethyl]-(furan-2-ylmethyl)amino]-N-(2-dimethylamino-ethyl)-acetamide Dihydrochloride The above compound was synthesized according to Scheme 13

Scheme 13

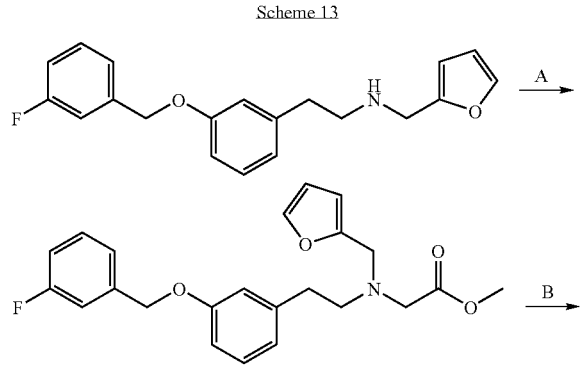

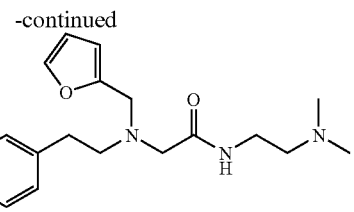

Step A 2-[[2-[3-(3-Fluoro-benzyloxy)-phenyl]-ethyl]-(furan-2-ylmethyl)amino]-acetic Acid Methyl Ester 0.46 g (3.05 mmol) of 2-bromo-acetic acid methyl ester were added to a solution of 0.9 g (2.76 mmol) of [2-[3-(3-fluoro-benzyloxy)-phenyl]-ethyl]-(furan-2-ylmethyl)amine and 0.39 g (3.05 mmol) of di-isopropylethylamine in 15 ml of acetonitrile. Solvent was removed, water was added to the residue and the product was extracted with ethyl acetate. Purification by flash chromatography (ethyl acetate/hexane 1:9→2:8 gradient v:v) gave 0.9 g (82% yield) of a clear oil.

$^1$H-NMR CDCl$_3$: 7.40-7.11 (m, 5H); 7.06-6.94 (m, 1H); 6.83-6.74 (m, 3H); 6.33-6.29 (m, 1H); 6.20 (d, 1H, J=3.34 Hz); 5.04 (s, 2H); 3.90 (s, 2H); 3.70 (s, 3H); 3.40 (s, 2H); 2.92-2.72 (m, 4H).

Step B 2-[[2-[3-(3-Fluoro-benzyloxy)-phenyl]-ethyl]-(furan-2-ylmethyl)amino]-N-(2-dimethylamino-ethyl)-acetamide Dihydrochloride 100 mg (0.25 mmol) of 2-[[2-[3-(3-fluoro-benzyloxy)-phenyl]-ethyl]-(furan-2-ylmethyl)amino]-acetic acid methyl ester were dissolved in 5 ml of dry toluene. 66 mg (0.75 mmol) of N,N-dimethyl-ethane-1,2-diamine were added at 0° C. followed by 0.4 ml (0.8 mmol) of 2 M triethyl aluminium in heptane. The reaction mixture was heated to 60° C. overnight. The solution was cooled at 0° C. and poured into methanol. The solvent was removed under vacuum and the crude product was purified by flash chromatography (dichloromethane/methanol/NH$_3$ 100:2:0.2, v:v:v). The product was dissolved in ethyl acetate/hydrochloric acid, and the solid obtained was filtered. 80 mg (65% yield) of the title compound were isolated as hygroscopic solid.

$^1$H-NMR D$_2$O: 7.48-6.29 (m, 1H); 4.95 (s, 2H); 4.33 (s, 2H); 3.88 (s, 2H); 3.48-3.34 (m, 2H); 3.32-3.17 (m, 2H); 3.15-3.04 (m, 4H); 2.97-2.77 (m, 2H); 2.72 (s, 6H)

Example 72

2-[[2-[3-(3-Fluoro-benzyloxy)-phenyl]-ethyl]-(furan-2-ylmethyl)amino]-N-(2-amino-2-methyl-propyl)-acetamide Dihydrochloride 100 mg (0.25 mmol) of 2-[[2-[3-(3-fluoro-benzyloxy)-phenyl]-ethyl]-(furan-2-ylmethyl)amino]-acetic acid methyl ester and 1 ml of 2-methyl-propane-1,2-diamine were heated at 120° C. for 3 hours with microwaves. The reaction mixture was cooled to room temperature, water was added and the product was extracted with ethyl acetate. The crude product was purified by flash chromatography (dichloromethane/methanol 95:5 v:v). The product was dissolved in ethyl acetate/hydrochloric acid, the solvent was removed and the resulting salt was triturated with diethyl ether. 95 mg (72% yield) of the title compound were isolated as a hygroscopic solid.

$^1$H-NMR CDCl$_3$: 10.95 (bs, 1H); 9.13 (bs, 1H); 8.46 (bs, 3H); 7.47-6.32 (m, 11H); 4.99 (s, 2H); 4.89-4.45 (m, 2H,); 4.45-4.09 (bs, 2H); 3.87-3.00 (m, 6H); 1.52 (s, 6H).

LC-MS: MH$^+$=454

Examples 73-76: These compounds were prepared according to the procedure described in Scheme 13 using the relevant amines

Example 73

2-[[2-[3-(3-Fluoro-benzyloxy)-phenyl]-ethyl]-(furan-2-ylmethyl)amino]-N-(2-methoxy-ethyl)-acetamide hydrochloride

LC-MS: MH$^+$=441

Example 74

2-[[2-[3-(3-Fluoro-benzyloxy)-phenyl]-ethyl]-(furan-2-ylmethyl)amino]-N-(1,3,4-thiadiazol-2-yl)-acetamide hydrochloride

LC-MS: MH$^+$=467

Example 75

2-[[2-[3-(3-Fluoro-benzyloxy)-phenyl]-ethyl]-(furan-2-ylmethyl)amino]-N-(3-methyl-isoxazol-5-yl)-acetamide hydrochloride

LC-MS: MH$^+$=464

Example 76

2-[[2-[3-(3-Fluoro-benzyloxy)-phenyl]-ethyl]-(furan-2-ylmethyl)amino]-N-(1H-pyrazol-3-yl)-acetamide hydrochloride

LC-MS: MH$^+$=449

Examples 77-78. These compounds were prepared according to the procedure described in Scheme 13 using the relevant amine, but were not salified with hydrochloric acid.

Example 77

2-[[2-[3-(3-Fluoro-benzyloxy)-phenyl]-ethyl]-(furan-2-ylmethyl)amino]-N-(1H-imidazol-2-yl)-acetamide

LC-MS: MH$^+$=449

Example 78

2-[[2-[3-(3-Fluoro-benzyloxy)-phenyl]-ethyl]-(furan-2-ylmethyl)amino]-N-thiazol-2-yl-acetamide

LC-MS: MH$^+$=466

Example 79

2-[[2-[3-(2,2,2-Trifluoro-ethoxy)-phenyl]-ethyl]-isopropylamino]-N,N-dimethyl-acetamide hydrochloride The above compound was synthesized according to Scheme 14

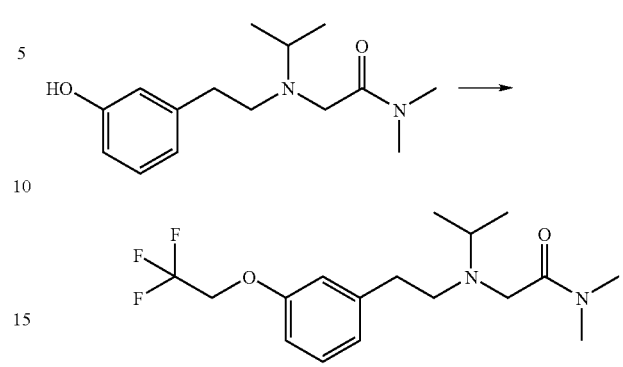

Scheme 14

2-([2-[3-(2,2,2-Trifluoro-ethoxy)-phenyl]-ethyl]-isopropylamino)-N,N-dimethyl-acetamide hydrochloride 19.6 mg (0.49 mmol) of NaH 60% in mineral oil were added to a solution of 100 mg (0.378 mmol) of 2-[[2-(3-hydroxy-phenyl)-ethyl]-isopropylamino]-N,N-dimethyl-acetamide and 0.102 g, (0.49 mmol) of 1,1,1-trifluoro-2-iodoethane in 4 ml DMF. The reaction was heated at 60° C. overnight. The solvent was removed, water was added and the product was extracted with ethyl acetate. The crude reaction mixture was purified by flash chromatography (dichloromethane/methanol/NH$_3$ 100:0:0→100:2.5:0.25 gradient, v:v:v). The product was dissolved in anhydrous hydrochloric acid in ethyl acetate, the solvent was removed and the product was triturated with diethyl ether. 18 mg (12.5% yield) of the title compound were isolated as a white solid.

LC-MS: MH$^+$=347

Example 80

2-[[2-(3-Benzyloxy-phenyl)-ethyl]-(cyclopropylmethyl)amino]-N-methyl-propionamide hydrochloride The above compound was synthesized according to Scheme 15

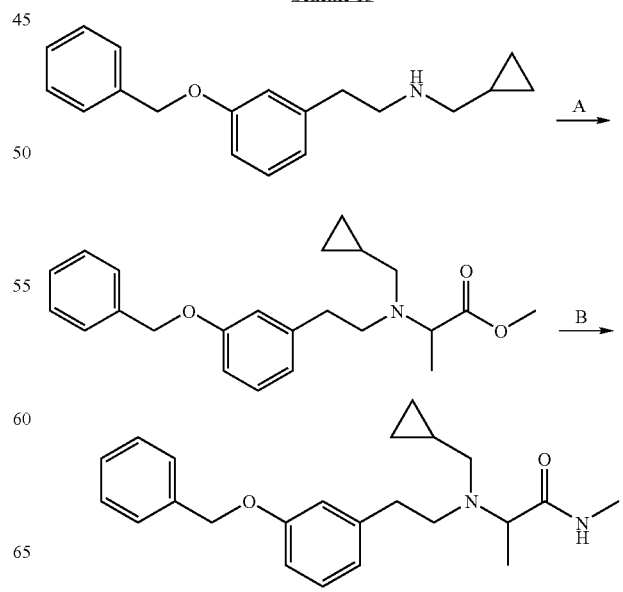

Scheme 15

Step A 2-[[2-(3-Benzyloxy-phenyl)-ethyl]-(cyclopropylmethyl)amino]-propionic Acid Methyl Ester A solution of 562 mg (2 mmol) of [2-(3-benzyloxy-phenyl)-ethyl]-(cyclopropylmethyl)amine, 0.3 ml (2.2 mmol) of triethylamine and 367 mg (2.2 mmol) of 2-bromo-propionic acid methyl ester in 20 ml of acetonitrile was refluxed for 24 hours. Solvent was removed, water was added and the product was extracted with ethyl acetate. 730 mg of the title compound were isolated in quantitative yield as a colourless oil.

$^1$H-NMR CDCl$_3$: 7.48-6.75 (m, 9H); 5.05 (s, 2H); 3.74 (q, 1H); 3.67 (s, 3H); 3.00-2.37 (m, 6H); 1.24 (d, 3H); 0.96-0.74 (m, 1H); 0.60-0.40 (m, 2H); 0.22-0.04 (m, 2H).

LC-MS: MH$^+$=368

Step B 2-[[2-(3-Benzyloxy-phenyl)-ethyl]-(cyclopropylmethyl)amino]-N-methyl-propionamide hydrochloride 730 mg (2 mmol) of 2-[[2-(3-benzyloxy-phenyl)-ethyl]-(cyclopropylmethyl)-amino]-propionic acid methyl ester were dissolved in 10 ml of dry toluene. 4 ml (8 mmol) of methylamine solution 2 M in tetrahydrofuran were added, followed by 4 ml (8 mmol) of 2 M trimethyl aluminium in heptane. The reaction was stirred at room temperature overnight. The solution was cooled to 0° C. and poured into methanol. The solvent was removed under vacuum and the crude reaction mixture was purified by flash chromatography (dichloromethane/methanol 100:5 v:v). The product was dissolved in anhydrous hydrochloric acid in ethyl acetate and the resulting salt was filtered. 500 mg (62% yield) of the title compound were isolated as a hygroscopic solid.

$^1$H-NMR CDCl$_3$: 7.48-6.69 (m, 9H); 5.06 (s, 2H); 3.56 (q, 1H); 2.80-2.14 (m, 6H); 2.47 (d, 3H); 1.17 (d, 3H); 0.89-0.65 (1H); 0.63-0.37 (m, 2H); 0.21-0.02 (m, 2H).

LC-MS: MH$^+$=366

Example 81

2-[[2-[3-Methoxy-4-(2,2,2-trifluoro-ethoxy)-phenyl]-ethyl]-(cyclopropylmethyl)amino]-N-methyl-acetamide hydrochloride The above compound was synthesized according to Scheme 16

Scheme 16

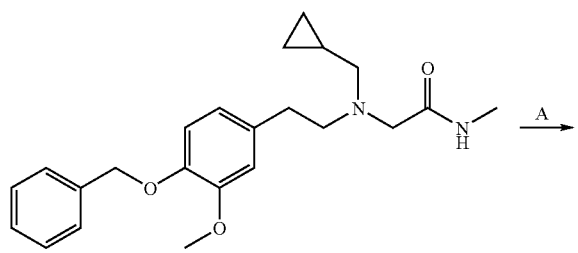

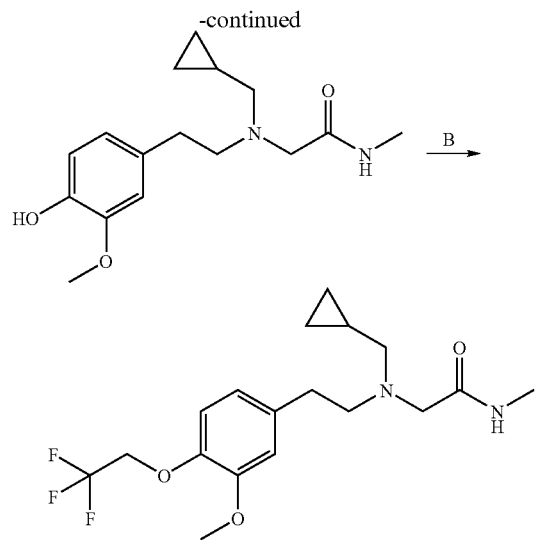

Step A 2-[[2-(4-Hydroxy-3-methoxy-phenyl)-ethyl]-(cyclopropylmethyl)amino]-N-methyl-acetamide A mixture of 0.49 g (1.28 mmol) of 2-[[2-(4-benzyloxy-3-methoxy-phenyl)-ethyl]-(cyclopropylmethyl)amino]-N-methyl-acetamide and 50 mg of Pd/C 10% in 10 ml of ethanol was hydrogenated at 40 psi for 2 hours. The catalyst was filtered off and the solvent was removed. 0.366 g (98% yield) of a yellow oil were isolated.

LC-MS: MH$^+$=293

Step B: 2-[[2-(3-Methoxy-4-(2,2,2-trifluoro-ethoxy)-phenyl)-ethyl]-(cyclopropylmethyl)amino]-N-methyl-acetamide hydrochloride A mixture of 90 mg (0.3 mmol) of 2-[[2-(4-hydroxy-3-methoxy-phenyl)-ethyl]-(cyclopropylmethyl)amino]-N-methyl-acetamide, 107 mg (0.51 mmol) of 1,1,1-trifluoro-2-iodo-ethane, 71 mg (0.51 mmol) of K$_2$CO$_3$ and 5 mg of potassium iodide in 5 ml of dimethylformamide was heated at 120° C. overnight. The mixture was filtered trough celite and the solvent was removed under vacuum. The crude product was purified by flash chromatography (dichloromethane/methanol 100:0→100:1.5 gradient, v:v). The product was dissolved in anhydrous hydrochloric acid in ethyl acetate, the solvent was removed under vacuum and the product was triturated with diethyl ether. 30 mg (27% yield) of the title compound were isolated as a white hygroscopic solid.

$^1$H-NMR CDCl$_3$: 11.49 (bs, 1H); 8.48 (bs, 1H); 6.92-6.70 (m, 3H); 4.35 (q, 2H, JHF=8.89 Hz); 4.21 (d, 2H); 3.84 (s, 3H); 3.66-3.10 (m, 6H); 2.85 (d, 3H, J=4.62 Hz); 1.37-1.17 (m, 1H); 0.81-0.69 (m, 2H); 0.53-0.42 (m, 2H)

LC-MS: MH$^+$=374

Example 82

2-[[2-(4-Cyclopentyloxy-3-methoxy-phenyl)-ethyl]-(cyclopropylmethyl)amino]-N-methyl-acetamide hydrochloride This compound was prepared according to the procedure described in Scheme 16 using the relevant reagent.

¹H-NMR CDCl₃: 11.54 (bs, 1H); 8.84 (bs, 1H); 6.80-6.69 (m, 3H); 4.70 (m, 1H); 4.17 (bd, 2H); 3.82 (s, 3H); 3.59-3.11 (m, 6H); 2.85 (d, 3H, J=4.55 Hz); 1.96-1.53 (m, 8H); 1.33-1.18 (m, 1H); 0.81-0.71 (m, 2H); 0.51-0.43 (m, 2H)

LC-MS: MH⁺=361

Example 83

2-[[2-(3'-Fluoro-biphenyl-3-yl)-ethyl]-(furan-2-ylmethyl)amino]-N-methyl-acetamide hydrochloride The above compound was synthesized according to Scheme 17

Scheme 17

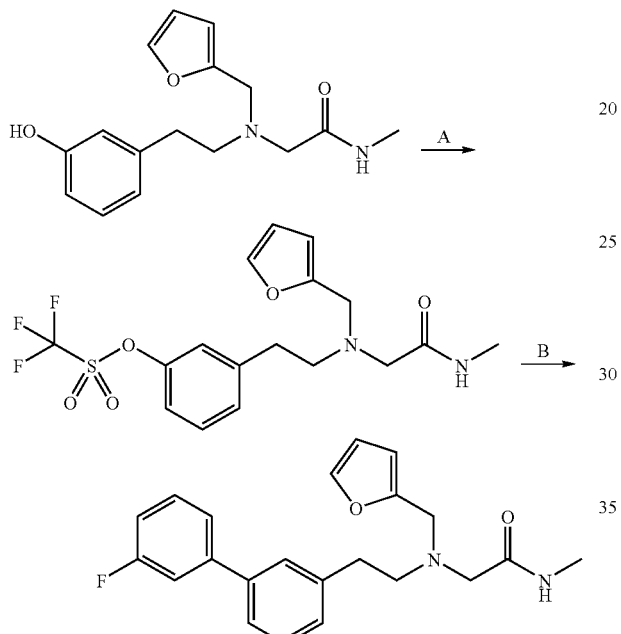

Step A 2-[[2-(3-Trifluoromethylsulfonyloxy-phenyl)-ethyl]-(furan-2-ylmethyl)amino]-N-methyl-acetamide 1.36 g (3.8 mmol) of N-phenyl-bis(trifluoromethanesulfonimide) in 10 ml of acetonitrile were added under N₂ to a mixture of 1 g (3.5 mmol) of 2-[[2-(3-hydroxy-phenyl)-ethyl]-(furan-2-ylmethyl)amino]-N-methyl-acetamide and 960 mg (7 mmol) of K₂CO₃ in 30 ml of acetonitrile/dichloromethane 2:1 mixture. The solution was stirred at room temperature overnight. The solvent was removed under vacuum, water was added and the product was extracted with ethyl acetate. The crude reaction mixture was purified by flash chromatography (hexane/ethyl acetate/dimethylformamide 1:2:0.2). 1.3 g (90% yield) of the title compound were isolated as a yellow oil.

LC-MS: MH⁺=421

Step B 2-[[2-(3'-Fluoro-biphenyl-3-yl)-ethyl]-(furan-2-ylmethyl)amino]-N-methyl-acetamide hydrochloride A mixture of 100 mg (0.24 mmol) of 2-[N-(3-trifluoromethylsulfonyloxyphenyl)-ethyl]-(furan-2-ylmethyl)amino)-N-methyl-acetamide, 48 mg (0.34 mmol) of 3-fluoro-phenyl-boronic acid, 46 mg (0.34 mmol) of K₂CO₃ and 10 mg of Pd(PPh₃)₄ in 2 ml of ethanol was heated at 110° C. with microwaves for 15 minutes. The mixture was filtered trough celite and the solvent was removed under vacuum. The crude product was purified by preparative HPLC. The product was dissolved in anhydrous hydrochloric acid in ethyl acetate. The solvent was removed under vacuum and the product was triturated with diethyl ether. 34 mg (36% yield) of the title compound were isolated as a white solid.

¹H-NMR CDCl₃: 8.79 (b, 1H); 7.56-6.81 (m, 10H); 6.51-6.48 (m, 1H); 4.61-4.35 (m, 2H); 3.77 (bs, 2H); 3.40-3.25 (m, 4H); 2.89 (d, 3H, J=4.6 Hz).

LC-MS: MH⁺=367

Example 84-91: These compounds were prepared according to the procedure described in Scheme 17 using the relevant boronic acid reagent.

Example 84

2-[[2-[3-(Thien-3-yl-)-phenyl)]-ethyl]-(furan-2-ylmethyl)amino]-N-methyl-acetamide hydrochloride

LC-MS: MH⁺=355

Example 85

2-[[2-(3'-Methoxy-biphenyl-3-yl)-ethyl]-(furan-2-ylmethyl)amino]-N-methyl-acetamide hydrochloride

LC-MS: MH⁺=379

Example 86

2-[[2-(3'-Acetylamino-biphenyl-3-yl)-ethyl]-(furan-2-ylmethyl)amino]-N-methyl-acetamide hydrochloride

LC-MS: MH⁺=406

Example 87

2-[[2-(2'-Dimethylaminomethyl-biphenyl-3-yl)-ethyl]-(furan-2-ylmethyl)amino]-N-methyl-acetamide hydrochloride

LC-MS: MH⁺=406

Example 88

2-[[2-[3-(Pyridin-3-yl)-phenyl)]-ethyl]-(furan-2-ylmethyl)amino]-N-methyl-acetamide hydrochloride

LC-MS: MH⁺=350

Example 89

2-[[2-[3-(6-Methoxy-pyridin-3-yl)-phenyl)]-ethyl]-(furan-2-ylmethyl)amino]-N-methyl-acetamide hydrochloride

LC-MS: MH⁺=380

Example 90

2-[[2-[3-(2,4-Dimethoxy-pyrimidin-5-yl)-phenyl]-ethyl]-(furan-2-ylmethyl)amino]-N-methyl-acetamide hydrochloride

LC-MS: MH⁺=411

Example 91

2-[[2-[3-(Furan-3-yl)-phenyl)]-ethyl]-(furan-2-ylmethyl)-amino]-N-methylacetamide hydrochloride

LC-MS: MH$^+$=339

Example 92

2-[[2-[3-(3,5-Dimethyl-isoxazol-4-yl)-phenyl]-ethyl]-(furan-2-ylmethyl)amino]-N-methyl-acetamide This compound was prepared according to the procedure described in Scheme 17 using the relevant boronic acid reagent but were not salified with hydrochloric acid.

LC-MS: MH$^+$=368

Example 93

2-[[2-[3-(piperidin-1-yl)-phenyl)]-ethyl]-(furan-2-ylmethyl)amino]-N-methylacetamide hydrochloride A mixture of 100 mg (0.24 mmol) of 2-[2-[(3-trifluoromethylsulfonyloxy-phenyl)-ethyl]-(furan-2-ylmethyl)amino)-N-methyl-acetamide, 41 mg (0.48 mmol) of piperidine, 28 mg (0.29 mmol) of sodium ter-butoxide, 10 mg of Pd(CH$_3$COO)$_2$ and 10 mg of N-phenyl-2-(di-tbutylphosphinyl)-indole in 2 ml of toluene was heated at 100° C. with microwaves for 15 minutes. The reaction mixture was filtered through celite and the solvent was removed under vacuum. The crude reaction mixture was purified by preparative HPLC. The product was dissolved in anhydrous hydrochloric acid in ethyl acetate, the solvent was removed under reduced pressure and the product was triturated with diethyl ether. 51 mg (55% yield) of the title compound were isolated as a yellow solid.

$^1$H-NMR CDCl$_3$: 8.66 (m, 1H); 8.10 (bs, 1H); 7.72-7.66 (m, 2H); 7.51-7.33 (m, 2H); 6.86-6.84 (m, 1H); 6.50-6.47 (m, 1H); 4.55-4.52 (m, 2H); 3.86-3.65 (m, 4H); 3.34 (bs, 6H); 2.83 (d, 3H, J=4.9 Hz); 2.72-2.65 (m, 2H); 2.09-1.92 (m, 5H)

LC-MS: MH$^+$=356

Example 94

2-[[2-(3-Benzyloxy-phenyl)-ethyl]-(tetrahydrofuran-3-ylmethyl)amino]-N,N-dimethyl-acetamide hydrochloride The above compound was synthesized according to Scheme 18

Scheme 18

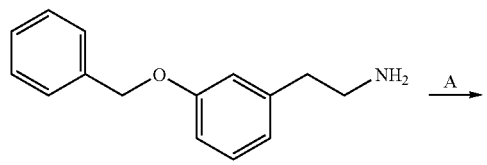

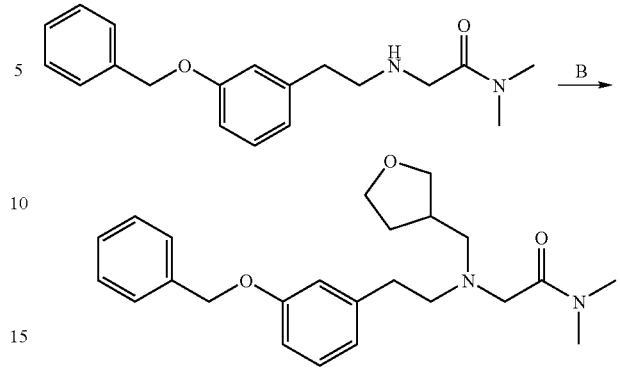

Step A 2-[2-(3-Benzyloxy-phenyl)-ethylamino]-N,N-dimethyl-acetamide

A mixture of 4.32 g (19 mmol) of 2-(3-benzyloxy-phenyl)-ethylamine, 7.9 ml (57 mmol) of triethylamine, 1.95 ml (19 mmol) of 2-chloro-N,N-dimethyl-acetamide and 332 mg (2 mmol) of potassium iodide in 110 ml of dry dimethylformamide was heated at 80° C. for 3 hours. Solvent was removed under vacuum and the crude reaction mixture was purified by flash chromatography (dichloromethane/methanol/NH$_3$ 100:3:0.5, v:v:v). 3 g (51% yield) of the title compound were isolated as a yellow solid.

LC-MS: MH$^+$=313

Step B 2-[[2-(3-Benzyloxy-phenyl)-ethyl]-(tetrahydrofuran-3-ylmethyl)amino]-N,N-dimethyl-acetamide hydrochloride 1.06 g (22 mmol) of NaBH$_4$ were added portionwise to a mixture 2.9 g (9.3 mmol) of 2-[2-(3-benzyloxy-phenyl)-ethylamino]-N,N-dimethyl-acetamide, 1.28 ml (14.1 mmol) of tetrahydrofuran-3-carbaldehyde and 4 g of 4 Å molecular sieves in 130 ml of 1,2-dichloroethane. The reaction mixture was stirred at room temperature overnight. Aqueous ammonium chloride was added, the solvent was removed under vacuum, the residue was extracted with ethyl acetate and the organic phase was washed with an aqueous saturated solution of K$_2$CO$_3$. The solvent was removed under reduced pressure and the product was dissolved in anhydrous an hydrous hydrochloric acid in ethyl acetate. The solvent was removed and the product was triturated with diethyl ether. 3.2 g (80% yield) of the title compound were isolated as a yellow solid.

$^1$H-NMR CDCl$_3$: 7.45-7.32 (m, 5H); 7.23-7.19 (m, 1H); 6.89-6.85 (m, 3H); 5.05 (s, 2H); 4.14-2.98 (m, 14H); 2.92 and 2.86 (2s, 6H); 2.82-2.71 (m, 1H).

LC-MS: MH$^+$=397

Example 95

2-[[2-[3-(2,2,2-Trifluoro-ethoxy)-phenyl]-ethyl]-(tetrahydrofuran-3-ylmethyl)amino]-N,N-dimethyl-acetamide hydrochloride The above compound was synthesized according to Scheme 19

Scheme 19

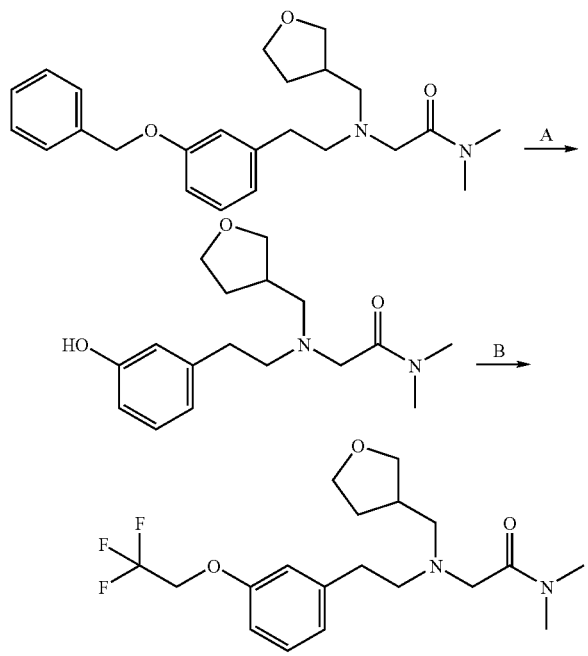

Step A 2-[[2-(3-Hydroxy-phenyl)-ethyl]-(tetrahydro-furan-3-ylmethyl)amino]-N,N-dimethyl-acetamide A mixture of 2.4 g (6.05 mmol) of 2-[[2-(3-benzyloxy-phenyl)-ethyl]-(tetrahydrofuran-3-ylmethyl)amino]-N,N-dimethyl-acetamide and 200 mg of Pd/C 10% in methanol/acetic acid 10:1 (70 ml) was hydrogenated 18 hours at 60 psi. The catalyst was filtered off and the solvent was removed under vacuum. The crude reaction mixture was purified by flash chromatography (dichloromethane/methanol/$NH_3$ 97:3:0.3, v:v:v). 1.63 g (88% yield) of the title compound were isolated as a yellow oil.

LC-MS: $MH^+$=307

Step B 2-[[2-[3-(2,2,2-trifluoro-ethoxy)-phenyl]-ethyl]-(tetrahydrofuran-3-ylmethyl)amino]-N,N-dimethyl-acetamide hydrochloride A mixture of 100 mg (0.33 mmol) of 2-[[2-(3-hydroxy-phenyl)-ethyl]-(tetrahydrofuran-3-ylmethyl)amino]-N,N-dimethyl-acetamide, 139 mg (0.66 mmol) of 1,1,1-trifluoro-2-iodo-ethane, 90 mg (0.66 mmol) of $K_2CO_3$ and 5 mg of potassium iodide in 4 ml of dimethylformamide was refluxed overnight. The mixture was filtered through celite and the solvent was removed under vacuum. The crude reaction mixture was purified by preparative HPLC. The product was dissolved in ethyl acetate/hydrochloric acid, the solvent was removed and the product was triturated with diethyl ether. 18 mg (13% yield) of the title compound were isolated as a yellow solid.

LC-MS: $MH^+$=389

Example 96

2-[[2-(3-Butoxy-phenyl)-ethyl]-(tetrahydrofuran-3-ylmethyl)amino]-N,N-dimethyl-acetamide hydrochloride The above compound was synthesized according to Scheme 20

Scheme 20

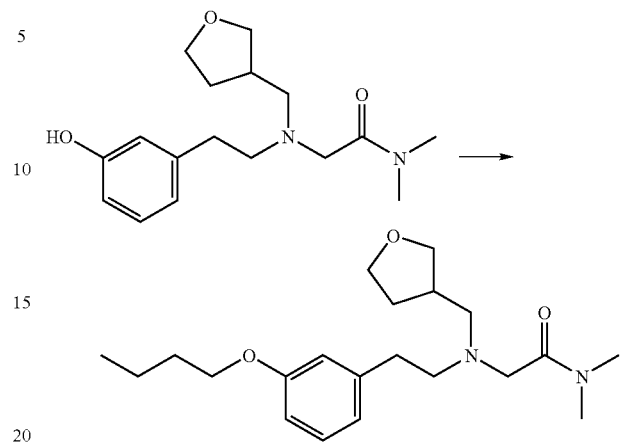

A solution of 2-[[2-(3-hydroxy-phenyl)-ethyl]-(tetrahydrofuran-3-ylmethyl)amino]-N,N-dimethyl-acetamide (1.0 g 3.3 mmol), 1-bromobutane (0.43 ml, 4 mmol), potassium carbonate (680 mg 5 mmol), potassium iodine (50 mg, 0.3 mmol), in DMF (30 ml) was refluxed for 16 h. After filtration over celite pad, the solution was evaporated from the solvent and the crude oil obtained purified by preparative HPLC. The hydrochloride salt was prepared by adding HCl 1N in AcOEt to the free amine dissolved in ethyl ether. After filtration, 690 mg (50% yield) the title compound was obtained as a white solid of 99% purity.

1H-NMR ($CDCl_3$) 12.54 (broad signal, 1H); 7.25-6.73 (m, 4H); 4.28-3.16 (m, 12H); 3.93 (t, 2H); 2.92 (s, 3H); 2.87 (s, 3H); 2.85-2.67 (m, 1H); 2.36-1.86 (m, 2H); 1.83-1.66 (m, 2H); 1.58-1.38 (m, 2H); 0.97 (t, 3H J=8.3 Hz)

LC-MS: $MH^+$=363.43

Example 96bis

2-[[2-(3-Butoxy-phenyl)-ethyl]-(tetrahydrofuran-3-ylmethyl)amino]-N,N-dimethyl Acetamide (R) and (S) Enantiomers The racemic mixture of 2-[[2-(3-butoxy-phenyl)-ethyl]-(tetrahydrofuran-3-ylmethyl)amino]-N,N-dimethyl-acetamide hydrochloride obtained according to Example 96 was separated using the chiral column CHIRALPAC® AD 20 μm–250×21 mm, mobile phase methanol/diethylamine 100/0.1 (v/v), flow rate 20 ml/min detection UV 275 nm, temperature 25° C.

The retention time of the first and the second eluted enantiomer, obtained as a honey-like yellowish bases, was 5.2 min and 6.7 min respectively. The $[\alpha]_D$ of the first eluted enantiomer is −10°, c=0.1, MeOH (20° C.) and the [α]D of the second eluted enantiomer is: +10°, c=0.1, MeOH (20° C.)

The enantiomeric excess of both was >99.5%

Example 97

2-[[2-(3-Butoxy-phenyl)-ethyl]-(furan-2-ylmethyl)amino]-N-methyl-acetamide hydrochloride This compounds was prepared according to the procedure described in Scheme 20 starting from 2-[[2-(3-hydroxy-phenyl)-ethyl]-(furan-2-ylmethyl)amino]-N-methyl-acetamide prepared as described in the Example 52

LC-MS: MH+=345

Example 98

2-[[2-[4-Fluoro-3-(2,2,2-trifluoro-ethoxy)-phenyl]-ethyl]-(tetrahydrofuran-3-ylmethyl)amino]-N,N-dimethyl-acetamide hydrochloride The above compound was synthesized according to Scheme 21

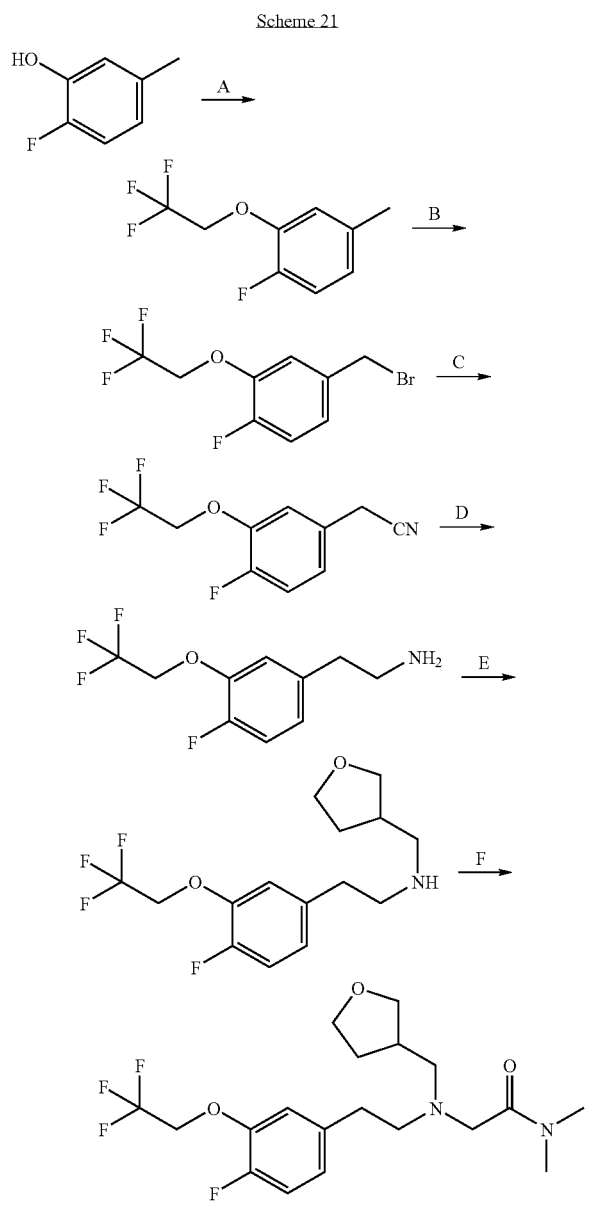

Step A 1-Fluoro-4-methyl-2-(2,2,2-trifluoro-ethoxy)-benzene 1.05 g (26 mmol) of NaH 60% were added portionwise to a solution of 2.9 g (23 mmol) of 2-fluoro-5-methyl-phenol in 15 ml of dry dimethylformamide. The mixture was stirred at room temperature for 30 minutes. 6.35 g (25 mmol) of toluene-4-sulfonic acid 2,2,2-trifluoro-ethyl ester were added and the reaction mixture was stirred at room temperature overnight. The reaction mixture was poured into water and extracted with diethyl ether. The crude product was purified by flash chromatography (hexane/ethyl acetate 9:1, v:v) to give 2.7 g (56% yield) of the title compound.

$^1$H-NMR CDCl$_3$: 7.05-6.77 (m, 3H); 4.40 (q, 2H, JH-F=8.48 Hz); 2.31 (s, 3H)

Step B 4-Bromomethyl-1-fluoro-2-(2,2,2-trifluoro-ethoxy)-benzene

A mixture of 2.68 g (12.8 mmol) of 1-fluoro-4-methyl-2-(2,2,2-trifluoro-ethoxy)-benzene, 2.3 g (12.9 mmol) of NBS and 140 mg of dibenzoylperoxide in 60 ml of CCl$_4$ was refluxed for 6 hours. Solvent was removed and the crude residue was used without any further purification for the next step.

Step C [4-Fluoro-3-(2,2,2-trifluoro-ethoxy)-phenyl]-acetonitrile 900 mg (13.8 mmol) of KCN were added to a solution of 3.3 g (11.5 mmol) of 4-bomomethyl-1-fluoro-2-(2,2,2-trifluoro-ethoxy)-benzene in 30 ml of dry dimethylsulfoxide. The reaction mixture was stirred for 1 hour at room temperature. Water was added and the product was extracted with diethyl ether. The solvent was removed under vacuum and the crude residue was purified by flash chromatography (hexane/ethyl acetate 8:2 v:v). 1.4 g (52% yield) of the title compound were isolated as a white solid.

$^1$H-NMR CDCl$_3$: 7.21-6.92 (m, 3H); 4.41 (q, 2H, JH-F=8.48 Hz); 3.68 (s, 2H)

Step D 2-[4-Fluoro-3-(2,2,2-trifluoro-ethoxy)-phenyl]-ethylamine 800 mg (10 mmol) of borane-methyl sulfide complex were added to a solution of 1.23 g (5.27 mmol) of [4-fluoro-3-(2,2,2-trifluoro-ethoxy)-phenyl]-acetonitrile in 50 ml of dry tetrahydrofuran. The reaction mixture was refluxed for 4 hours. Solvent was removed and then water was added. A first extraction with diethyl ether allowed to partially purify the crude reaction mixture. The resulting aqueous layer was then basified with NH$_4$OH, and the product was extracted with dichloromethane. After removal of the solvent 1 g (80% yield) of the title compound was isolated as a yellow solid.

$^1$H-NMR CDCl$_3$: 7.10-6.98 (m, 1H); 6.92-6.80 (m, 2H); 4.42 (q, 2H, JH-F=8.5 Hz); 4.42 (q, 2H); 2.95 (t, 2H, J=6.55 Hz); 2.70 (t, 2H, J=6.55 Hz)

Step E [2-[4-Fluoro-3-(2,2,2-trifluoro-ethoxy)-phenyl]-ethyl]-(tetrahydrofuran-3-ylmethyl)amine A mixture of 500 mg (2.1 mmol) of 2-[4-fluoro-3-(2,2,2-trifluoro-ethoxy)-phenyl]-ethylamine, 210 mg (2.1 mmol) of tetrahydrofuran-3-carbaldehyde and 2 g of 4 Å molecular sieves in 30 ml of dry dichloromethane was stirred at room temperature for 30 minutes. 630 mg (2.9 mmol) of NaBH(OAc)$_3$ were added portionwise. The reaction mixture was stirred for 4 hours at room temperature. An aqueous 5% solution of NaHCO$_3$ was added and the product was extracted with dichloromethane. The crude product was purified by flash chromatography (dichloromethane/methanol/NH$_3$ 100:9:0.5 v:v:v). 300 mg (44% yield) of the title compound were isolated as an oil.

¹H-NMR CDCl₃: 7.09-6.97 (m, 1H); 6.92-6.81 (m, 2H); 4.41 (q, 2H, JH-F=8.7 Hz); 3.90-3.66 (m, 3H); 3.51-4.40 (m, 1H); 2.91-2.59 (m, 6H); 2.54-2.24 (m, 1H); 2.11-1.92 (m, 1H); 1.64-1.46 (m, 1H)

Step F 2-[[2-[4-Fluoro-3-(2,2,2-trifluoro-ethoxy)-phenyl]-ethyl]-(tetrahydrofuran-3-ylmethyl)amino]-N,N-dimethyl-acetamide hydrochloride A mixture of 85 mg (0.26 mmol) of [2-[4-fluoro-3-(2,2,2-trifluoro-ethoxy)-phenyl]-ethyl]-(tetrahydrofuran-3-ylmethyl)amine, 0.06 ml of triethylamine and 48 mg (0.39 mmol) of 2-chloro-N,N-dimethyl-acetamide in 3 ml of dimethylformamide was heated for 1 hour to 120° C. with microwaves. The solvent was removed under vacuum. The crude product was purified by flash chromatography (dichloromethane/methanol/NH₃ 100:3:0.3 v:v:v). The product was dissolved in anhydrous hydrochloric acid in ethyl acetate, the solvent was removed under reduced pressure and the product was triturated with diethyl ether. 74 mg (65% yield) of the title compound were isolated as a brown solid.

¹H-NMR CDCl₃: 7.07-6.80 (m, 3H); 4.41 (q, 2H); 3.77 (m, 3H); 3.50 (m, 1H); 3.33 (bm, 2H); 2.98-2.32 (m, 13H); 1.94 (m, 1H); 1.54 (m, 1H)

LC-MS: MH⁺=407

Example 99

2-[[2-[4-Fluoro-3-(2,2,2-trifluoro-ethoxy)-phenyl]-ethyl]-(tetrahydrofuran-3-ylmethyl)amino]-1-pyrrolidin-1-yl-ethanone hydrochloride This compound was obtained as a brown solid in 74% yield following the same procedure described in Scheme 21 for the synthesis of 2-[[2-[4-fluoro-3-(2,2,2-trifluoro-ethoxy)-phenyl]-ethyl]-(tetrahydrofuran-3-ylmethyl)amino]-N,N-dimethyl-acetamide, using 2-chloro-1-pyrrolidin-1-yl-ethanone as the reagent instead of 2-chloro-N,N-dimethyl-acetamide.

¹H-NMR CDCl₃: 7.05-6.81 (m, 3H), 4.43 (q, 2H), 3.77 (m, 3H), 3.54-3.31 (m, 7H), 3.01-2.33 (m, 7H), 2.06-1.77 (m, 5H), 1.58 (m, 1H)

LC-MS: MH⁺=433

Example 100

2-[[2-[3-(2,2,2-Trifluoro-ethoxy)-phenyl]-ethyl]-(tetrahydrofuran-3-yl)amino]-N,N-dimethyl-acetamide hydrochloride The above compound was synthesized according to Scheme 22

Scheme 22

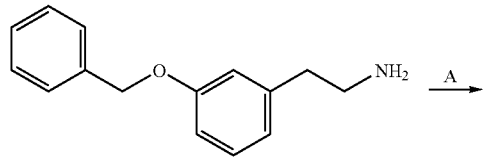

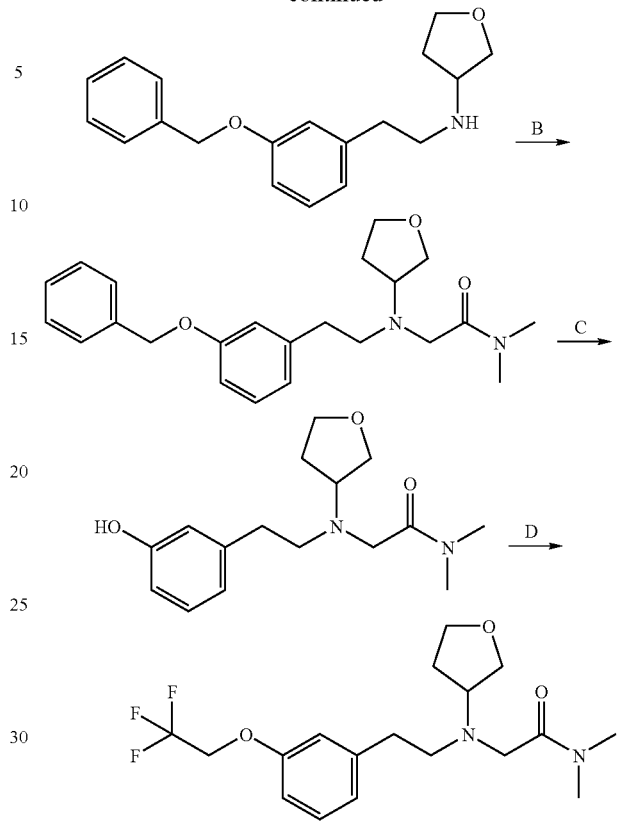

Step A [2-(3-Benzyloxy-phenyl)-ethyl]-(tetrahydrofuran-3-yl)amine

A solution of dihydro-furan-3(2H)-one in 50 ml of dichloromethane was added to a suspension of 1.99 g (7.5 mmol) of 2-(3-benzyloxy-phenyl)-ethylamine and 1.05 ml (7.5 mmol) of triethylamine in 70 ml of 1,2-dichloroethane. The mixture was stirred at room temperature for 15 minutes then 3.2 g (15.1 mmol) of NaBH(CH₃COO)₃ were added portionwise. The reaction mixture was stirred at room temperature overnight. Water was added and the reaction mixture was extracted with dichloromethane Solvent was removed under vacuum and the crude residue was purified by flash chromatography (dichloromethane/methanol/NH₃ 100:3:0.9 v:v:v). 1.35 g (60% yield) of the title compound were isolated as a brown solid.

¹H-NMR CDCl₃: 7.47-7.15 (m, 6H), 6.87-6.79 (m, 3H), 5.03 (s, 2H), 4.07-3.93 (m, 1H), 3.86-3.69 (m, 3H), 3.59-3.47 (m, 1H), 3.03-2.93 (m, 4H), 2.26-1.85 (m, 2H)

LC-MS: MH⁺=298

Step B 2-[[2-(3-Benzyloxy-phenyl)-ethyl]-(tetrahydrofuran-3-yl)amino]-N,N-dimethyl-acetamide A mixture of 0.8 g (2.69 mmol) of [2-(3-benzyloxy-phenyl)-ethyl]-(tetrahydrofuran-3-yl)amine, 0.56 ml (4.03 mmol) of triethylamine and 0.415 ml (4.03 mmol) of 2-chloro-N,N-dimethyl-acetamide in 5 ml of dry dimethylformamide was heated to 120° C. for 2 hours with microwaves. Solvent was removed under vacuum and the crude residue was purified by flash chromatography (dichloromethane/methanol: 100:3, v:v). 0.611 g (59% yield) of the title compound were isolated as a yellow oil.

LC-MS: MH$^+$=383

Step C 2-[[2-(3-Hydroxy-phenyl)-ethyl]-(tetrahydrofuran-3-yl)amino]-N,N-dimethyl-acetamide A mixture of 0.61 g (1.59 mmol) of 2-[[2-(3-Benzyloxy-phenyl)-ethyl]-(tetrahydrofuran-3-yl)amino]-N,N-dimethyl-acetamide and 60 mg of Pd/C 10% in 10 ml of ethanol was hydrogenated for 2 hours at 40 psi. The catalyst was filtered off and the solvent was removed under vacuum. The crude residue was triturated with diethyl ether and filtered. 0.45 g (96% yield) of a yellow solid were isolated.

$^1$H-NMR CDCl$_3$: 7.18-7.06 (m, 1H); 6.78-6.65 (m, 3H); 6.50 (bs, 1H); 4.04-3.90 (m, 1H); 3.84-3.64 (m, 4H); 3.59-3.35 (m, 2H); 3.03-2.87 (s+m, 7H); 2.80-2.67 (m, 2H); 2.13-1.83 (m, 2H)

LC-MS: MH$^+$=293

Step D 2-[[2-[3-(2,2,2-trifluoro-ethoxy)-phenyl]-ethyl]-(tetrahydrofuran-3-yl)amino]-N,N-dimethyl-acetamide hydrochloride A mixture of 124 mg (0.424 mmol) of [[2-(3-hydroxy-phenyl)-ethyl]-(tetrahydrofuran-3-yl)amino]-N,N-dimethyl-acetamide, 178 mg (0.848 mmol) of 1,1,1-trifluoro-2-iodo-ethane, 117 mg (0.854 mmol) of K$_2$CO$_3$ and 5 mg of potassium iodide in 4 ml of dimethylformamide was heated for 2 hours to 120° C. with microwaves. The mixture was filtered through celite and the solvent was removed under vacuum. The crude residue was purified by flash chromatography (dichloromethane/methanol 100:0→100:2 gradient, v:v). The product was dissolved in anhydrous hydrochloric acid in ethyl acetate, the solvent was removed under reduced pressure and the product was triturated with diethyl ether. 20 mg (13% yield) of the title compound were isolated as white solid.

LC-MS: MH$^+$=375

Example 101

2-[[2-[3-(3,5-Dimethyl-isoxazol-4-yl)-phenyl]-ethyl]-(tetrahydrofuran-3-yl)amino]-N,N-dimethyl-acetamide The above compound was synthesized according to Scheme 23

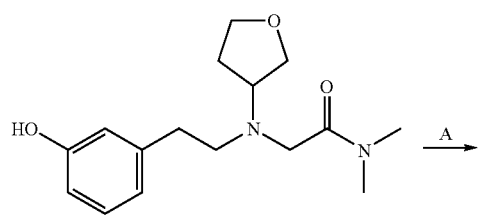

Scheme 23

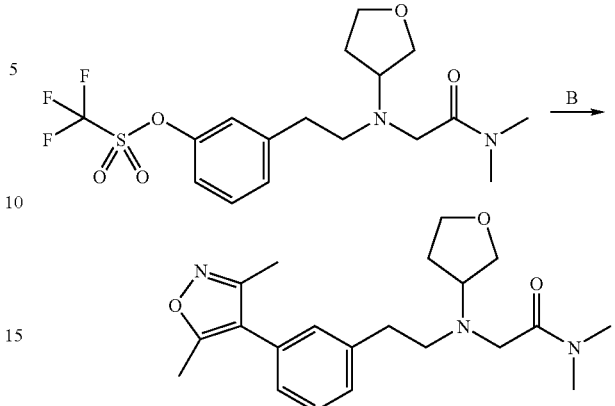

-continued

Step A 2-[[2-(3-Trifluoromethylsulfonyloxy-phenyl)-ethyl]-(tetrahydrofuran-2-yl)amino]-N,N-dimethyl-acetamide 164 mg (0.451 mmol) of N-phenyl-bis(trifluoromethanesulfonimide) in 2 ml of acetonitrile were added under N$_2$ to a mixture of 120 mg (0.41 mmol) of 2-[[2-(3-hydroxy-phenyl)-ethyl]-(tetrahydrofuran-3-yl)amino]-N,N-dimethyl-acetamide and 113 mg (0.82 mmol) of K$_2$CO$_3$ in 3 ml of acetonitrile. The reaction mixture was stirred at room temperature overnight. The solvent was removed under vacuum, water was added and the product was extracted with ethyl acetate. 150 mg (86% yield) of the title compound were isolated as a yellow oil.

LC-MS: MH$^+$=425

Step B 2-[[2-[3-(3,5-Dimethyl-isoxazol-4-yl)-phenyl]-ethyl]-(tetrahydrofuran-3-yl)amino]-N,N-dimethyl-acetamide hydrochloride A mixture of 280 mg (0.66 mmol) of 2-[[(3-trifluoromethylsulfonyloxy-phenyl)-ethyl]-(tetrahydrofuran-2-yl)amino]-N,N-dimethyl-acetamide, 81 mg (0.57 mmol) of 3,5-dimethoxyisoxazole-4-boronic acid, 80 mg (0.58 mmol) of K$_2$CO$_3$ and 10 mg of Pd(PPh$_3$)$_4$ in 4 ml of ethanol was heated at 110° C. with microwaves for 15 minutes. The mixture was filtered through celite and the solvent was removed under vacuum. The crude product was purified by flash chromatography (dichloromethane/methanol 100:0→100:3 gradient). The product was dissolved in anhydrous HCl in ethyl acetate. The solvent was then removed under reduced pressure and the product was triturated with diethyl ether. 85 mg (0.21 mmol, yield: 31%) of the title compound were isolated as a white solid.

$^1$H-NMR CDCl$_3$: 7.44-7.12 (m, 4H); 4.57-4.39 (bs, 1H); 4.39-3.72 (m, 7H); 3.61-3.05 (m, 3H); 2.99 (m, 6H); 2.74-2.51 (m, 1H); 2.41 (s, 3H); 2.37-2.24 (m, 1H), 2.27 (s, 3H)

LC-MS: MH$^+$=372

Example 102

2-[[2-(3-Piperidin-1-yl-phenyl)-ethyl]-(tetrahydrofuran-3-ylmethyl)amino]-N,N-dimethyl-acetamide hydrochloride The above compound was synthesized according to Scheme 24

Scheme 24

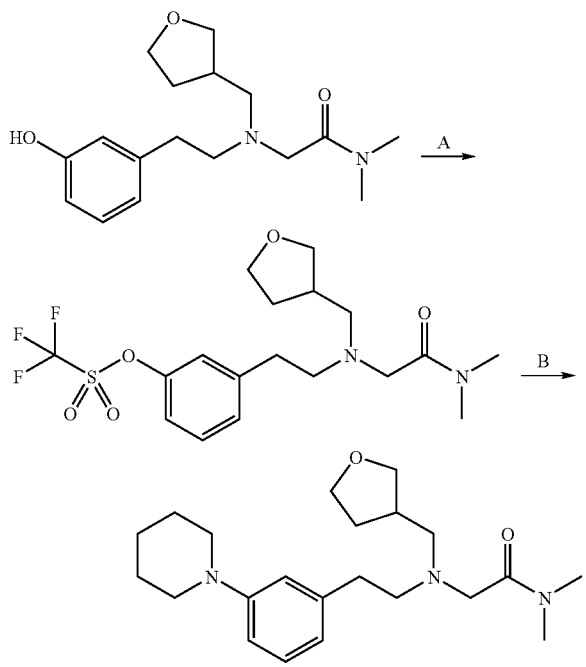

Step A 2-[[2-(3-Trifluoromethylsulfonyloxy-phenyl)-ethyl]-(tetrahydrofuran-3-yl)amino]-N,N-dimethyl-acetamide 943 mg (2.64 mmol) of N-phenyl-bis(trifluoromethanesulfonimide) in 4 ml of acetonitrile were added under N₂ to a mixture of 735 mg (2.4 mmol) of 2-[[2-(3-hydroxy-phenyl)-ethyl]-(tetrahydrofuran-3-ylmethyl)amino]-N,N-dimethyl-acetamide and 664 mg (4.8 mmol) of $K_2CO_3$ in 15 ml of acetonitrile. The reaction mixture was stirred at room temperature overnight. The solvent was removed under vacuum, water was added and the product was extracted with ethyl acetate. The crude product was purified by flash chromatography (hexane/ethyl acetate/triethylamine 1:2:0.2, v:v:v). 399 mg (38% yield) of the title compound were isolated as a yellow oil.

LC-MS: MH⁺=439

Step B 2-[[2-(3-Piperidin-1-yl-phenyl)-ethyl]-(tetrahydrofuran-3-ylmethyl)amino]-N,N-dimethyl-acetamide A mixture of 129 mg (0.29 mmol) of 2-[[(3-trifluoromethyl-sulfonyloxy-phenyl)-ethyl]-(tetrahydrofuran-3-yl) amino]-N,N-dimethyl-acetamide, 50 mg (0.58 mmol) of piperidine, 34 mg (0.35 mmol) of sodium tert-butoxide, 10 mg of Pd(OAc)₂ and 10 mg of N-phenyl-2-(di-t-butyl phosphinyl)-indole in 2 ml of toluene was heated to 110° C. with microwaves for 15 minutes. The mixture was filtered through celite and the solvent was removed under vacuum. The crude product was purified by preparative HPLC, dissolved in anhydrous HCl in ethyl acetate and the solvent was removed under reduced pressure. The product was triturated with diethyl ether. 23 mg (19% yield) of the title compound were isolated as a yellow solid.

¹H-NMR CDCl₃: 7.94-7.91 (m, 2H); 7.49-7.29 (m, 2H); 4.00-3.10 (m, 17H); 3.01 (s, 3H); 2.99 (s, 3H); 2.80-2.60 (m, 3H); 2.29-2.19 (m, 1H); 1.97-1.90 (m, 4H)

LC-MS: MH⁺=374

Example 103

2-[[2-[3-(3,5-Dimethyl-isoxazol-4-yl)-phenyl]-ethyl]-(tetrahydrofuran-3-ylmethyl)amino]-N,N-dimethyl-acetamide hydrochloride A mixture of 135 mg (0.31 mmol) of 2-[[(3-trifluoromethylsulfonyloxy-phenyl)-ethyl]-(tetrahydrofuran-3-yl)amino]-N,N-dimethyl-acetamide, 61 mg (0.43 mmol) of 3,5-dimethylisoxazole-4-boronic acid, 59 mg (0.43 mmol) of $K_2CO_3$ and 10 mg of Pd(PPh₃)₄ in 3 ml of ethanol was heated at 110° C. with microwaves for 15 minutes. The mixture was filtered through celite and the solvent was removed. The crude residue was purified by preparative HPLC. The product was dissolved in ethyl acetate/hydrochloric acid, the solvent was removed and the product was triturated with diethyl ether. 44 mg (34% yield) of the title compound were isolated as a white solid.

¹H-NMR CDCl₃: 7.43-7.13 (m, 4H); 4.17-3.28 (m, 12H); 2.98 (s, 3H); 2.96 (s, 3H); 2.88-272 (m, 1H); 2.40 (s, 3H); 2.26 (s, 3H); 2.42-2.16 (m, 2H)

LC-MS: MH⁺=386

Example 104

(2S)-2-[2-[(4-Benzyloxy)-phenyl]-1-methyl-ethylamino]-propionamide hydrochloride The above compound was synthesized according to Scheme 25

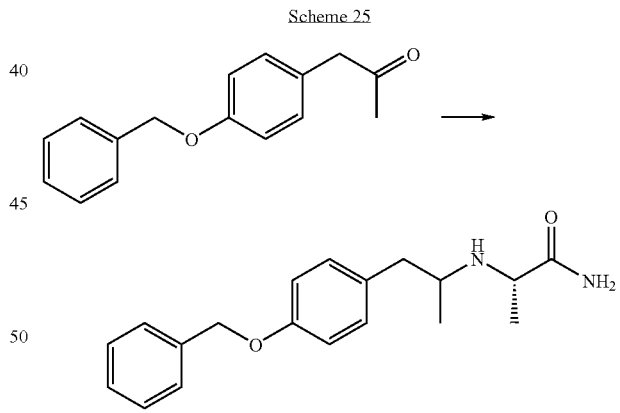

3.0 g (25 mmol) of L-alanine hydrochloride, 3 g (12.5 mmol) of 1-[(4-benzyloxy)-phenyl]-propan-2-one, 1.33 g (12.5 mmol) of Na₂CO₃ and 2 g of 4 Å molecular sieves in 150 ml of methanol were stirred at 40° C. for 2 hours under nitrogen. 0.63 g (9.60 mmol) of NaBH₃CN were then added at room temperature and the mixture was stirred at room temperature overnight an. The vessel content was filtered, the solid was washed with methanol, the organic filtrated concentrated to a small volume and the residue was passed on a flash chromatography (chloroform/methanol/NH₃ 95:5:0.5 v:v:v). 2.94 g (58% yield) of a 7:3 diastereoisomeric mixture of the title compound was obtained by crystallizeation from ethyl acetate.

$^1$H-NMR CDCl$_3$+CF$_3$COOD 7.40 (m, 5H); 7.05 (m, 4H); 5.06 (s, 2H); 4.20 (m, 1H); 3.70-2.60 (m, 3H); 1.55 (d, 3H, J=7 Hz); 1.30 (d, 3H, J=6 Hz).

Example 105

N-Type Calcium Channel Influx Assay

IMR32 human neuroblastoma cells constitutively express both L- and N-type channels. Under differentiating conditions, IMR32 cells preferentially express on the membrane surface N-type calcium channels. The remaining L-type calcium channels were blocked using the selective L-type blocker nifedipine. In these experimental conditions only N-type channels can be detected. IMR32 cells were differentiated using 1 mM dibutyrril-cAMP and 2.5 µM bromodeoxyuridine for 8 days (4 times) in 225 cm$^2$ flask, then detached, seeded at 200,000 cells/well on 96 poly-Llysine-coated plates and further incubated for 18-24 h in the presence of differentiating buffer before use.

The Ca$^{2+}$ Kit Assay (Molecular Devices), based on a fluorescent calcium indicator and able to detect the calcium influx determined by depolarizing conditions, was used for the assay. Differentiated cells were incubated with dye loading for 30 minutes at 37° C. then, nifedipine alone (1 µM) or in the presence of ω-conotoxin (as reference standard) or test compounds were added for further 15 minutes.

The fluorescence (excitation: 485 rn, emission: 535 nm wavelength) was measured before and after (30-40 s) the automated injection of 100 mM KCl depolarizing solution using a Victor plate reader (Perkin Elmer).

The inhibition curves were calculated from 5 concentrations, each in triplicate, and the IC$_{50}$ determined using a linear regression analysis.

The compounds of the present invention inhibit N-type calcium channels with pharmacologically significant IC$_{50}$ values.

The results obtained with some compounds, which are representative of the entire class of compounds of the invention, compared with the internal standard ralfinamide, are reported in Table 1.

TABLE 1

| COMPOUND | IC$_{50}$ [µM] |
|---|---|
| 2-[[2-[3-(3-Fluoro-benzyloxy)-phenyl]-ethyl]-(furan-2-ylmethyl)amino]-N-(2-amino-2-methyl-propyl)-acetamide dihydrochloride | 2.6 |
| 2-[[2-[4-(3-Fluoro-benzyloxy)-3-methoxy-phenyl]-ethyl]-(cyclopropylmethyl)amino]-N-methyl-acetamide hydrochloride | 2.1 |
| 2-[2-[4-(3-Fluoro-benzyloxy)-3-methoxy-phenyl]-ethylamino]-1-(morpholin-4-yl)-2-phenyl-ethanone hydrochloride | 6.0 |
| 2-[[2-[4-(3-Fluoro-benzyloxy)-3-methoxy-phenyl]-ethyl]-isobutylamino]-N-methyl-acetamide hydrochloride | 4.8 |
| 2-[[2-[4-(3-Fluoro-benzyloxy)-3-methoxy-phenyl]-ethyl]-benzylamino]-1-(pyrrolidin-1-yl)-ethanone hydrochloride | 2.2 |
| 2-[[2-[4-(3-Fluoro-benzyloxy)-3-methoxy-phenyl]-ethyl]-benzylamino]-N-(2-amino-2-methyl-propyl)-acetamide hydrochloride | 2.6 |
| 2-[[2-[4-(3-Fluoro-benzyloxy)-3-methoxy-phenyl]-ethyl]-benzylamino]-N-(2-dimethylamino-ethyl)-acetamide dihydrochloride | 1.9 |
| 2-[[2-[3-(3-Fluoro-benzyloxy)-phenyl]-ethyl]-(furan-2-ylmethyl)amino]-N-(2-dimethylamino-ethyl)-acetamide dihydrochloride | 1.9 |
| 2-[[2-[4-(3-Fluoro-benzyloxy)-3-methoxy-phenyl]-ethyl]-benzylamino]-N,N-dimethyl-acetamide hydrochloride | 1.1 |
| (S)-(+)-2-[4-(2-Fluoro-benzyloxy)-benzylamino]-propanamide (ralfinamide) | 23 |

Data expressed as IC$_{50}$ values at µM concentration demonstrate that the compounds of the invention are highly potent as inhibitors of N-type calcium channels.

Example 106

L-Type Calcium Channel Influx Assay

AtT20/D16v-F2 mouse pituitary tumour cell line preferentially expresses L-type calcium channels. The remaining N-type calcium channels were blocked using the selective N-type blocker ω-conotoxin. In these experimental conditions only L type channels can be detected. AtT20 cells were grown in DMEM with 10% of FBS, 4 mM glutamine. The cells were seeded at 200,000 cells/well on 96 poly-L-lysine-coated plates and further incubated for 18-24 h, before use.

The Ca$^{++}$ Kit Assay (Molecular Devices), which is based on a fluorescent calcium indicator to detect the calcium influx determined by depolarizing conditions, was used for the assay. Cells were incubated with the calcium dye loading for 30 min at 37° C. Then, ω-conotoxin alone (1 µM) or in presence of nifedipine (as reference standard) or test compound were added for further 15 min.

The fluorescence (excitation: 485-emission: 535 nm wavelength) was measured before and after (30-40 sec) the automated injection of 100 mM KCl depolarizing solution using a Victor plate reader (Perkin Elmer).

The inhibition curves were calculated from 5 concentrations, each in triplicate, and the IC$_{50}$ determined using a linear regression analysis.

The results, obtained with some compounds which are representative of the entire class of compounds of the invention, compared with the internal standard ralfinamide, are reported in Table 2.

TABLE 2

| COMPOUND | IC$_{50}$ [µM] |
|---|---|
| 2-[[2-[3-(3-Fluoro-benzyloxy)-phenyl]-ethyl]-(furan-2-ylmethyl)amino]-N-(2-amino-2-methyl-propyl)-acetamide dihydrochloride | 2.9 |
| 2-[[2-[4-(3-Fluoro-benzyloxy)-3-methoxy-phenyl]-ethyl]-(cyclopropylmethyl)amino]-N-methyl-acetamide hydrochloride | 3.8 |
| 2-[2-[4-(3-Fluoro-benzyloxy)-3-methoxy-phenyl]-ethylamino]-1-(morpholin-4-yl)-2-phenyl-ethanone hydrochloride | 7.1 |
| 2-[[2-[4-(3-Fluoro-benzyloxy)-3-methoxy-phenyl]-ethyl]-isobutylamino]-N-methyl-acetamide hydrochloride | 3.1 |
| 2-[[2-[4-(3-Fluoro-benzyloxy)-3-methoxy-phenyl]-ethyl]-benzylamino]-1-(pyrrolidin-1-yl)-ethanone hydrochloride | 1.6 |
| 2-[[2-[4-(3-Fluoro-benzyloxy)-3-methoxy-phenyl]-ethyl]-benzylamino]-N-(2-amino-2-methyl-propyl)-acetamide dihydrochloride | 2.4 |

TABLE 2-continued

| COMPOUND | IC$_{50}$ [μM] |
|---|---|
| 2-[[2-[4-(3-Fluoro-benzyloxy)-3-methoxy-phenyl]-ethyl]-benzylamino]-N-(2-dimethylamino-ethyl)-acetamide dihydrochloride | 1.2 |
| 2-[[2-[4-(3-Fluoro-benzyloxy)-3-methoxy-phenyl]-ethyl]-(cyclopropylmethyl)amino]-N-ethyl-acetamide hydrochloride | 1.8 |
| (S)-2-[2-[4-(3-Fluoro-benzyloxy)-3-methoxy-phenyl]-ethylamino]-N-methyl-4-methyl-valeramide | 1.0 |
| 2-[[2-[4-(3-Fluoro-benzyloxy)-3-methoxy-phenyl]-ethyl]-(furan-3-ylmethyl)amino]-N-methyl-acetamide hydrochloride | 1.7 |
| 2-[[2-[3-(3-Fluoro-benzyloxy)-phenyl]-ethyl]-(furan-2-ylmethyl)amino]-N-(2-dimethylamino-ethyl)-acetamide dihydrochloride | 3.4 |
| 2-[[2-[4-(3-Fluoro-benzyloxy)-3-methoxy-phenyl]-ethyl]-benzylamino]-N,N-dimethyl-acetamide hydrochloride | 4.6 |
| (S)-(+)-2-[4-(2-Fluoro-benzyloxy)-benzylamino]-propanamide (ralfinamide) | 26 |

Data expressed as IC$_{50}$ values at μM concentration demonstrate that the compounds of the invention significantly interfere with L-type calcium channels.

Example 107

TTXs-Sodium Channel Influx Assay

ND7/23 rat dorsal root ganglion-derived cell line endogenously expresses a mixed population of TTXs sodium channels (such as Nav1.3, Nav1.2, Nav1.1, Nav1.6). These cells lack of TTXr sodium channels as shown by the absence of their respective transcripts.

ND7/23 cells were grown in DMEM supplemented with 10% FBS and 1 mM sodium piruvate.

The cells were seeded at 50,000 cells/well on 96 poly-L-lysine-coated plates and further incubated for 18-24 h before use.

The Membrane Potential Kit Assay (Molecular Devices), based on a negatively charged fluorescent dye able to monitor changes in membrane potential caused by the sodium influx due to the channel opening, was used for the assay.

Cells were incubated with the dye loading for 30 minutes at 25° C. Then, 100 nM of the toxin *Anemonia sulcata* (used as enhancer of the channel opener response) alone or in the presence of TTX (as reference standard) or test compound were added for further 15 minutes.

The fluorescence (excitation: 530 nm, emission: 565 nm wavelength) was measured before and after (40-45 s) the automated injection of the sodium channel opener veratridine (100 μM) using a Victor plate reader (Perkin Elmer).

The inhibition curves were calculated from 5 concentrations, each in triplicate, and the IC$_{50}$ determined using a linear regression analysis.

The compounds of the present invention inhibit TTXs sodium channels with pharmacologically significant IC$_{50}$ values.

The results, obtained with some compounds which are representative of the entire class of compounds of the invention, compared with the internal standard ralfinamide, are reported in Table 3.

TABLE 3

| COMPOUND | IC$_{50}$ [μM] |
|---|---|
| 2-[2-[4-(3-Fluoro-benzyloxy)-3-methoxy-phenyl]-ethylamino]-1-(morpholin-4-yl)-2-phenyl-ethanone hydrochloride | 2.1 |
| 2-[[2-[4-(3-Fluoro-benzyloxy)-3-methoxy-phenyl]-ethyl]-benzylamino]-N-ethyl-acetamide hydrochloride | 1.2 |
| 2-[[2-[4-(3-Fluoro-benzyloxy)-3-methoxy-phenyl]-ethyl]-(cyclopropylmethyl)amino]-N-methyl-acetamide hydrochloride | 3.5 |
| 2-[[2-[4-(3-Fluoro-benzyloxy)-3-methoxy-phenyl]-ethyl]-(6-methoxy-pyridin-3-ylmethyl)amino]-N-methyl-acetamide | 2.9 |
| 2-[[2-(3-Butoxy-phenyl)-ethyl]-(tetrahydrofuran-3-ylmethyl)amino]-N,N-dimethyl-acetamide hydrochloride | 2.0 |
| (S)-(+)-2-[4-(2-Fluoro-benzyloxy)-benzylamino]-propanamide (ralfinamide) | 9.5 |

Example 108

Patch Clamp Studies of Calcium Currents Inhibition

Cells and Methods:

Functional inhibition of the N-type Ca currents was studied using whole cell patch clamp methods (Hamill O. P., Marty A., Neher E., Sakmann B., Sigworth F. J. Pflugers Arch. (1981) 391: 85-100) on HEK293 cells expressing recombinant human N-type channels, obtained after transient transfection of h α1B (hCav2.2)+β1b+α2δ-1 subunits.

Membrane currents were recorded and filtered at 5 kHz with an Axon Axopatch 200B amplifier and digitized with an Axon Digidata 1322A (Axon Instruments, CA, USA). Voltage clamping of membrane potentials and data acquisition were controlled online with Axon pClamp8 software. Measuring and reference electrodes were AgCl—Ag electrodes. Cells had initial seal resistances of >1 GΩ and access resistances of 4.2±0.2 MΩ. Cells were continuously superfused with extracellular solutions using a Biologic RSC-200.

For calcium currents recording the control bath solution contained (mM): Choline chloride (70), MgCl$_2$ (1), BaCl$_2$ (20), TEA.Cl (50), Hepes (10), Glucose (10). Internal pipette solution consisted of (mM): CsCl (140), EGTA (10), MgCl$_2$ (2), Hepes (10), MgATP (1), GTP Tris (0.3).

Compounds were dissolved as 20 mM stock solutions in DMSO and then diluted to the final concentration in the external solutions.

Voltage Protocols and Data Analyses:

A two-step protocol was used to determine the voltage dependence of the block:

N-type current was activated by a 600 ms step pulse to +10 mV (test pulse) from a 5000 ms preconditioning potential of −110 mV (resting condition) or −50/−55 mV (half maximal steady-state inactivated condition), respectively.

The amplitude of calcium current peaks evoked by the respective test pulses at a frequency of 0.06 Hz were measured before and after exposure to the test substance. Tonic block of currents was calculated as the difference between the peak calcium current measured at the end of a stabilization period in the control external bath solution and peak currents measured at the end of test substance perfusion period (when steady state is reached) divided by control peaks. Drug concentration-inhibition curves were obtained by plotting tonic blocks versus drug concentrations. Dose-response curves were fitted to the tonic block data, according to the logistic equation: $y=A2+(A1-A2)/[1+(x/IC_{50})^p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The compounds of the present invention inhibit N-type calcium channels with pharmacologically significant $IC_{50}$ values.

The results, obtained with some compounds, which are representative of the entire class of compounds of the invention, compared with the internal standard ralfinamide, are reported in Table 4.

TABLE 4

| COMPOUND | $IC_{50}$ [μM] (Vhalf) |
|---|---|
| 2-[[2-[4-(3-Fluoro-benzyloxy)-3-methoxy-phenyl]-ethyl]-(cyclopropylmethyl)amino]-N-methyl-acetamide hydrochloride | 5.2 |
| 2-[[2-[4-(3-Fluoro-benzyloxy)-3-methoxy-phenyl]-ethyl]-(tetrahydrofuran-3-ylmethyl)amino]-N-methyl-acetamide hydrochloride | 11 |
| (S)-(+)-2-[4-(2-Fluoro-benzyloxy)-benzylamino]-propanamide (ralfinamide) | 15 |

Data expressed as $IC_{50}$ values at μM concentration demonstrate that the compounds of the invention are highly potent as inhibitors of N-type calcium channels.

Example 109

Patch Clamp Studies of Sodium Currents Inhibition

Cells and methods: Functional inhibition of the sodium currents was studied using whole cell patch clamp methods (Harnill O. P., Marty A., Neher E., Sakmann B., Sigworth F. J., Pflugers Arch. (1981) 391 (2): 85-100) on HEK293 cells expressing recombinant Nav 1.3 channels.

Membrane currents were recorded as described in the example above.

For sodium current recording control bath solution contained (mM): NaCl (80), Choline chloride (38), $CaCl_2$ (1.3), $MgCl_2$ (2), KCl (2), $CdCl_2$ (0.4), $NiCl_2$ (0.3), TEA.Cl (20), Hepes (10), Glucose (10). Internal pipette solution consisted of (mM): EGTA (10), NaCl (10), $CaCl_2$ (1.3), $MgCl_2$ (2), Hepes (10), CsF (130), MgATP (1).

Compounds were dissolved as 20 mM stock solutions in DMSO and then diluted to the final concentration in the external solutions.

Voltage protocols and data analyses: A two-step protocol was used to determine the voltage dependence of the block: sodium current was activated by a 30 ms step pulse to 10 mV (test pulse) from a 2000 ms preconditioning potential of −100 mV (resting condition) or −50 mV (half maximal steady-state inactivated condition), respectively.

The amplitude of sodium current peaks evoked by the respective test pulses at a frequency of 0.06 Hz were measured before and after exposure to the test substance. Tonic block of currents was calculated as the difference between the Nacurrent peak measured at the end of a stabilization period in the control external bath solution and the current peak measured at the end of test substance perfusion period (when steady state is reached) divided by control peaks. Drug concentration-inhibition curves were obtained by plotting tonic blocks versus drug concentrations. Dose-response curves were fitted to the tonic block data, according to the logistic equation: $y=A2+(A1-A2)/[1+(x/IC_{50})^p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The compounds of the present invention inhibit sodium channels with pharmacologically significant $IC_{50}$ values.

The results, obtained with compounds which are representative of the entire class of compounds of the invention, compared with the internal standard ralfinamide, are reported in Table 5.

TABLE 5

| COMPOUND | $IC_{50}$ [μM] (Vhalf) |
|---|---|
| 2-[[2-[4-(3-Fluoro-benzyloxy)-3-methoxy-phenyl]-ethyl]-(cyclopropylmethyl)amino]-N-methyl-acetamide hydrochloride | 9.8 |
| 2-[[2-(3-Butoxy-phenyl)-ethyl]-(tetrahydrofuran-3-ylmethyl)amino]-N,N-dimethyl-acetamide hydrochloride | 3.1 |
| (S)-(+)-2-[4-(2-Fluoro-benzyloxy)-benzylamino]-propanamide (ralfinamide) | 15 |

Data expressed as $IC_{50}$ values at μM concentration demonstrate that the compounds of the invention are potent as inhibitors of sodium channels.

Example 110

Inhibition of Sodium Currents in Cortical Neurons

Cell Preparation and culturing: cortical neurons were prepared from embryonic Wistar rats (E17-E19). Brains of E17/E19 rats were removed and placed in ice-cold Hank's solution (Hank's solution(Life tech. 14170-088)+glucose 30%+Pen-Strep 100×(Life Tech. 15140-122) 100 U-100 μg/ml and Hepes-NaOH 5 mM).

Cortex were isolated, cut in small parts and washed twice with Hank's solution. The solution was removed except 1-2 ml and the tissue was mechanically dissociated. After the mechanical dissociation, 5 ml of complete DMEM (Dulbecco's modified Eagle medium) (Gibco 41966-029)+FBS (Hyclone) 10%+Glutamine (Life Tech. 25030-024) 2 mM+Pen-Strep 100 U-100 μg/ml were added, and cell suspension was centrifuged for 5 min at 1000 rpm. Supernatant was removed and 5 ml of complete Neurobasal medium was added (Neurobasal medium (Life tech. 21103-049)+B27 (Life tech. 17504-044) 2%+Glutamine 2 mM+Pen-Strep 100 U-100 μg/ml).

Cells were counted and diluted in Neurobasal medium to a concentration of 400000 cells per poly-D-lysine 5 μg/ml treated Petri dish.

Cortical neurons were used from day $6^{th}$ till day $11^{th}$ after plating, and once a week Neurobasal medium was changed.

Whole Cell Patch Clamp Recordings: Experiments on cortical neurons were carried out using standard whole cell patch clamp methods (Hamill et al., 1981). Membrane currents were recorded and filtered at 5 kHz with an Axon Axopatch 200B amplifier and data digitized with an Axon Digidata 1322A (Axon Instruments, CA, USA). Protocol playing and data acquisition were controlled online with Axon pClamp8 software. Measuring and reference electrodes were AgCl—Ag electrodes. A Sutter Instrument P-87 Puller (CA, USA) was used for pulling patch clamp pipettes with a resistance of 2-3 MΩ from Harward borosilicate glass tubes. Cells were continuously superfused with extracellular solutions, using a solution changer Biologic RSC-200.

Solutions: Sodium current recording control bath solution contained (mM): NaCl 60, CholineCl 60, $CaCl_2$ 1.3, $MgCl_2$ 2, KCl 2, $CdCl_2$ 0.4, $NiCl_2$ 0.3, TEACl 20, Hepes 10, Glucose 10. Internal pipette solution consisted of (mM): CsF 65, CsCl 65, NaCl 10, $CaCl_2$ 1.3, $MgCl_2$ 2, Hepes 10, EGTA 10, MgATP 1.

Voltage protocols and data analyses: cells were clamped at −90 mV, then a two step protocol was used to determine the voltage dependence of the block. Sodium currents were activated by a 30 ms step pulse to −10 mV (test pulse) from a 200 ms preconditioning potential of −110 mV (resting condition) and a potential of ~−50 mV (half maximal steady-state condition).

Drug concentration-inhibition curves were obtained by plotting tonic blocks in the resting and depolarized condition, versus drug concentrations. Dose-response curves were fitted to the tonic block data, according to the logistic equation: $y=A2+(A1-A2)/[1+(x/IC_{50})p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The compounds of the present invention inhibit sodium currents of cortical neurons with pharmacologically significant $IC_{50}$ values.

The results, obtained with compounds which are representative of the entire class of compounds of the invention, compared with the internal standard ralfinamide, are reported in Table 6.

TABLE 6

| COMPOUND | $IC_{50}$ [µM] (Vhalf) |
| --- | --- |
| 2-[[2-(3-Butoxy-phenyl)-ethyl]-(tetrahydrofuran-3-ylmethyl)amino]-N,N-dimethyl-acetamide hydrochloride | 0.5 |
| (S)-(+)-2-[4-(2-Fluoro-benzyloxy)-benzylamino]-propanamide (ralfinamide) | 9 |

Example 111

In Vitro MAO-A and MAO-B Enzyme Activities Assay

Membrane Preparations (Crude Mitochondrial Fraction)

Male Wistar rats (Harlan, Italy—175-200 g) were sacrificed under light anaesthesia and brains were rapidly removed and homogenized in 8 volumes of ice-cold 0.32 M sucrose buffer containing 0.1 M EDTA, pH 7.4. The crude homogenate was centrifuged at 2220 rpm for 10 minutes and the supernatant recovered. The pellet was homogenized and centrifuged again. The two supernatants were pooled and centrifuged at 9250 rpm for 10 minutes at +4° C. The pellet was resuspended in fresh buffer and centrifuged at 11250 rpm for 10 minutes at +4° C. The resulting pellet was stored at −80° C.

In Vitro Enzyme Activities Assay

The enzyme activities were assessed with a radioenzymatic assay using the substrates $^{14}C$-serotonin (5-HT) and $^{14}C$-phenylethylamine (PEA) for MAO-A and MAO-B, respectively. The mitochondrial pellet (500 µg protein) was resuspended in 0.1 M phosphate buffer (pH 7.4). 500 µl of the suspension were added to a 50 µl solution of the test compound or buffer, and incubated for 30 min at 37° C. (preincubation) then the substrate (50 µl) was added. The incubation was carried out for 30 minutes at 37° C. ($^{14}C$-5-HT, 5 µM) or for 10 minutes at 37° C. ($^{14}C$-PEA, 0.5 µM).

The reaction was stopped by adding 0.2 ml of 37% HCl or perchloric acid. After centrifugation, the deaminated metabolites were extracted with 3 ml of diethyl ether (5-HT) or toluene (PEA) and the radioactive organic phase was measured by liquid scintillation spectrometry at 90% efficiency. The amount of neutral and/or acidic metabolites formed as a result of MAO activity was obtained by measuring the radioactivity of the eluate.

The activity of MAO in the sample, corresponding to a percentage of radioactivity compared with the control activity in the absence of the inhibitor, was expressed as nmoles of substrate transformed/mg protein/min.

The results, as far as the MAO-B inhibition is concerned, obtained with some compounds which are representative of the entire class of compounds of the invention, are reported in Table 7.

TABLE 7

| COMPOUND | % Inhibition MAO-B at 100 µM |
| --- | --- |
| 2-[[2-[3-(3-Fluoro-benzyloxy)-phenyl]-ethyl]-(furan-2-ylmethyl)amino]-N-(2-amino-2-methyl-propyl)-acetamide dihydrochloride | 31 |
| 2-[2-[4-(3-Fluoro-benzyloxy)-3-methoxy-phenyl]-ethylamino]-N,N-dimethyl-2-phenyl-acetamide hydrochloride | 0 |
| 2-[2-[4-(3-Fluoro-benzyloxy)-3-methoxy-phenyl]-ethylamino]-1-(morpholin-4-yl)-2-phenyl-ethanone hydrochloride | 0 |
| 2-[[2-[4-(3-Fluoro-benzyloxy)-3-methoxy-phenyl]-ethyl]-isobutylamino]-N-methyl-acetamide hydrochloride | 53 |
| 2-[[2-[4-(3-Fluoro-benzyloxy)-3-methoxy-phenyl]-ethyl]-benzylamino]-1-(pyrrolidin-1-yl)-ethanone hydrochloride | 11 |
| 2-[[2-[4-(3-Fluoro-benzyloxy)-3-methoxy-phenyl]-ethyl]-benzylamino]-N-(2-amino-2-methyl-propyl)-acetamide dihydrochloride | 32 |
| 2-[[2-[4-(3-Fluoro-benzyloxy)-3-methoxy-phenyl]-ethyl]-benzylamino]-N-(2-dimethylamino-ethyl)-acetamide dihydrochloride | 33 |
| 2-[[2-[4-(3-Fluoro-benzyloxy)-3-methoxy-phenyl]-ethyl]-benzylamino]-N-[2-(1-methyl-pyrrolidin-2-yl)-ethyl]-acetamide dihydrochloride | 39 |
| 2-[[2-[3-(3-Fluoro-benzyloxy)-phenyl]-ethyl]-(furan-2-ylmethyl)amino]-N-(2-dimethylamino-ethyl)-acetamide dihydrochloride | 34 |
| 2-[[2-[4-(3-Fluoro-benzyloxy)-3-methoxy-phenyl]-ethyl]-benzylamino]-N,N-dimethyl-acetamide hydrochloride | 3.0 |
| 2-[[2-[4-(3-Fluoro-benzyloxy)-3-methoxy-phenyl]-ethyl]-benzylamino]-N-ethyl-acetamide hydrochloride | 4.0 |
| (S)-(+)-2-[4-(3-Fluoro-benzyloxy)-benzylamino]-propanamide (safinamide) | 100 |

Data expressed as percentage of MAO-B inhibition observed in the presence of 100 µM of compound, demonstrate that the compounds of the invention are weak inhibitors of MAO-B, if compared with the internal standard safinamide.

Example 112

Complete Freund's Adjuvant Model of Chronic Inflammatory Pain

Monoarthritis was induced in rats (200 g weight) by an intra-plantar injection into the left hind paw of 100 μl of complete Freund's adjuvant (CFA) containing heat-killed and dried *Mycobacterium tubercolosis* in a mixture of paraffin oil and an emulsifying agent, mannide monooleate. The CFA injection produced an area of localized edema and inflammation starting from few h after injection, with a progressive reduction in the mechanical withdrawal threshold.

Each animal was allowed to develop the arthritis over a period of 8-9 days before testing.

Mechanical Allodynia

Mechanical allodynia thresholds were determined according to the method of Chaplan et al. (Chaplan S. R., Bach F. W., Pogrel J. W., Chung J. M., Yaksh T. L. J Neurosci Methods (1994) 53: 55-63). Rats were placed in individual plastic boxes of 24×10×15 cm on a mesh metal floor and allowed to acclimate for about 30 minutes before testing. A series of calibrated von Frey hairs (Stoelting, Wood Dale, Ill.) with logarithmically incremental stiffness ranging from 2.83 to 5.88 expressed $Log_{10}$ of [10× force in (mg)] were applied to the paw with a modified up-down method (Dixon W. J. Am. Stat. Assoc. (1965) 60: 967-978). In the absence of a paw withdrawal response to the initially selected hair, a thicker hair corresponding to a stronger stimulus was presented until a sharp withdrawal was recorded. The procedure was repeated twice. Each hair was presented perpendicularly against the paw, with sufficient force to cause slight bending, and held 2-3 s. The stimulation of the same intensity was applied five/six times to the hind paw at intervals of few sec. The mechanical threshold was expressed as $Log_{10}$ of [10× force in (mg)] indicating the force of the Von Frey hair to which the animal react (paw withdrawn, licking or shaking).

The mechanical allodynia thresholds were measured before (pre-drug) and at 30, 60, 90, 120, 240 and 360 minutes after the treatment. A 24 h threshold was also measured.

The compounds of the invention were administered in a range of doses of 0.1-100 mg/kg.

Example 113

Bennett Model of Neuropathic Pain in Rats

Effects on neuropathic pain are tested in the chronic constriction injury model in the rat (Bennett, G. J. and Xie, Y. K., A peripheral mononeuropathy in rat that produces disorders of pain sensation like those seen in man, Pain, 33 (1988) 87-107). Under pentobarbital anesthesia (Nembutal, 50 mg/kg, i.p.), unilateral multiple ligations are performed on male SpragueDawley rats (140-160 g) at the right common sciatic nerve. The sciatic nerve is exposed by blunt dissection at the level of mid-thigh and four loose ligatures (5-0 chromic catgut) are placed around the nerve taking care not to interrupt the epineural circulation. After operation, animals are allowed to recover for one week. Animals develop a cold allodynia which is stable for at least five weeks. Cold allodynia is tested on a metal plate cooled by a water bath to a constant temperature of 4° C. The animals, randomly assigned to groups of 10 for each test dose and vehicle, are observed for periods of 2 minutes before and after application of test compound and the number of brisk withdrawal reactions is counted. Several time points after application are tested. Percent maximal possible effect (% MPE) and standard error of the mean (SEM) of each time point is determined with the pre-test value used as 100% MPE. The area under the data (AUD) is calculated for the observation period and expressed as percent inhibition of vehicle control as shown in Table 8. Significance is calculated by paired t-test on the percent AUD values.

TABLE 8

| COMPOUND | Dose [mg/kg] p.o. | Change vs. Control [%] |
|---|---|---|
| 2-[[2-(3-Butoxy-phenyl)-ethyl]-(tetrahydrofuran-3-ylmethyl)amino]-N,N-dimethyl-acetamide hydrochloride | 0.1 | 35.7 |
| (S)-(+)-2-[4-(2-Fluoro-benzyloxy)-benzylamino]-propanamide (ralfinamide) | 1.0 | 23.7 |

Example 114

Maximal Electroshock Test (MES) in Mice

The maximal electroshock test (MES) is used commonly in the screening of anti-epileptic drugs in rodent models.

Animals and Apparatus: Male CD1 mice weighing 25 g were used. The procedure described by White et al. (White H. S., Woodhead J. H., Franklin M. R., Swinyard E. A., and Wolf H. H. Antiepileptic Drugs (1995) 4th ed: 99-110, Raven Press, Ltd., New York) was followed. An Ugo Basile electroconvulsive generator (Model ECT UNIT 7801) was used to deliver an electrical stimulus sufficient to produce a hindlimb tonic extensor response in at least 97% of control animals. The stimulus was delivered intra-aurally through clip electrodes in mice (0.7 s of a 40 mA shock, with a pulse train of 80 Hz having a pulse duration of 0.4 ms). The acute effect of compounds administered intraperitoneally or orally 15-60 minutes before MES induction were examined and compared with a vehicle control group. Ten mice were studied per group. Complete suppression of the hindlimb tonic extensor component of seizures was taken as evidence of anticonvulsant activity.

The compounds of the invention were administered i.v., orally or intraperitoneally at the doses of 0.1-100 mg/kg.

The results, obtained with a compound representative of the entire chemical class of the invention, administered i.v., 5 minutes before testing, compared with the internal safinamide, and reported in Table 9, demonstrate that these compounds are active as anticonvulsant drugs.

TABLE 9

| COMPOUND | 50% Protection |
|---|---|
| 2-[[2-(3-Butoxy-phenyl)-ethyl]-(tetrahydrofuran-3-ylmethyl)amino]-N,N-dimethyl-acetamide hydrochloride | (0.8 mg/kg/iv) |
| (S)-(+)-2-[4-(3-Fluoro-benzyloxy)-benzylamino]-propanamide (safinamide) | (4.0 mg/kg/iv) |

Example 115

Amphetamine and Chlordiazepoxide-Induced Hyperlocomotion in Mice

In this model, mice are treated with a mixture of d-amphetamine plus an anxiolytic dose of the benzodiazepine, chlordiazepoxide (Rushton R, Steinberg H. Combined effects of chlordiazepoxide and d-amphetamine on activity of rats in an unfamiliar environment. Nature 1966; 211:1312-3; R. Arban, G. Maraia, K. Brackenborough, L. Winyard, A. Wilson, P. Gerrard, C. Large. Evaluation of the effects of lamotrigine, valproate and carbamazepine in a rodent model of mania Behavioural Brain Research, 158: 123-132). The model has been claimed to mimic some aspects of mania in bipolar disorder. Importantly, the hyperactivity induced by the mixture of d-amphetamine and chlordiazepoxide could be prevented by prior administration of the established mood stabilizer, lithium, as well as other mood stabilizers drugs (e.g. magnesium valproate and carbamazepine). Therefore, this model has face and predictive validity as a model of bipolar disorder and represents a valuable tool to determine, if a test compound could be a potential mood stabilizer drug candidate.

Amphetamine (AMP) (2.5 mg/kg) plus chlordiazepoxide hydrochloride (CDZ) (3 mg/kg/ip) were administered to male Albino Swiss mice (25-32 g) in a volume of 10 ml/kg. The locomotor activity was recorded using Opto-M3 System (Columbus Instruments) which is multi-channel activity monitor. Opto-M3 system has 10 infrared emitters and respective amount of receivers (0.5" beam spacing), attached to the PC computer and calculating both ambulatory activity and total counts. Thus the system differentiates forward locomotion (ambulation) from stereotyped like movement (total counts). Mice were pretreated with the test compound (5 mg/kg) and 10 min later, with AMP (2.5 mg/kg) or AMP jointly with CDZ (3 mg/kg). After successive 30 min. the mice were treated again with the same dose of the test compound and were placed individually in the motor activity cages. The locomotor activity (ambulation and total activity count) was evaluated for 30 min. Each group consisted of 8-10 mice.

Statistical analysis: the data were evaluated by an analysis of variance (ANOVA), followed, when appropriate, by individual comparison with the control using Dunnett's test. Amphetamine-chlordiazepoxide administration induced a significant increase in locomotor activity.

The effect of the compound 2-[[2-(3-Butoxy-phenyl)-ethyl]-(tetrahydrofuran-3-ylmethyl)amino]-N,N-dimethyl-acetamide hydrochloride, representative of the entire chemical class of this invention, was assessed as its capacity of preventing the amphetaminechlordiazepoxide induced increase in locomotor activity as shown in FIG. 1.

Example 116

Cognitive Impairment in Schizophrenia Method

Cognitive impairment is often associated with schizophrenia and it has come to be recognized as a core element of the disorder, bearing on patient's recovery and re-integration into society.

Particular interest has recently attracted a pharmacological model of cognitive dysfunctions in schizophrenia, which is based on the effects of glutamate NMDA receptor antagonists such as phencyclidine (PCP) and ketamine (Javitt et al., 1991) which impair attention and increase "impulsivity" and "compulsive" perseveration in mice performing a complex task (Greco et al., 2005).

Materials and Methods

Animals: Male DBA/2N mice (Charles River, Italy) were used. The mice weighed 25-30 g at the start of the experiments, and were housed under temperature-controlled conditions (21° C.) with a 12 h light 12 h dark cycle (light on 7:00 am-7:00 pm). Food (Rieper, Italy) was available ad libitum. The animals had two hours of access to water at the end of each day's testing.

The five-choice serial reaction time task apparatus: The test apparatus consisted of four 21.6×17.8×12.7 cm chambers (Med Associates Inc. USA), as previously described [Greco, 2005 #26]. Stimuli and recording of responses, were managed by a SmartCtrl™ Package 8 In/16 Out (Med Associates Inc. USA) with additional interfacing by MED-PC for Windows (Med Associates Inc. USA). The running program for the 5-CSRT task was custom-written.

Behavioural procedures: habituation to liquid reinforcer and nose-poking in the holes. Mice were handled for one week and their body weight recorded. They were then water-deprived by allowing them 2-h access to water in the early evening until their body weight had stabilised (8 days). Then, over the next two days the mice were habituated in their home cages to the reinforcer (10% sucrose solution) used afterwards in the operant procedures. On the following two days mice were habituated to the operant boxes. During this stage, 10% sucrose solution was available in a small bowl placed below the receptacle hole of the box. First, mice had to learn that every 5 sec the liquid reward was available in a small cup in the receptacle hole. During this period head entries were recorded. During the next period, mice were trained to poke their noses into the illuminated holes. Immediately after a poke in the water receptacle a LED at the rear of one of the holes was turned on. A nose-poke in the lighted hole extinguished the light stimulus and the liquid dipper provided a 0.01 mL liquid reward in the receptacle hole. Any response in one of the other four holes had no consequence and was not recorded. The light stimulus was presented in all five holes in random order. A mouse was switched to the 5-CSRT task after it had completed at least 50 rewarded nose-poke trials in one 30-min session.

The five-choice serial reaction time task. The start of the session was signalled by illumination of the house-light and the delivery of a 0.01 mL liquid reward. Nose poking in the receptacle hole began the first trial. After a fixed delay (the inter-trial interval, ITI), the LED at the rear of one of the holes came on for a short period. The LED stimulus was presented the same number of times in each hole during a complete session, with the order of presentation randomised by the computer. While the light was on, and for a short period afterwards (the limited hold), responses in the hole that was illuminated (correct response) resulted in the liquid reward. Responses in the holes that had not been illuminated (incorrect responses) or failure to respond within the limited hold (omissions) caused the house-lights to be turned off for a short period (time out). Responses in the holes while the house-light was off restarted the time out. After the delivery of the liquid reward, or at the end of time out, the mouse started the next trial by poking its nose into the receptacle hole. Responses made in the holes after a correct response (perseverative responses), or after the end of time out before nose-poking into the receptacle hole, resulted in a period of time out. Responses in the holes during the ITI (anticipatory responses) also resulted in a period of time out. After anticipatory responses a nose-poke into the receptacle hole restarted the current trial. Each daily session consisted of 100 trials or 30 min of testing, whichever was completed sooner, after which all lights were turned off and further responses had no effect. In the first session of the test schedule, the stimulus and limited hold each lasted 1 min and, depending on individual performance, they were progressively reduced to 1 sec. The stimulus duration was reduced in the following sequence: 60, 30, 10, 5, 2.5, 2, 1.5 and 1 sec (baseline). The ITI and time out both lasted 2 sec during the first session and the ITI was raised to 5 sec in subsequent sessions; time out was not changed. Throughout the whole period of training and experiments each mouse had one session per day on a 5-CSRT task.

Drugs and treatment schedules. The test compound was dissolved in water and was administered intraperitonealy (IP) at the dose of 10 mg/kg. Five minutes after the treatment mice were injected with vehicle (saline) or PCP (1.5 mg/kg) and 10 min later they started the test session. In each experiment the various combination of the test compound with vehicle or PCP were administered according to a Latin-square design. At least 48 h were left between the drug testing days. During these intervening days the mice were tested on the 5-CSRT task to re-establish baseline performance and to check for any residual effects of drugs.

Statistical analysis: The main dependent variables selected for analysis were: (a) the percentage of correct responses (total correct responses/total correct+total incorrect responses×100); (b) percentage of omissions (total omissions/total correct responses+total incorrect responses+total omissions×100); (c) the number of anticipatory responses in the holes during the ITI; (d) the number of perseverative responses in the holes after a correct response. Correct responses and omissions, as percentages, were transformed according to the formula 2 arcsin(SQRT(% X/100)), to normalize the distributions in accordance with the ANOVA model (Winer, 1971).

The effects of the test compound (n=12) on PCP induced deficits in the 5-CSRT task were analysed independently by a within subjects 2×2 ANOVA with factors Drug (test compound) and PCP. Subsequently the treatment group means were compared using a post-hoc TukeyKramer test. Statistical software (SAS Institute Inc., USA) was run on MicroVAX 3500 computer (Digital, USA).

As shown in table 10, PCP caused a profound effect on attentional performance of DBA/2N mice as shown by increased anticipatory and perseverative responses. A representative compound of our invention, administered 10 mg/kg i.p., can reverse PCP-induced increase in anticipatory and perseverative responses. These results support the use of this kind of compounds for the treatment of psychiatric disorders.

TABLE 10

| | N of anticipatory resposnses | No f perseverative responses |
|---|---|---|
| Veh + veh | 1.8 ± 0.5 | 19.3 ± 14 |
| 2-[[2-(3-Butoxy-phenyl)-ethyl]-(tetrahydrofuran-3-ylmethyl)amino]-N,N-dimethyl-acetamide hydrochloride 10 mg/Kg | 3.3 ± 0.7 | 20.9 ± 1.3 |
| Veh + PCP | 10.2 ± 2.8* | 31.2 ± 5.8* |
| 2-[[2-(3-Butoxy-phenyl)-ethyl]-(tetrahydrofuran-3-ylmethyl)amino]-N,N-dimethyl-acetamide hydrochloride 10 mg/Kg + PCP | 3.7 ± 1.6# | 15.7 ± 3.1# |

Example 117

Cocaine-Induced Behavioural Sensitization Test

Drug addiction is a pathological behaviour characterized by compulsive drug seeking and intake. One animal model of these behavioral changes is the long-lasting increase in locomotor activity induced by repeated administration of psychostimulant drugs in rodents (Robinson T. E. and Berridge K. C. Brain Res. Brain Res. Rev. (1993) 18, 247-91) known as drug-induced behavioural sensitization. The effect of test compounds were evaluated in a model of cocaineinduced behavioral sensitization in rat.

Locomotor activity apparatus: Male Wistar rats weighing 200-250 g upon arrival were used. Locomotor activity was measured in sixteen identical metal wire hanging cages each measuring 36 cm (L)×25 cm (W)×20 cm (H). Each cage contained two sets of infrared emitter-detector photocells positioned along the long axis 1 cm above the grid floor and 8 cm from the front and back of the cage. Background noise was provided by a white noise generator. Movement within the cages produced photocell interruptions, which were automatically recorded by an IBM-compatible computer.

Sensitization procedure and treatment: Animals were habituated to the locomotor activity chambers for 2-3 consecutive days before the experiment. Rats received 5 daily i.p. injections of cocaine (15 mg/kg) or saline and either the test compound (0.1-100 mg/kg) or its vehicle and locomotor activity was recorded for 3 h. Ten days after the last injection of cocaine or saline (day 15), the animals were challenged with 15 mg/kg of cocaine in absence of the test compound and locomotor activity was again monitored for 3 h.

By the fifth day of treatment with cocaine, animals pretreated i.p. with vehicle showed an increased locomotor response (20% higher then the first day, p<0.05). Ten days after the last injection of cocaine or saline, the animals were challenged with 15 mg/kg of cocaine in absence of the test compound and locomotor activity was again monitored for 3 h. The rats previously treated with cocaine and that had not received the test compound are expected to show an increased locomotor activity response to cocaine (30% higher then first day, p<0.05). If the rats that had been pretreated with the test compound during the 5 day-cocaine treatment did not show an increase in locomotor activity the test compound is considered to have an effect in preventing psychostimulant drugs addiction. (Koob G. F., Sanna P. P., Bloom F. E. Neuron (1998) 21: 467-476; Robinson T. E., Berridge K. C. Brain Res Brain Res Rev (1993) 18: 247-291)

Statistical analysis: Data (total number of beam breaks in 3 hours) were analyzed using a two way ANOVA with repeated measures on one factor including the four experimental groups (i.e., saline/vehicle, saline/test compound, cocaine/vehicle and cocaine/test compound) and two time points (day 1 and day 5) followed by a simple effects analysis. A second two way ANOVA with repeated measures on one factor was used to compare day 1 and the challenge day followed by a Newman-Keuls post hoc test.

Example 118

Acute Bladder Irritation by Acetic Acid in Rats

Experiments were performed using adult anesthetized female Sprague Dawley rats (170-200 g). A catheter (PE-50) was inserted via a midline abdominal incision into the bladder through the bladder dome, and then intravesical pressure was measured to monitor bladder activity during continuous infusion of 0.15% af acetic acid. Continuous intravesical infusion of acetic acid irritates the bladder and reduces the intercontraction intervals (ICI) in anesthetized rats. ICIs, maximal contraction pressure, and pressure thresholds inducing reflex bladder contraction were measured before and after intravesical infusion of acetic acid in rats treated with compounds of the invention.

Example 119

Intermediate Bladder Irritation by Cyclophosphamide (CYP) in Rats

Experiments were performed using both adult awake and anesthetized female Sprague Dawley rats (170-200 g). Chemical cystitis was induced by CYP, which is metabolized to acrolein, an irritant eliminated in the urine. CYP (150 mg/kg/i.p.) was administered one day before the experiment. Pre-treatment with CYP causes bladder irritation and very frequent voidings with an ICI of about 150-200 seconds between voids.

Active compounds increase the ICI in both awake and anesthetized rats used in this experimental model.

Example 120

Migraine Test in Rats

Animals and surgery: Male Wistar rats (250-350 g) were anesthetized with sodium pentobarbital (50 mg/kg i.p.) dissolved in saline. The trachea and left femoral artery were cannulated for artificial ventilation (55 strokes/min) and for measurement of mean blood pressure (MBP) respectively. The femoral vein was cannulated for the intravenous administration of test agents.

Body temperature was maintained at 37-38° C. by automatic control of a heating pad. Animals were placed in a stereotaxic frame and a longitudinal incision was made in the scalp. A burr hole was drilled in the skull and a stainless steel bipolar electrode (Plastic One MS 306) was lowered into left ophthalmic branch of the trigeminal ganglion (3.8 mm dorsal to bregma, 2.5 mm lateral from the midline and 9.5 mm below the dural surface) and secured with dental cement. Correct placement of the electrode was confirmed by a brief electrical stimulation, which cause movement of the jaw due to activation of the trigeminal fiber. Following removal of the brain, the correct position of the electrode into the fiber, was visually checked at the end of each experiment.

A second hole was drilled ipsilateral of the electrode (1.5 mm rostral to bregma, and 1.5 mm lateral from the sagittal suture) and a needle probe (tip diameter 0.8 mm) of a laser doppler flowmeter was fixed pointing with its tip onto a branch of the middle cerebral artery (MCA) and Cerebral Blood Flow (CBF) change recorded on-line by the PeriFlux 4001 Laser Doppler system.

Artefacts of the laser Doppler reading during electrical stimulation of the trigeminal ganglion due to muscular movements were prevented by a bolus of i.v. injection of the neuromuscular blocker pancuronium bromide (0.6 mg/kg i.v.).

Anesthesia and neuromuscular blockade were maintained all over the experiment with an infusion of sodium pentobarbital and pancuronium (12.5 mg/kg/h+2.4 mg/kg/h, respectively).

Experimental protocol: At the end of the surgery, a pause of thirty minutes was taken in order to stabilize the measured parameters.

Rest CBF was increased by electrical stimulation with rectangular pulse of 0.5 ms length, 1-10 Hz, 0.5-1 mA for periods of 30 s. After two averaged pre-drug stimulations, vehicle or drugs were administered.

Active compounds reduce the increase in blood flow induced by trigeminal stimulation.

The invention claimed is:

1. A compound of formula I

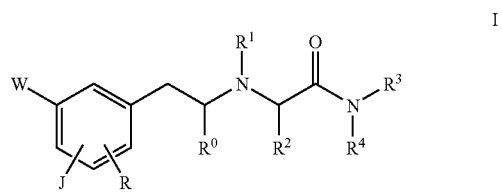

wherein:
J is a group A-[(CH$_2$)$_n$—O]$_r$ in para position with respect to the ethylamino chain wherein:
  n is zero or 1; and
  r is 1;
  A is trifluoromethyl; or phenyl optionally substituted with a halo group;
W is (C$_1$-C$_4$)alkoxy;
R is hydrogen;
R$^0$ is hydrogen; or (C$_1$-C$_2$)alkyl;
R$^1$ is hydrogen; (C$_1$-C$_4$)alkyl optionally substituted with a hydroxy group;
cyclopropylmethyl; 2-propyn-1-yl; benzyl optionally substituted with one or two (C$_1$-C$_2$)alkoxy groups on the benzene ring; thiazolyl; a 5-6 membered saturated heterocyclyl containing a nitrogen atom, optionally substituted with a (C$_1$-C$_2$)alkyl group; or heterocyclylmethyl wherein the heterocyclyl group is a 5-6 membered heterocyclyl containing 1 to 3 hetero atoms selected from nitrogen, oxygen and sulfur, optionally substituted with one or two groups selected from (C$_1$-C$_2$)alkyl, hydroxymethyl and (C$_1$-C$_2$)alkoxy;
R$^2$ is hydrogen; (C$_1$-C$_4$)alkyl; or phenyl;
R$^3$ is hydrogen; or (C$_1$-C$_4$)alkyl; and
R$^4$ is hydrogen; (C$_1$-C$_4$)alkyl optionally substituted with a group selected from amino, (C1-C4)alkylamino, di-(C$_1$-C$_4$)alkylamino, imidazolyl and pyrrolidinyl wherein the imidazolyl and the pyrrolidinyl group is optionally substituted with a (C$_1$-C$_2$)alkyl group; or benzyl; or R$_3$ and R$_4$, taken together with the adjacent nitrogen atom, form a pyrrolidinyl, morpholinyl or piperazinyl ring optionally substituted with a (C$_1$-C$_2$)alkyl group;
or a single optical isomer or mixtures thereof, or pharmaceutically acceptable salts of the single optical isomer or mixtures thereof.

2. A compound of claim 1, wherein:
J is a group A-[(CH$_2$)$_n$—O]$_r$— in para position with respect to the ethylamino chain wherein:
  n is 1; and
  r is 1;
  A is trifluoromethyl; phenyl; or phenyl substituted with a fluoro or chloro group;
W is methoxy;
R is hydrogen;
R$^0$ is hydrogen;
R$^1$ is hydrogen; (C$_1$-C$_4$)alkyl; hydroxyethyl; cyclopropylmethyl; 2-propin-1-yl; benzyl optionally substituted with one or two methoxy groups on the benzene ring;

piperidinyl optionally substituted with a methyl group; thiazolyl; or heterocyclylmethyl wherein the heterocyclyl group is selected from isoxazolyl optionally substituted with a methyl or methoxy group, imidazolyl optionally substituted with a methyl group, furanyl optionally substituted with a hydroxymethyl group, tetrahydrofuranyl, 1,2,3-thiadiazolyl, pyrazolyl optionally substituted with one or two methyl groups, pyridinyl optionally substituted with a methoxy group, thienyl and thiazolyl;

$R^2$ is hydrogen; $(C_1-C_4)$alkyl; or phenyl;

$R^3$ is hydrogen; or $(C_1-C_4)$alkyl; and $R^4$ is hydrogen; $(C_1-C_4)$alkyl optionally substituted with a group selected from amino, dimethylamino, imidazolyl and pyrrolidinyl wherein the pyrrolidinyl is optionally substituted with a methyl group; or benzyl; or $R^3$ and $R^4$ taken together with the adjacent nitrogen atom form a pyrrolidinyl, piperazinyl or morpholinyl ring optionally substituted with a methyl group;

or a single optical isomer or mixtures thereof, or pharmaceutically acceptable salts of the single optical isomer or mixtures thereof.

3. A compound of claim 1 selected from:

2-[2-[4-(3-Fluoro-benzyloxy)-3-methoxy-phenyl]-ethylamino]-N-methyl-acetamide;

2-[[2-[4-(3-Fluoro-benzyloxy)-3-methoxy-phenyl]-ethyl]-isobutylamino]-N-methyl-acetamide;

2-[[2-[4-(3-Fluoro-benzyloxy)-3-methoxy-phenyl]-ethyl]-(tetrahydrofuran-3-ylmethyl)amino]-N-methyl-acetamide;

2-[2-[4-(3-Fluoro-benzyloxy)-3-methoxy-phenyl]-ethylamino]-N,N-dimethyl-acetamide;

2-[[2-[4-(3-Fluoro-benzyloxy)-3-methoxy-phenyl]-ethyl]-benzylamino]-N,N-dimethyl-acetamide;

2-[2-[4-(3-Fluoro-benzyloxy)-3-methoxy-phenyl]-ethylamino]-N,N-dimethyl-propionamide;

2-[2-[4-(3-Fluoro-benzyloxy)-3-methoxy-phenyl]-ethylamino]-N,N-dimethyl-2-phenyl-acetamide;

2-[2-[4-(3-Fluoro-benzyloxy)-3-methoxy-phenyl]-ethylamino]-1-(morpholin-4-yl)-2-phenyl-ethanone;

2-[[2-[4-(3-Fluoro-benzyloxy)-3-methoxy-phenyl]-ethyl]-benzylamino]- acetamide;

2-[[2-[4-(3-Fluoro-benzyloxy)-3-methoxy-phenyl]-ethyl]-benzylamino]-1-(pyrrolidin-1-yl)-ethanone;

2-[[2-[4-(3-Fluoro-benzyloxy)-3-methoxy-phenyl]-ethyl]-benzylamino]-N-(2-amino-2-methyl-propyl)-acetamide;

2-[[2-[4-(3-Fluoro-benzyloxy)-3-methoxy-phenyl]-ethyl]-benzylamino]-N-(2-dimethylamino-ethyl)-acetamide;

2-[[2-[4-(3-Fluoro-benzyloxy)-3-methoxy-phenyl]-ethyl]-benzylamino]-N-[2-(1-methyl pyrrolidin-2-yl)-ethyl]-acetamide;

2-[[2-[4-(3-Fluoro-benzyloxy)-3-methoxy-phenyl]-ethyl]-(cyclopropylmethyl)amino]-N-ethyl-acetamide;

2-([2-[4-(Benzyloxy)-3-methoxy-phenyl]-ethyl)-(cyclopropylmethyl)amino]-N-methyl-acetamide;

2-[[2-[3-Methoxy-4-(2,2,2-trifluoro-ethoxy)-phenyl]-ethyl]-(cyclopropylmethyl)amino]-N-methyl-acetamide;

2-[[2-[4-(3-Fluoro-benzyloxy)-3-methoxy-phenyl]-ethyl]-(cyclopropylmethyl)amino]-N-methyl-acetamide;

(S)-2-[2-[4-(3-Fluoro-benzyloxy)-3-methoxy-phenyl]-ethylamino]-N-methyl-4-methyl-valeramide;

2-[[2-[4-(3-Fluoro-benzyloxy)-3-methoxy-phenyl]-ethyl]-(furan-3-ylmethyl)amino]-N-methyl-acetamide;

2-[[2-[4-(3-Fluoro-benzyloxy)-3-methoxy-phenyl]-ethyl]-benzylamino]-N-ethyl-acetamide; and 2-[[2-[4-(3-Fluoro-benzyloxy)-3-methoxy-phenyl]-ethyl]-(6-methoxy-pyridin-3-ylmethyl)amino]-N-methyl-acetamide;

or a single optical isomer or mixtures thereof, or pharmaceutically acceptable salts of the single optical isomer or mixtures thereof.

4. The compound 2-[[2-(3-Butoxy-phenyl)-ethyl]-(tetrahydrofuran-3-ylmethyl)amino]-N,N-dimethyl-acetamide and its pharmaceutically acceptable salts.

5. The compound of claim 4, wherein said compound is the single (R)-enantiomer, the single (S)-enantiomer, or a mixture thereof.

6. A compound according to claim 1 wherein the pharmaceutically acceptable salts are a hydrochloride.

7. A compound of claim 1 wherein:

J is a group A-$[(CH_2)_n—O]_r$ in para position with respect to the ethylamino chain wherein:

n is zero; and r is 1;

A is phenyl; or phenyl substituted with a fluoro group;

W is methoxy;

R is hydrogen;

$R^0$ is hydrogen;

$R^1$ is hydrogen; $(C_1-C_4)$alkyl; cyclopropylmethyl; benzyl; or heterocyclomethyl wherein the heterocyclyl group is selected from furanyl, tetrahydrofuranyl, and pyridinyl optionally substituted with a methoxy group;

$R^2$ is hydrogen; $(C_1-C_4)$alkyl; or phenyl;

$R^3$ is hydrogen; or $(C_1-C_4)$alkyl; and $R^4$ is hydrogen; $(C_1-C_4)$alkyl optionally substituted with a group selected from amino, dimethylamino, and pyrrolidinyl wherein the pyrrolidinyl is optionally substituted with a methyl group; or $R_3$ and $R_4$ taken together with the adjacent nitrogen atom, form a pyrrolidinyl, morpholinyl ring;

or a single optical isomer or mixtures thereof, or pharmaceutically acceptable salts of the single optical isomer or mixtures thereof.

8. A compound of claim 3 selected from:

2-[[2-[4-(3-Fluoro-benzyloxy)-3-methoxy-phenyl]-ethyl]-isobutylamino]-N-methyl-acetamide;

2-[[2-[4-(3-Fluoro-benzyloxy)-3-methoxy-phenyl]-ethyl]-(tetrahydrofuran-3-ylmethyl)amino]-N-methyl-acetamide;

2-[[2-[4-(3-Fluoro-benzyloxy)-3-methoxy-phenyl]-ethyl]-benzylamino]-N,N-dimethyl-acetamide;

2-[2[-4-(3-Fluoro-benzyloxy)-3-methoxy-phenyl]-ethylamino]-N,N-dimethyl-2-phenyl-acetamide;

2-[2-[4-(3-Fluoro-benzyloxy)-3-methoxy-phenyl]-ethylamino]-1-(morpholin-4-yl)-2-phenyl-ethanone;

2-[[2-4-(3-Fluoro-benzyloxy)-3-methoxy-phenyl]-ethyl]-benzylamino]-1-(pyrrolidin-1-yl)-ethanone;

2-[[2-[4-(3-Fluoro-benzyloxy)-3-methoxy-phenyl]-ethyl]-benzylamino]-N-(2-amino-2-methyl-propyl)-acetamide;

2-[[2-[4-(3-Fluoro-benzyloxy)-3-methoxy-phenyl]-ethyl]-benzylamino]-N-(2-dimethylamino-ethyl)-acetamide;

2-[[2-[4-(3-Fluoro-benzyloxy)-3-methoxy-phenyl]-ethyl]-benzylamino]-N-[2-(1-methyl-pyrroldin-2-yl)-ethyl]-acetamide;

2-[[2-[4-[(3-Fluoro-benzyloxy)-3-methoxy-phenyl]-ethyl]-(cyclopropylmethyl)amino]-N-ethyl-acetamide;

2-[[2-[4-(3-Fluoro-benzyloxy)-3-methoxy-phenyl]-ethyl]-(cyclopropylmethyl)amino]-N-methyl-acetamide;

(S)-2-[2-[4-(3-Fluoro-benzyloxy)-3-methoxy-phenyl]-ethylamino]-N-methyl-4-methyl-valeramide;

2-[[2-[4-(3-Fluoro-benzyloxy)-3-methoxy-phenyl]-ethyl]-(furan-3-ylmethyl)amino]-N-methyl-acetamide;

2-[[2-[4-(3-Fluoro-benzyloxy)-3-methoxy-phenyl]-ethyl]-benzylamino]-N-ethyl-acetamide; and 2-[[2-[4-(3-Fluoro-benzyloxy)-3-methoxy-phenyl]-ethyl]-(6-methoxy-pyridin-3-ylmethyl)amino]-N-methyl-acetamide;

or a single optical isomer or mixtures thereof, or pharmaceutically acceptable salts of the single optical isomer or mixtures thereof.

9. A pharmaceutical composition comprising a compound of claim 1 as active agent and a pharmaceutically acceptable excipient.

10. The pharmaceutical composition of claim 9, further comprising a second active agent.

11. A pharmaceutical composition comprising the compound of claim 4 or a single optical isomer or mixture thereof, or pharmaceutically acceptable salt of the single optical isomer or mixture thereof, and a pharmaceutically acceptable excipient.

12. A compound according to claim 4, wherein the pharmaceutically acceptable salts are a hydrochloride.

13. A compound according to claim 5, wherein the pharmaceutically acceptable salts are a hydrochloride.

14. The pharmaceutical composition of claim 11, further comprising a second active agent.

* * * * *

UNITED STATES PATENT AND TRADEMARK OFFICE
CERTIFICATE OF CORRECTION

| | | |
|---|---|---|
| PATENT NO. | : 7,855,227 B2 | |
| APPLICATION NO. | : 12/158491 | |
| DATED | : December 21, 2010 | |
| INVENTOR(S) | : Florian Thaler | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Twenty-eighth Day of June, 2011

David J. Kappos
*Director of the United States Patent and Trademark Office*